(12) United States Patent
Cheresh et al.

(10) Patent No.: US 11,021,755 B2
(45) Date of Patent: Jun. 1, 2021

(54) COMPOSITIONS AND METHODS FOR IDENTIFYING ANTI CANCER, ANTI-METASTATIC AND ANTI-STRESS AGENTS

(71) Applicant: THE REGENTS OF THE UNIVERSITY OF CALIFORNIA, Oakland, CA (US)

(72) Inventors: David Cheresh, Encinitas, CA (US); Maricel Gozo, San Diego, CA (US); Mayra Yebra, Cardiff by the Sea, CA (US); Laetitia Seguin, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 202 days.

(21) Appl. No.: 15/926,494

(22) Filed: Mar. 20, 2018

(65) Prior Publication Data
US 2018/0223376 A1 Aug. 9, 2018

Related U.S. Application Data

(62) Division of application No. 15/074,523, filed on Mar. 18, 2016, now abandoned.

(60) Provisional application No. 62/135,044, filed on Mar. 18, 2015.

(51) Int. Cl.
*C12Q 1/6886* (2018.01)
*C12N 15/00* (2006.01)
*G01N 33/574* (2006.01)
*C07K 14/705* (2006.01)

(52) U.S. Cl.
CPC ...... *C12Q 1/6886* (2013.01); *C07K 14/70557* (2013.01); *C12N 15/00* (2013.01); *G01N 33/57407* (2013.01); *G01N 33/57434* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2006/0019256 A1* | 1/2006 | Clarke | C12Q 1/6886 435/6.14 |
| 2006/0142297 A1 | 6/2006 | Barge | |
| 2007/0254893 A1 | 11/2007 | Green | |
| 2009/0048205 A1 | 2/2009 | Meyer et al. | |
| 2010/0004257 A1 | 1/2010 | Haura | |
| 2010/0092475 A1 | 4/2010 | Johns et al. | |

FOREIGN PATENT DOCUMENTS

WO 2013152313 A1 10/2013

OTHER PUBLICATIONS

Kulasingam et al., "Proteomics Analysis of Condiditoned Media from Three Breast Cancer Cell Lines" 6(11) Molecular & Cellular Proteomics 1997-2011 (2007).*
Desgrosellier et al, "An integrin $\alpha v \beta 3$-c-Src oncogenic unit promotes anchorage-independence and tumor progression," Nature Medicine, 2009, v 15, n 10, p. 1163-1170.
Mohseni et al, "A genetic screen identifies an LKBl/PAR1 signaling axis controlling the Hippo/YAP pathway," Nat. Cell Biol. 2014, v 16, n1, p. 108-117.
Kottke et al, "Detecting and targeting tumor relapse by its resistance to innate effectors at early recurrence," Nat. Med., 2013, v 19, n 12, p. 1625-1631.
Desgrosellier et al, "Integrin in cancer: biological implications and therapeutic opportunities" Nature Reviews, Jan. 10, v 10, p. 9-22, Jan. 2010.
Wilhide et al., "The human integrin beta-3 gene is 63 kb and contains 5' -UTR sequence regulating expression" Blood, Nov. 15, 1997, v 90, n 10, p. 3951-3961.

* cited by examiner

*Primary Examiner* — Nancy J Leith
(74) *Attorney, Agent, or Firm* — Greer, Burns & Crain, Ltd.; Gregory P. Einhorn

(57) ABSTRACT

In alternative embodiments, provided are products of manufacture, such as assays, chimeric nucleic acids and nucleic acid constructs, recombinant cells, and methods, comprising use of beta3-integrin (ITGB3) promoters operatively linked to a reporter, for drug screening, and in particular, screening for agents that inhibit cancer cell survival and metastasis. In alternative embodiments, compositions and methods as provided herein also can be used to identifying novel pathways that lead to acquired resistance, stemness, and anchorage independent growth; and characterizing distinct populations of cancer cells within a tumor microenvironment.

13 Claims, 50 Drawing Sheets
(30 of 50 Drawing Sheet(s) Filed in Color)
Specification includes a Sequence Listing.

FIG. 5

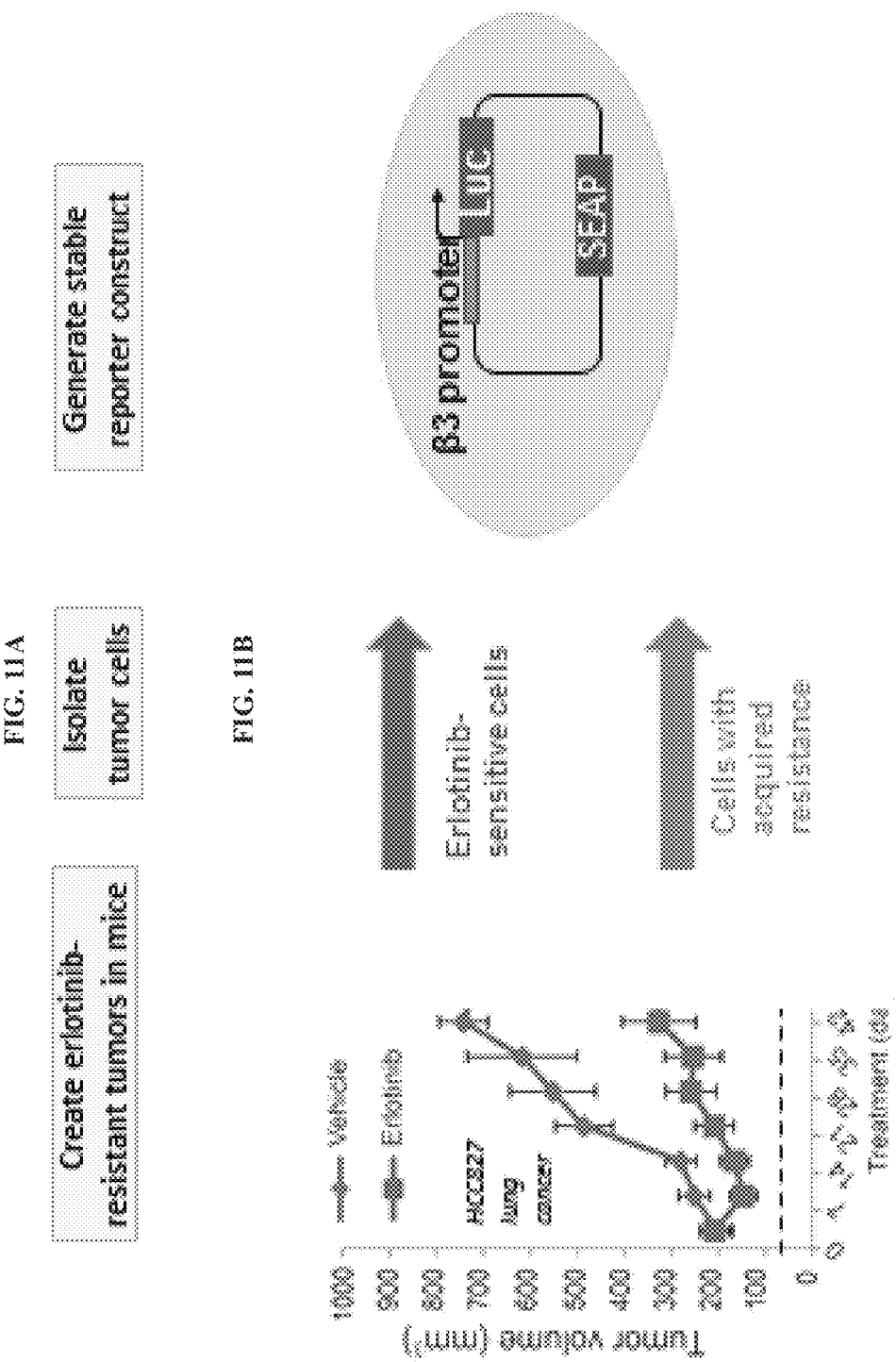

List of cell lines used for this screen to identify soluble factors

| Cell line | Disease |
|---|---|
| HCC827 | Lung |
| FG | Pancreas |
| BT474 | Breast |
| MCF10A | Breast |
| H441 | Lung |

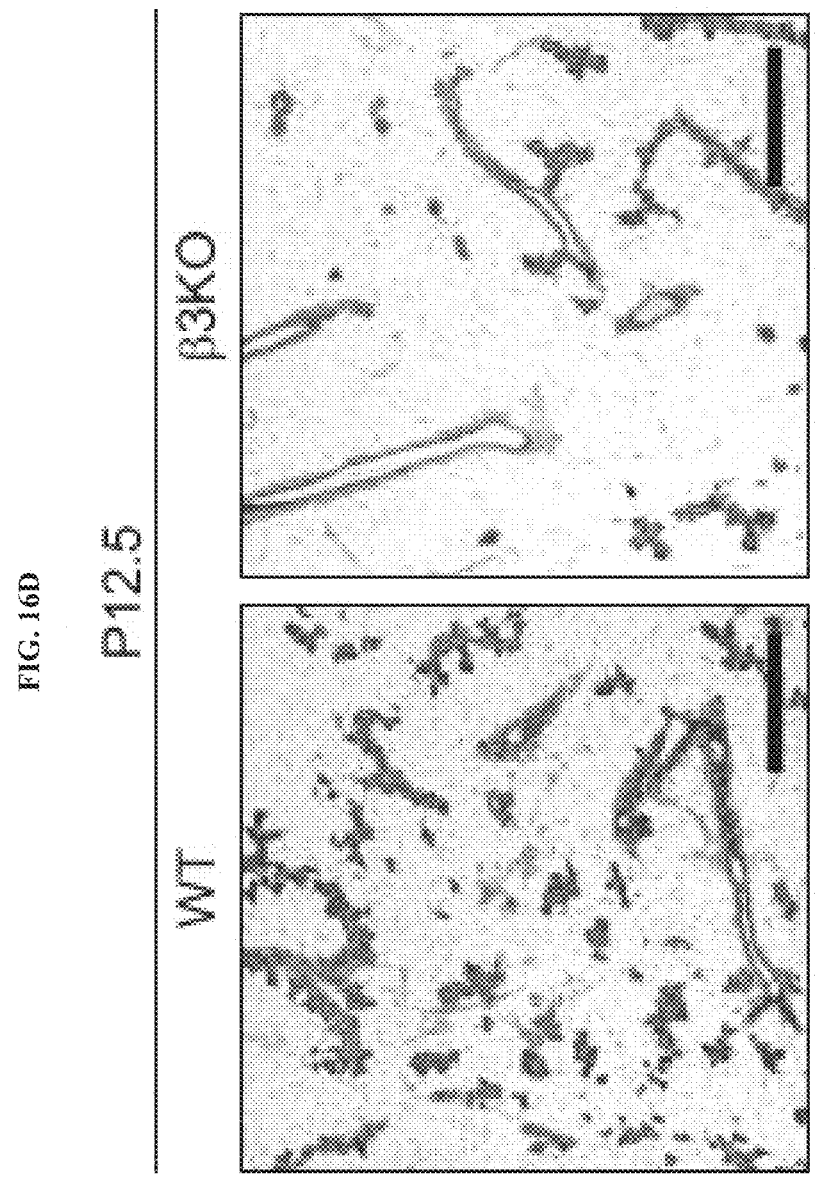

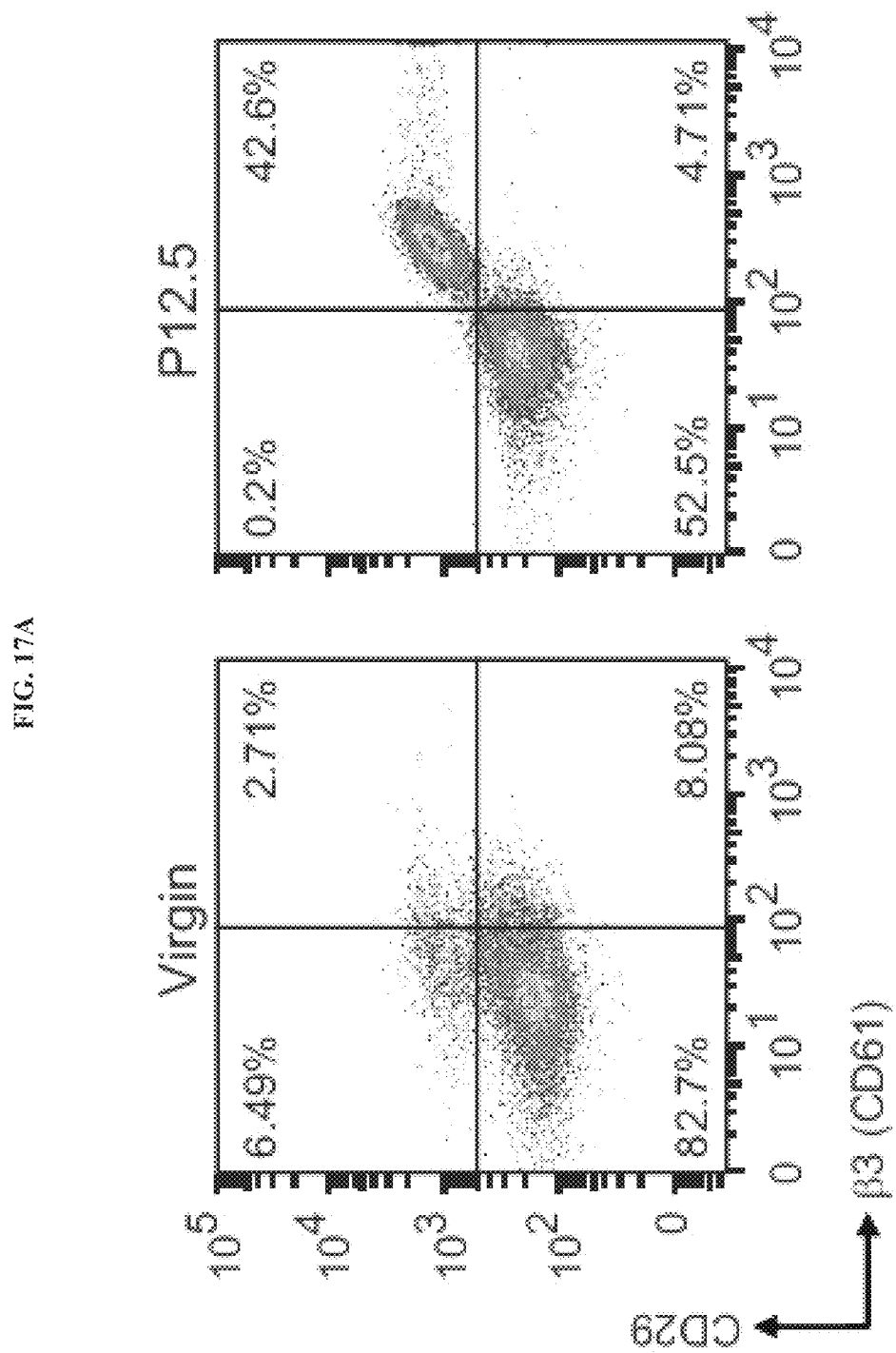

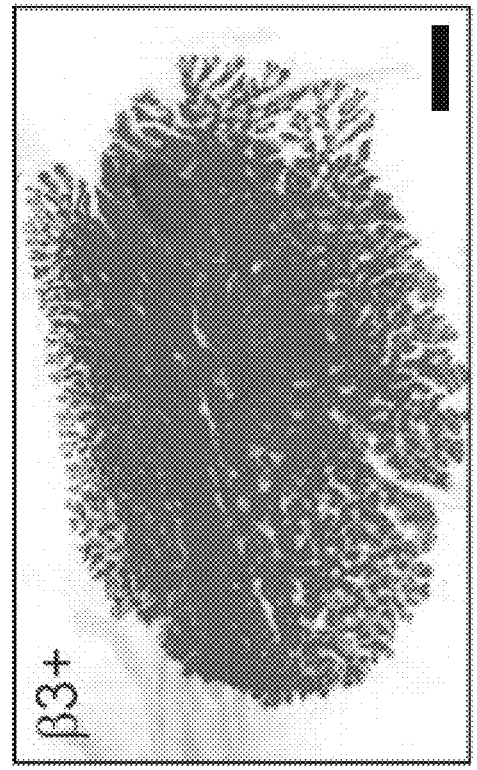
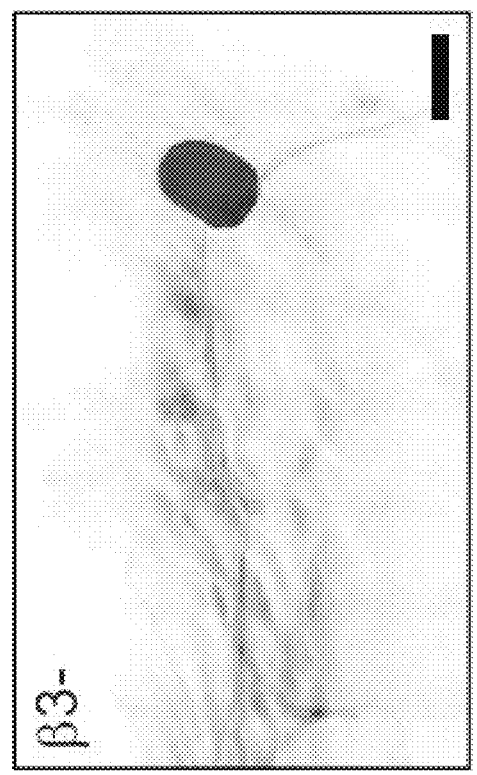
FIG. 17F

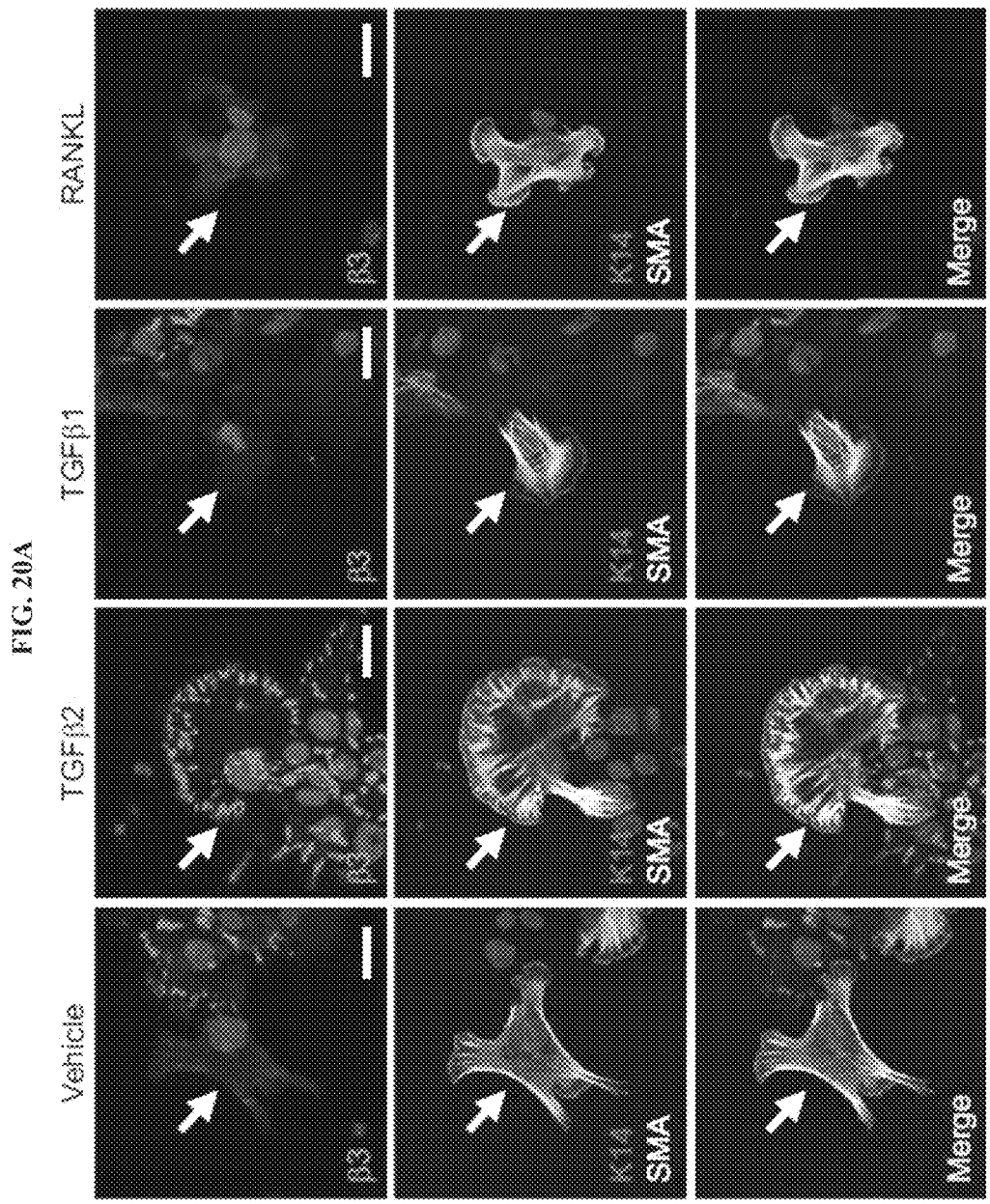

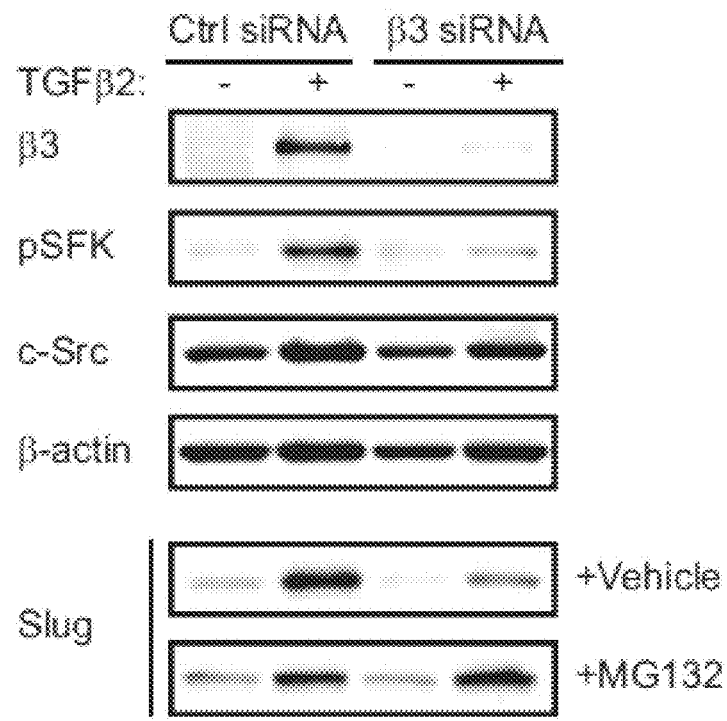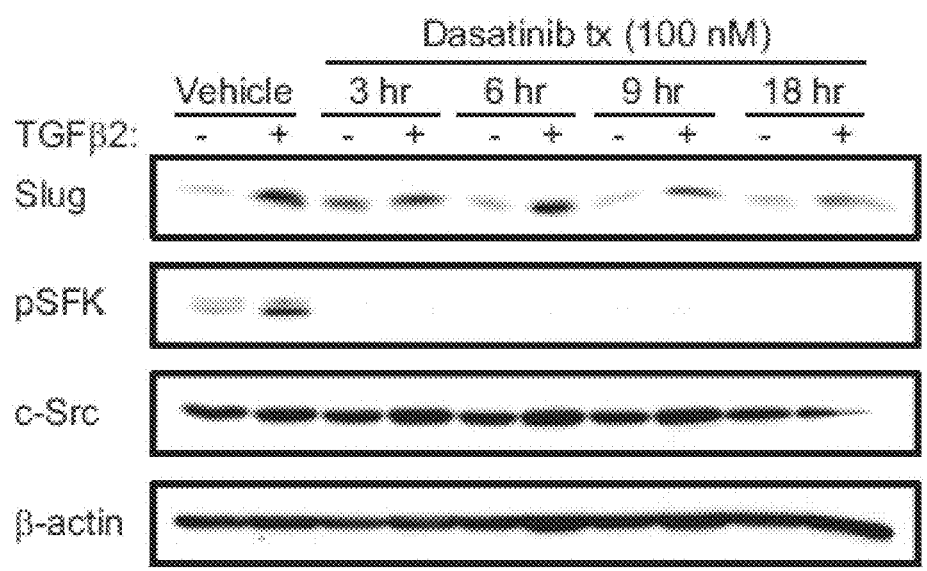

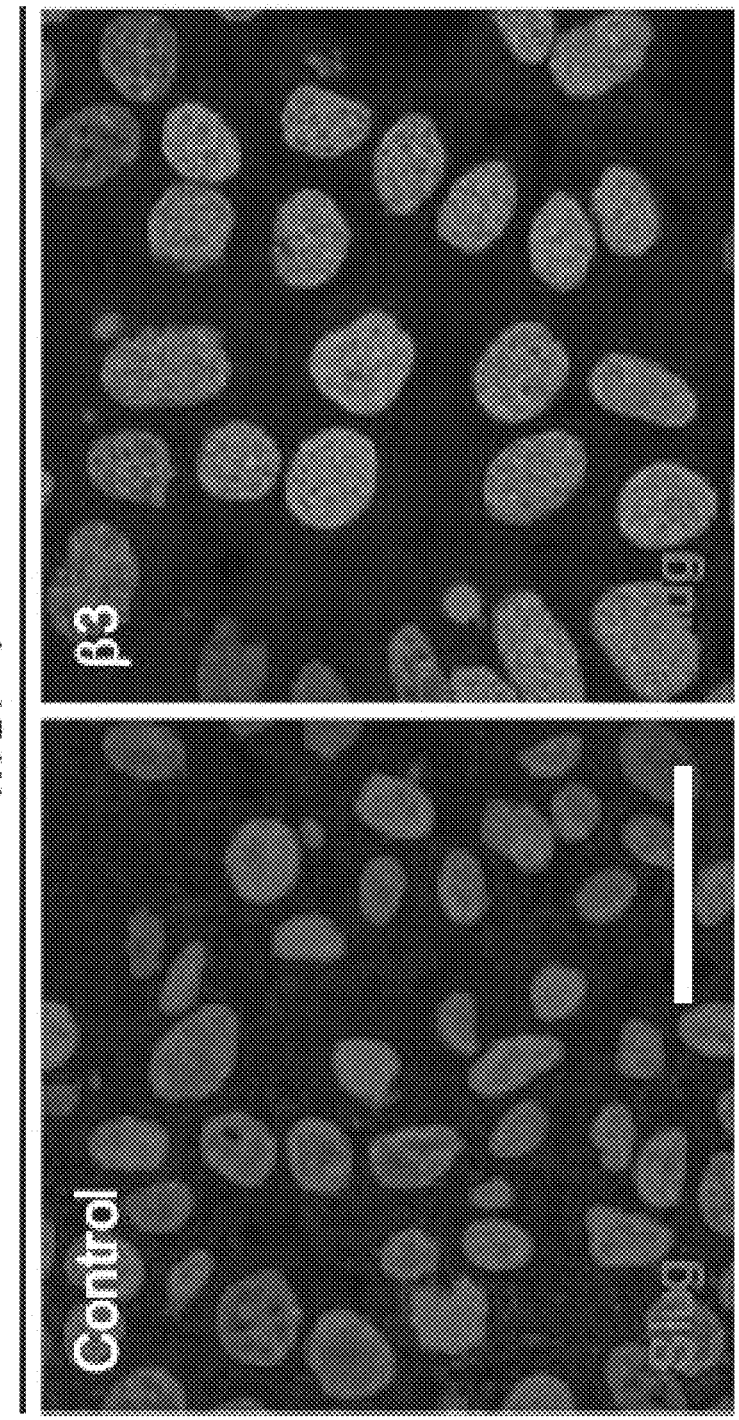
FIG. 22A MCF-7

| Number of cells injected | Tumor Incidence | |
|---|---|---|
| | shCtrl | shβ3 |
| 100,000 | 4/4 | 4/4 |
| 10,000 | 4/4 | 4/4 |
| 1000 | 4/6 | 0/6 |
| 100 | 1/6 | 0/6 |
| Frequency 95% Confidence Interval | 1/831 (1/327-1/2115) | 1/5116 (1/1847-1/14,175) |
| $P = 0.0172$ | | |

COMPOSITIONS AND METHODS FOR IDENTIFYING ANTI CANCER, ANTI-METASTATIC AND ANTI-STRESS AGENTS

RELATED APPLICATIONS

This application is a divisional of U.S. application Ser. No. 15/074,523, filed: Mar. 18, 2016, which claims the benefit of priority under 35 U.S.C. § 119(e) of U.S. Provisional Patent Application Ser. No. ("USSN") 62/135,044, filed Mar. 18, 2015. The aforementioned applications are expressly incorporated herein by reference in their entirety and for all purposes.

TECHNICAL FIELD

This invention generally relates to medicine and drug screening. In alternative embodiments, provided are products of manufacture, such as assays and nucleic acid constructs, recombinant cells, and methods, comprising use of beta3-integrin (β3-integrin, or ITGB3) promoters operatively linked to a reporter, for drug screening, and in particular, screening for agents that inhibit cancer cell survival and metastasis. In alternative embodiments, compositions and methods as provided herein also can be used to identifying novel pathways that lead to acquired resistance, stemness, and anchorage independent growth; and characterizing distinct populations of cancer cells within a tumor microenvironment.

BACKGROUND

The beta3-integrin (ITGB3) protein product is the integrin beta chain beta 3 (β3). Integrins are integral cell-surface proteins composed of an alpha chain and a beta chain. A given chain may combine with multiple partners resulting in different integrins. Integrins are known to participate in cell adhesion and cell-surface mediated signaling.

The adhesion receptor integrin alpha v beta 3 (αvβ3) contributes to tumor cell functions that are potentially involved in cancer growth and metastasis. For example, it has been suggested that expression of integrin alpha v beta 3 promotes the metastatic phenotype in human melanoma by supporting specific adhesive, invasive and migratory properties of the tumor cells.

SUMMARY

In alternative embodiments, provided are a nucleic acid construct, a chimeric nucleic acid, or a recombinant nucleic acid, comprising:

(a) a beta3-integrin (ITGB3) promoter, or a functional subsequence thereof; and (b) a reporter nucleic acid, or a nucleic acid encoding a reporter or a marker protein or compound, wherein optionally the reporter or marker protein or compound is a bioluminescent or a fluorescent protein or compound, or a luciferase or a green fluorescent protein (GFP), and optionally the nucleic acid construct, chimeric nucleic acid, or recombinant nucleic acid further comprises an ITGB3 distal promoter and/or enhancer, or SEQ ID NO:2, or a subsequence of SEQ ID NO:2 (FIG. 5) that can function as an ITGB3 distal promoter and/or enhancer.

In alternative embodiments, the beta3-integrin (ITGB3) promoter, or functional subsequence thereof comprises all, substantially all or a portion of a human beta3-integrin (ITGB3) promoter, or a functional subsequence thereof.

In alternative embodiments, the nucleic acid construct, chimeric nucleic acid, or the recombinant nucleic acid, further comprise, or are contained in, an expression cassette, a vector, a plasmid, a phagemid or an artificial chromosome.

In alternative embodiments, provided are an expression cassette, a vector, a plasmid, a phagemid or an artificial chromosome comprising or having contained within a nucleic acid construct, chimeric nucleic acid, or recombinant nucleic acid as provided herein.

In alternative embodiments, provided are a recombinant or an engineered cell or cell line comprising a nucleic acid construct, chimeric nucleic acid, or a recombinant nucleic acid as provided herein, or an expression cassette, a vector, a plasmid, a phagemid or an artificial chromosome as provided herein, wherein optionally the cell is a beta3-integrin negative cell, or a cell unable to express a functional amount of a homologous beta3-integrin, and optionally the beta3-integrin negative cell is a beta3-integrin knockout cell, and optionally the nucleic acid construct or the chimeric or recombinant nucleic acid, or the expression cassette, vector, plasmid, phagemid or artificial chromosome are stably integrated into the cell's chromosome, or are stably episomally expressed, and optionally the cell is a cancer cell or a cancer cell line, or a carcinoma cell line or an immortalized cell line.

In alternative embodiments, provided are a non-human transgenic organism (e.g., animal) comprising the recombinant or the engineered cell as provided herein; or, a nucleic acid construct or a chimeric or recombinant nucleic acid as provided herein.

In alternative embodiments, provided are methods for identifying or screening for an agent or a compound:

which inhibits beta3-integrin (ITGB3) promoter-driven integrin beta-3 (ITGB3) expression and phenotypes resulting from ITGB3 upregulation, that inhibits, negatively affects or decreases cancer cell survival;

that inhibits or decreases the amount of metastasis or circulating tumor cells, or patient derived xenografts (PDX);

that reverses cancer cell acquired resistance to a drug;

that reverses stemness;

that inhibits Slug activation, tumorsphere formation and tumor initiation in human breast cancer cells; and/or that inhibits, negatively affects or decreases anchorage independent growth of a cancer cell, comprising:

(a) providing a test compound, wherein optionally the test compound comprises or is a biologic, a drug, a small molecule or a small molecule drug, a bio-molecule, a protein, a lipid, a polysaccharide, or a nucleic acid;

(b) providing a recombinant or an engineered cell, or a cell free expression system, or a non-human transgenic organism, comprising a nucleic acid construct, or a chimeric or recombinant nucleic acid as provided herein, or an expression cassette, a vector, a plasmid, a phagemid or an artificial chromosome as provided herein, wherein the beta3-integrin (ITGB3) promoter or the functional subsequence thereof expresses the reporter nucleic acid, or the reporter or marker protein, and optionally the beta3-integrin (ITGB3) promoter or the functional subsequence thereof is constitutively active and the reporter nucleic acid, or the reporter or marker protein is constitutively expressed, and optionally the beta3-integrin (ITGB3) promoter or the functional subsequence thereof is inducibly expressed resulting in inducible expression of the reporter nucleic acid, or the reporter or marker protein, and optionally the beta3-integrin (ITGB3) promoter or the functional subsequence thereof is inducibly expressed by addition of a chemical or a drug, such as an erlotinib, or a conditioned media, such as a conditioned media from serum deprived cells or cancer cells;

(c) administering to or contacting the test compound with the recombinant or engineered cell, or to the cell free expression system, or a non-human transgenic organism, and measuring or determining the level of the reporter nucleic acid, or the reporter or marker protein, wherein measuring or determining an increase in the level of the reporter nucleic acid, or the reporter or marker protein indicates that the test compound is an beta3-integrin (ITGB3) promoter inducer, and wherein measuring or determining a decrease in the level of the reporter nucleic acid, or the reporter or marker protein indicates that the test compound is an beta3-integrin (ITGB3) promoter inhibitor, and optionally also a compound that can:

inhibit, negatively affect or decrease cancer cell survival;
inhibit or decrease the amount of metastasis;
reverse cancer cell acquired resistance to a drug;
reverse stemness;
that inhibits Slug activation and tumor initiation in human breast cancer cells; and/or
inhibit, negatively affect or decrease anchorage independent growth of a cancer cell.

In alternative embodiments, provided are methods further comprising administering a negative control and/or a positive control compound known to not affect beta3-integrin (ITGB3) promoter activity.

All publications, patents, patent applications cited herein are hereby expressly incorporated by reference for all purposes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings set forth herein are illustrative of embodiments as provided herein and are not meant to limit the scope of the invention as encompassed by the claims.

FIG. 1A illustrates a schematic of the design of the study, where ITGβ3 expression after serum starvation (0.1% bovine serum albumin, BSA, in three-dimensional (3D) culture) of non-labeled ITGβ3 negative and labeled ITGβ3 positive cells, is analyzed by FACS analysis; FIG. 1B graphically illustrates this data as analyzed by cell sorter, and FIG. 1C graphically illustrates cell viability with (10%) and without serum and with or without ITGβ3 (CD61 is the cluster of differentiation, or CD, designation for ITGβ3).

FIG. 2A illustrates a schematic of the design of the study, where cells are analyzed for ITGβ3 expression after nutrient deprivation when grown in 10% fetal bovine serum (FBS) growth medium, 0.1% BSA, or conditioned media (CM); FIG. 2B graphically illustrates change in β3 promoter expression by detecting luciferase under conditions with and without 0.1% BSA, or conditioned media (CM); and FIG. 2C graphically illustrates ITGβ3 expression in the immortalized beta3 negative cell line HCC827, in 0.1% BSA, or conditioned media (CM), using constructs with and without a β3 promoter.

FIG. 3A illustrates a schematic of the design of the study, where erlotinib-resistant tumors (the immortalized beta3 negative lung cancer cell line HCC827) are created in mice, tumor cells isolated (including erlotinib-sensitive and acquired erlotinib-resistant cells), and ITGβ3 is expressed using stable reporter constructs; FIG. 3B graphically illustrates tumor volume as a function of days in cells exposed to erlotinib or vehicle, where cells exposed to erlotinib acquired resistance, and cells exposed to vehicle were erlotinib sensitive.

FIG. 4A graphically illustrates fold change ITGβ3 mRNA relative to the immortalized beta3 negative cell line HCC827 as compared to resistant clones as indicated in the figure, and FIG. 4B shows fold change relative luminescence units (RLU) in immortalized beta3 negative cell line HCC827 as compared to resistant clone HCC827P, the RLUs indicating expression of luciferase, and the β3-promoter active as indicated by luciferase expression from the β3-promoter construct.

FIG. 5 illustrates an exemplary nucleic acid sequence (SEQ ID NO:2) of a distal regulatory region of ITGβ3, a 15 kb to 10 kb upstream of ITGB3 start site, that can be used to practice embodiments as provided herein.

FIG. 9A illustrates a schematic of the design of the study, where ITGβ3 expression by a β3-promoter luciferase expressing construct after 48 to 72 hours of induction of the cell by either: growth media (GM), serum-depleted media (SDM), and conditioned media (CM), is analyzed by FACS analysis; FIG. 9B graphically illustrates data of relative luminescence units (RLU) showing that the β3-promoter and the luciferase expression is induced by SDM and CM; and FIG. 9C graphically illustrates data showing the fold change of ITGβ3 mRNA as induced by GM, SDM and CM.

FIGS. 11A-B illustrate data showing the generation of β3-reporter cell lines having acquired Tyrosine Kinase Inhibitor (TKI) drug, or erlotinib, resistance: FIG. 11A illustrates a schematic of the design of the study, where erlotinib-resistant tumors (the immortalized beta3 negative lung cancer cell line HCC827) are created in mice, tumor cells isolated (including erlotinib-sensitive and acquired erlotinib-resistant cells), and cells having acquired erlotinib resistance having a stable reporter construct are generated; FIG. 11B graphically illustrates tumor volume as a function of days in cells exposed to erlotinib or vehicle, where cells exposed to erlotinib acquired resistance, and cells exposed to vehicle were erlotinib (growth factor) sensitive.

FIG. 12A schematically illustrates the design of this exemplary study, where a β3-promoter luciferase expressing construct is placed into lung cancer cell lines HCC827P (erlotinib sensitive) and HCC827R18 (erlotinib resistant); FIG. 12B graphically shows fold change in mRNA in various erlotinib resistant cell lines as compared to the erlotinib sensitive HCC827P; and FIG. 12B graphically shows fold change in relative luminescence units (RLU) in resistant cells versus sensitive cells as indicated by luciferase expression from the β3-promoter construct.

FIG. 13 lists cells lines used for screens to identify agents that inhibit drug resistance, stemness and metastasis; and FIG. 14 lists cell lines used for screens to identify soluble factors.

FIG. 15A schematically illustrates the protocol scheme of this study, where a stable β3-negative erlotinib-sensitive lung adenocarcinoma cell line HCC827 (the so-called "sensitive cells") was exposed to erlotinib for 12 weeks to generate erlotinib-resistant cells, then these erlotinib-resistant cells were given a 2 week "holiday" from erlotinib to generate erlotinib-sensitive cells (these are the so-called "holiday cells"), which then were again exposed to erlotinib for 72 hours to generate, or re-generate, erlotinib-resistant cells (the so-called "resume cells"); FIG. 15B graphically illustrates β3-promoter activity as RLU units (indicating promoter luciferase activity) in β3-negative erlotinib-sensitive cells, erlotinib-resistant cells, erlotinib-holiday cells, and erlotinib-resume cells, as illustrated in FIG. 15C; FIG. 15C graphically illustrates data showing expression of cell surface ITGB3 expression in untreated, erlotinib-resistant and erlotinib-holiday cells; FIG. 15D illustrates Northern blots showing levels of expressed ITGB3, OCT4, NANOG, and β-actin protein with and without erlotinib in erlotinib-resistant and erlotinib-holiday cells; as further described in Example 1, below.

FIGS. 16A-F illustrate representative images of β3 immunohistochemistry in an adult virgin murine mammary gland. FIG. 16A illustrates images of is an example of a duct (left panel) with areas in boxes shown at high power (right panels); Images on right show β3-expressing cells (arrows) in the basal epithelial cell layer (top, right) and a subset of luminal epithelial cells (bottom, right). Scale bars, 50 mm (left panel) and 10 mm (right panels).

FIG. 16B illustrates an image of a Western blot of whole-mammary gland lysates for β3 and a-SMA (loading control). n=3 mice for each stage.

FIG. 16C illustrates Mammary gland whole mounts from virgin and P12.5 WT and β3KO mice. Virgin, WT (n=8) and b3KO (n=7); P12.5, WT (n=19) and β3KO (n=10). Scale bars, 5 mm (low magnification) and 500 mm (high magnification).

FIG. 16D illustrates a representative H&E-stained sections from WT and β3KO P12.5 mammary glands. Scale bars, 500 mm.

FIG. 16E illustrates Quantitation of duct/alveoli density in P12.5 WT versus β3KO H&E-stained mammary gland sections (WT, n=13; b3KO, n=10; p=0.015).

FIG. 16F illustrates qPCR results displaying the relative amount of GATA-3 and ELF5 mRNA in WT and β3KO P12.5 mammary glands (WT, n=11; β3KO, n=9). Each sample was run in triplicate, and glyceraldehyde 3-phosphate dehydrogenase was used as a loading control. Data are displayed as the mean±SD. Fold change ($2^{-DDCT}$) in β3KO glands is relative to WT.

FIG. 17A illustrates a representative FACS density plots showing the live, Lin_CD24+ cells expressed according to their CD29 (b1 integrin) and β3 status.

FIGS. 17F-H illustrate Mammary gland outgrowth experiments:

FIG. 17F illustrates a representative images of carmine-stained mammary gland outgrowth whole mounts from P12.5 Lin_CD24+β3+ and β3 donor cells. Recipients were harvested at lactating day 2. Scale bars, 2 mm.

FIG. 17G illustrates a Bar graph showing the frequency of successful mammary gland outgrowths from 10,000 Lin_CD24+β3+ and β3 donor cells from P12.5 mice.

FIG. 17H illustrates a Representative image of immunohistochemical staining for E-cadherin (brown) and aSMA (red) in sections from Lin_CD24+β3+ cell outgrowths.

FIG. 18A shows representative FACS density plots of WT and b3KO P12.5 mammary cells showing the live, Lin_cells expressed according to their CD24 and CD29 status;

Figure 18A:
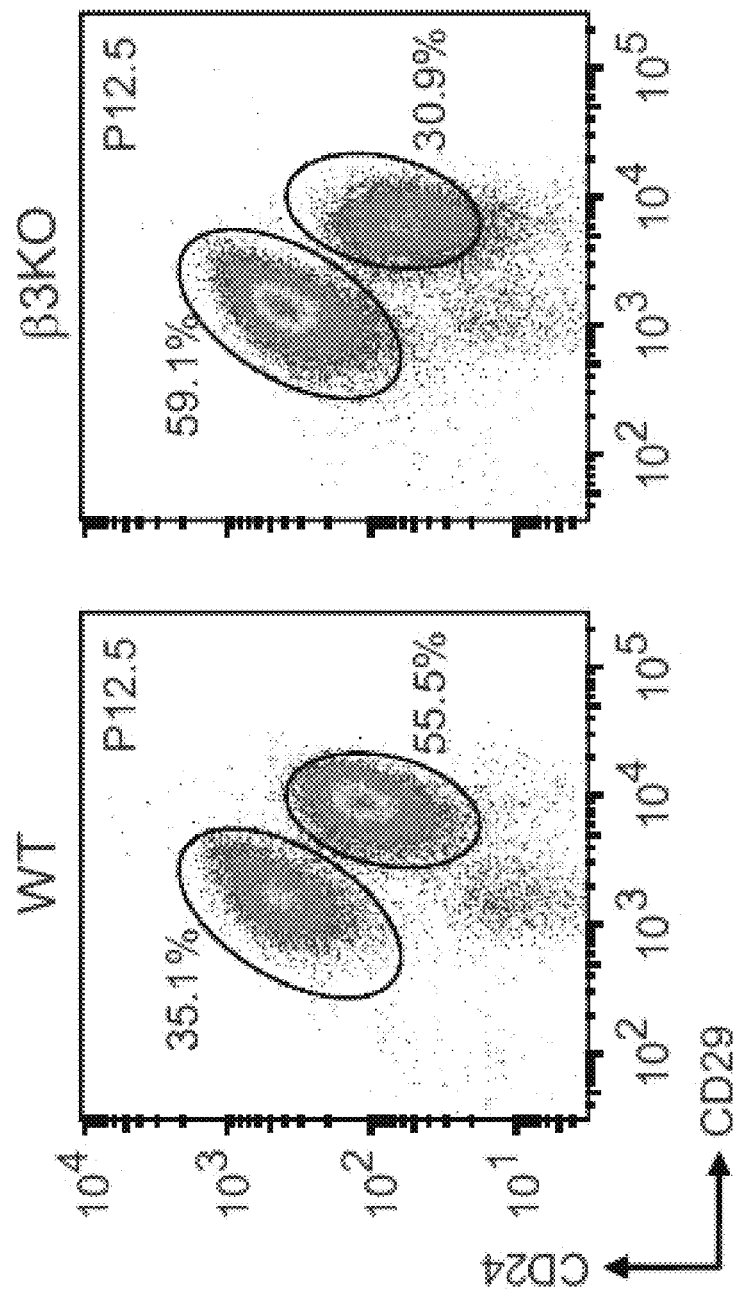
FIG. 18A illustrates an image of data from a FACS analysis of WT and b3KO virgin and P12.5 mammary glands.
Figure 18B:
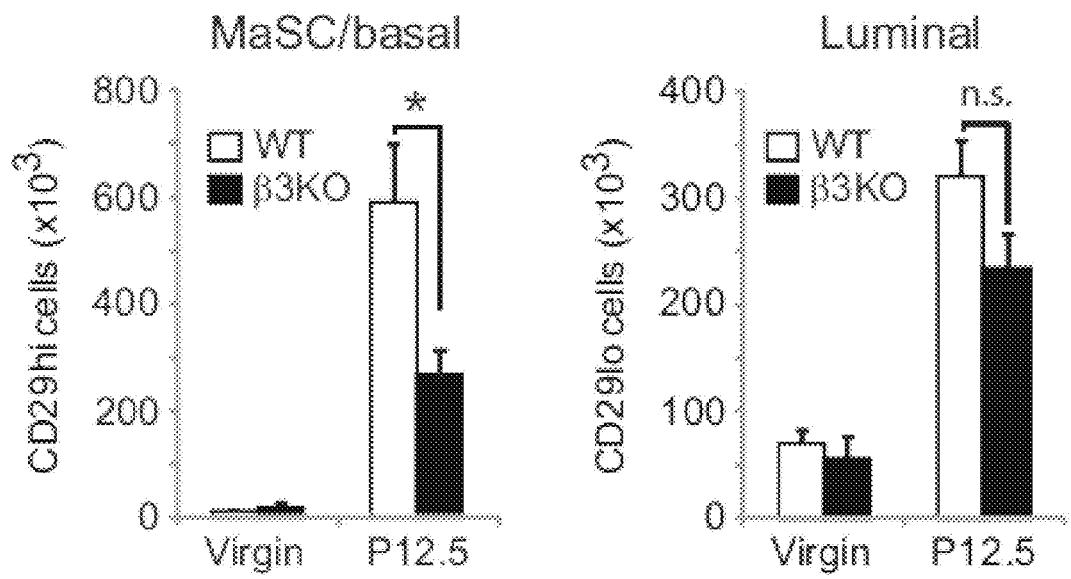
FIG. 18B graphically illustrates the quantitation of the data of FIG. 18A, or the total number of FACS live Lin_CD24+CD29hi and CD29lo cells from virgin and P12.5 mammary glands.
Figure 18C:
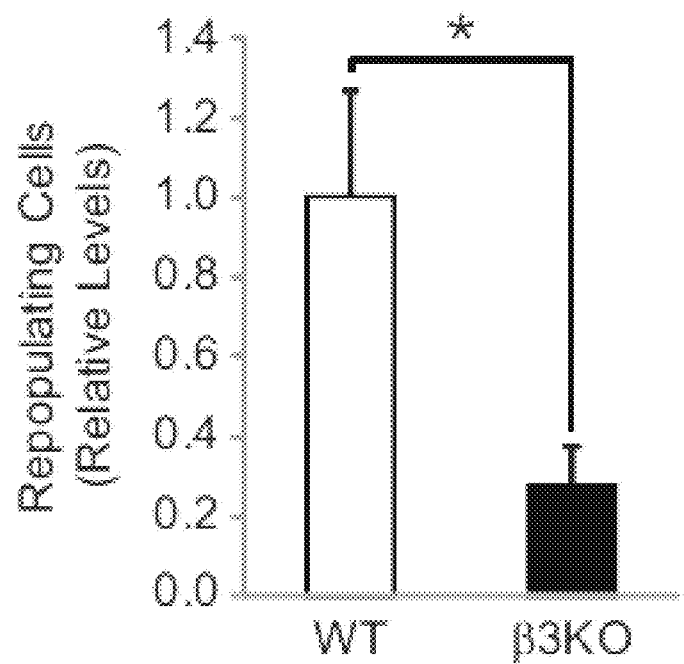
FIG. 18C graphically illustrates a histogram showing the relative levels of total repopulating cells in the CD29hi pool from WT and β3KO P12.5 donor mice.

For FIG. 18B and FIG. 18C, data represent the mean±SEM, and statistical analysis was performed by Student's t tests. *p<0.05. (B) n.s., not significant (p>0.05).

Figure 18D:
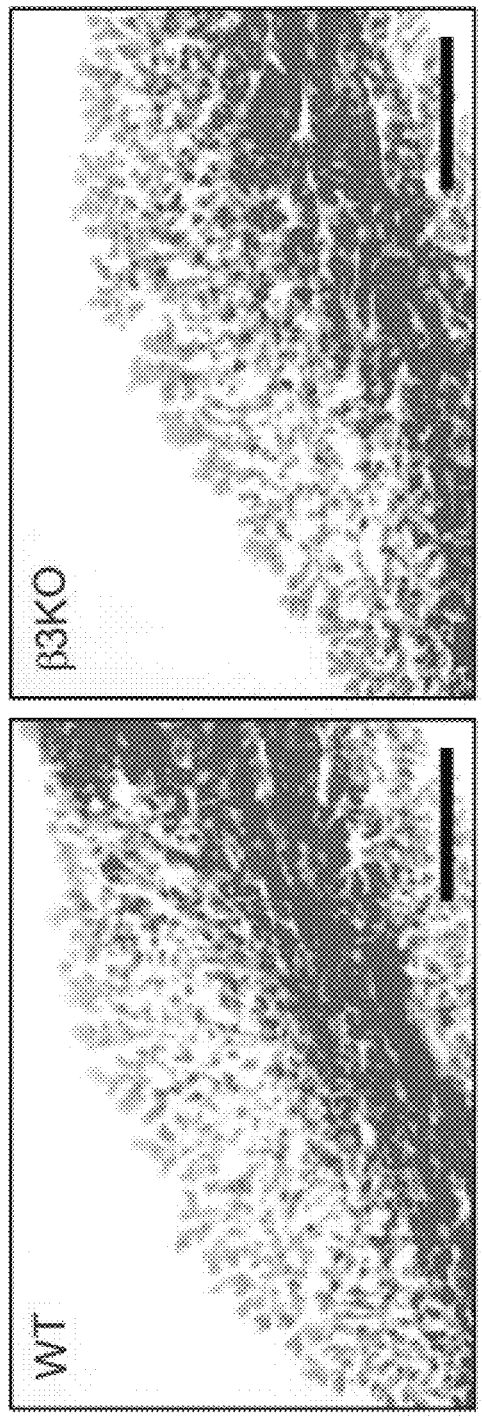

FIG. 18D illustrates representative images of carmine-stained WT and b3KO outgrowths harvested at lactating day 2.

Figure 19A:
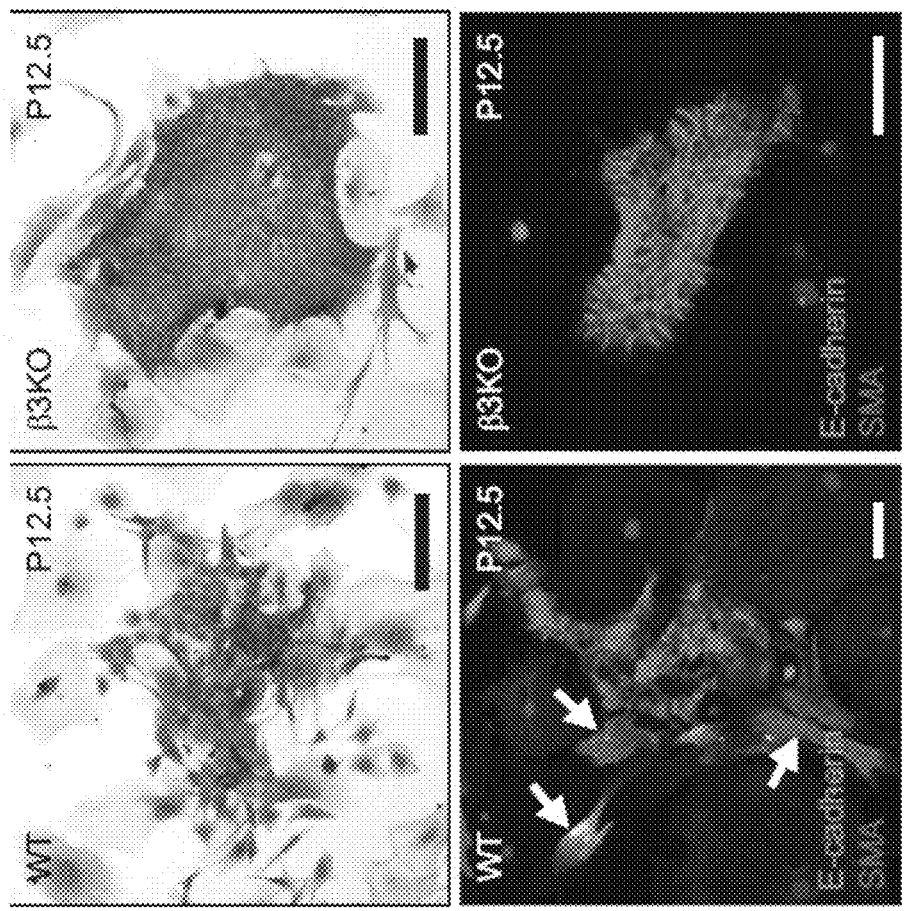

FIG. 19A illustrates Representative images of WT and β3KO P12.5 colony morphology on irradiated fibroblasts by crystal violet staining (top panels) or immunofluorescent staining for E-cadherin and SMA (bottom panels). Nuclei are stained blue in all panels. Arrows mark SMA-positive cells. Scale bars, 100 mm.

Figure 19B:
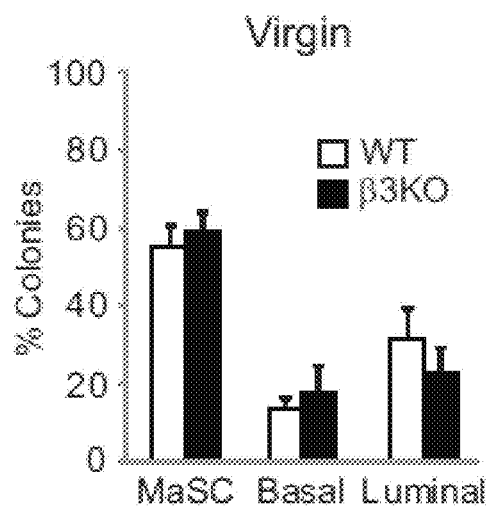
Figure 19C:
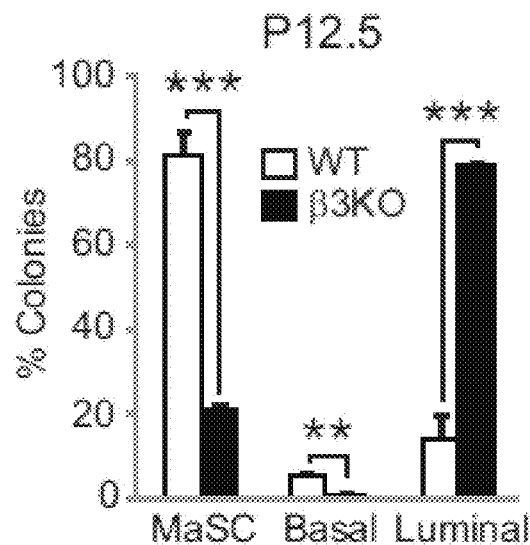
Figure 19D:
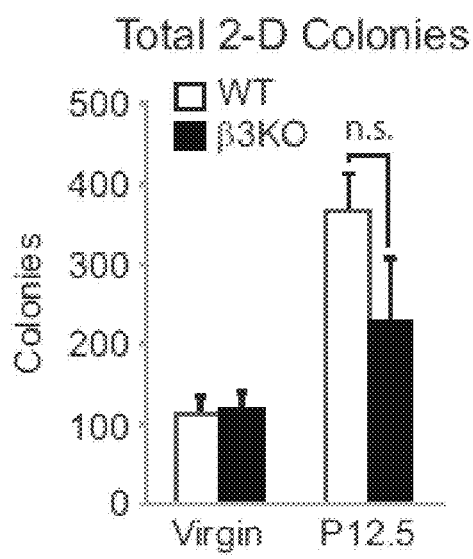

FIGS. 19B-D graphically illustrate quantitation of the percent MaSC, basal, and luminal colonies (FIG. 19B and FIG. 19C) and total colony number (FIG. 19D) from virgin and P12.5WT and β3KO mice. Virgin, WT (n=6) and β3KO (n=6); P12.5, WT (n=5) and β3KO (n=4).

Figure 19E:
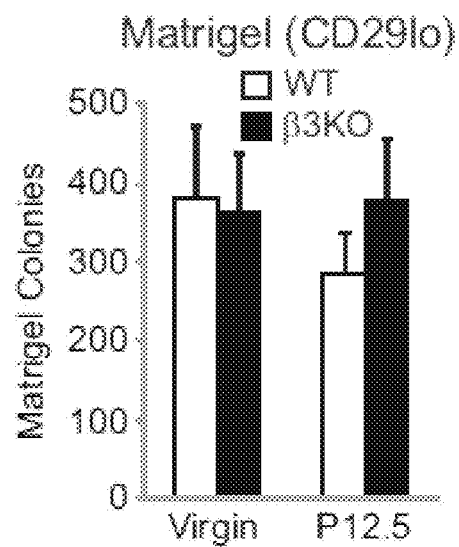

FIG. 19E graphically illustrates a histogram depicting colony formation in Matrigel from FACS CD29lo WT and β3KO cells from virgin and P12.5 mice.

Figure 19F:
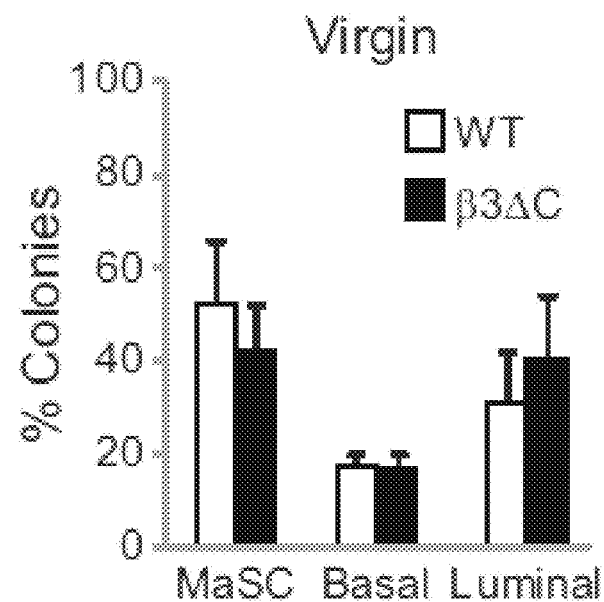
Figure 19G:
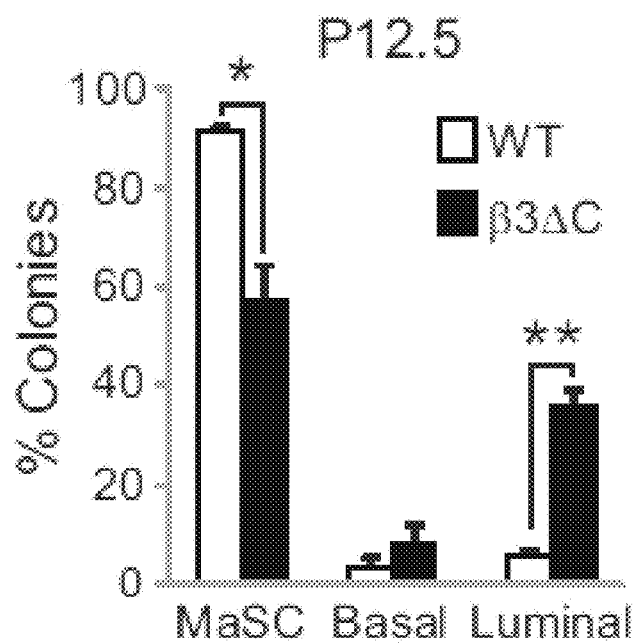

FIGS. 19F-G graphically illustrate data showing that MaSC, basal, and luminal colonies formed from virgin (19F) or P12.5 (19G) WT and β3DC mammary cells grown on irradiated MEFs.

Figure 19H:
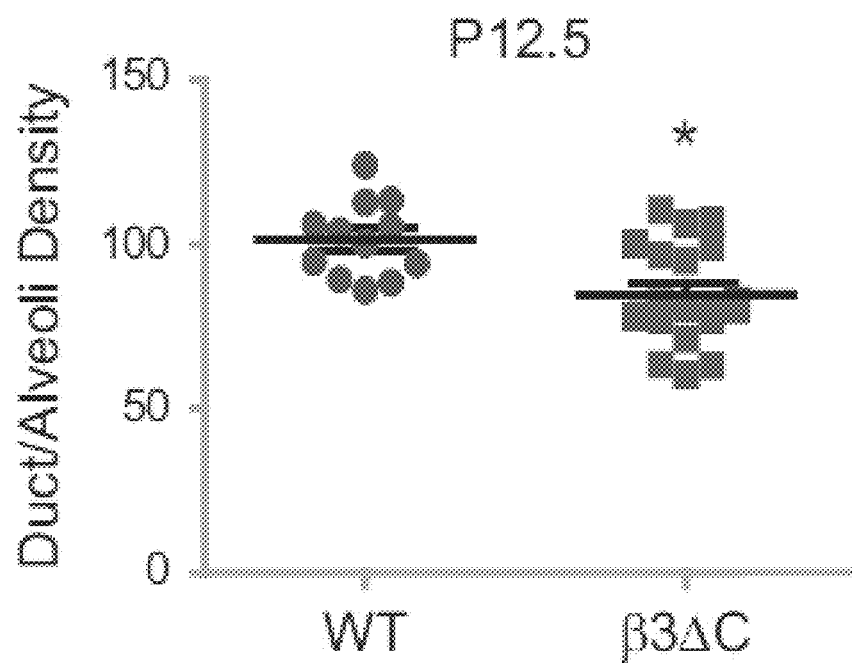

FIG. 19H graphically illustrates quantitation of duct/alveoli density in P12.5 WT versus β3DC H&E-stained mammary gland sections.

FIG. 20A illustrates representative immunofluorescent images of β3 expression in K14+SMA+ cells (arrows) from pooled virgin WT mammary cells stimulated with the indicated growth factors. Nuclei are stained blue in all panels. Scale bars, 20 mm. Data shown are representative of three independent experiments.

Figure 20B:
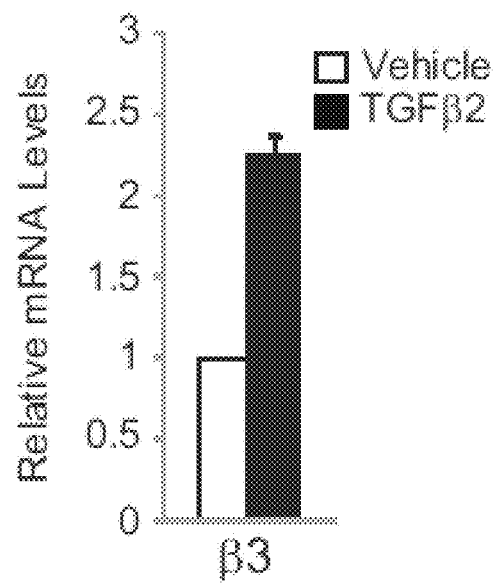
Figure 20C:
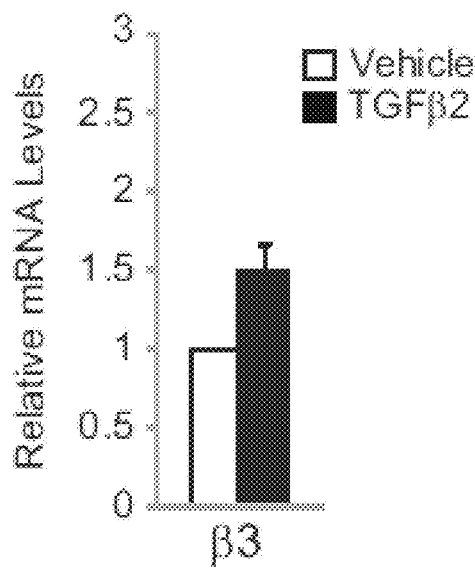

FIGS. 20B-C graphically illustrate qPCR analysis comparing the relative levels of β3 mRNA in vehicle versus TGF-β2-stimulated CD29hi (FIG. 20B) and CD29lo (FIG. 20C) cells from WT virgin mice. n=2 independent experiments (pooled samples).

Figure 20D:
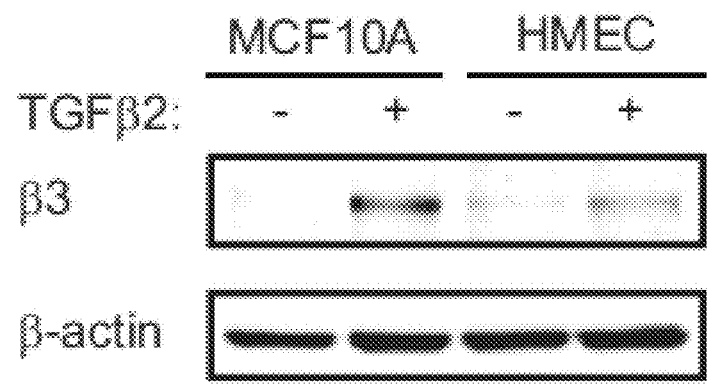

FIG. 20D illustrates an image of an Immunoblot for β3 and b-actin (loading control) in MCF10As and HMECs stimulated with TGF-b2 or vehicle control.

Figure 20E:
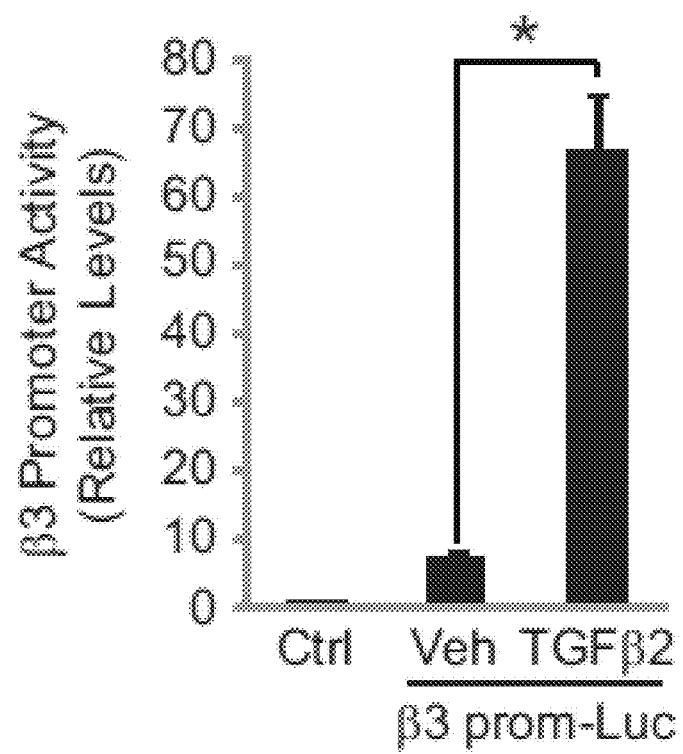

FIG. 20E graphically illustrates a Histogram displaying the relative luciferase activity in MCF10A cells transfected with an empty vector (Ctrl) or a luciferase reporter plasmid containing the proximal region of the β3 promoter (β3 prom-Luc) and stimulated with vehicle or TGF-β2. n=3 independent experiments. p=0.043.

Figure 20F:
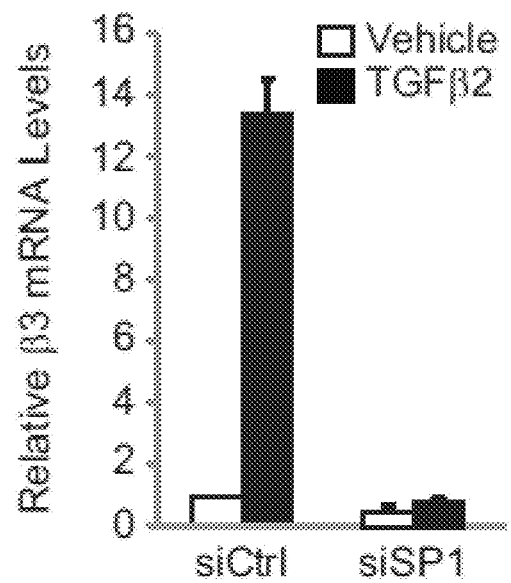
Figure 20G:
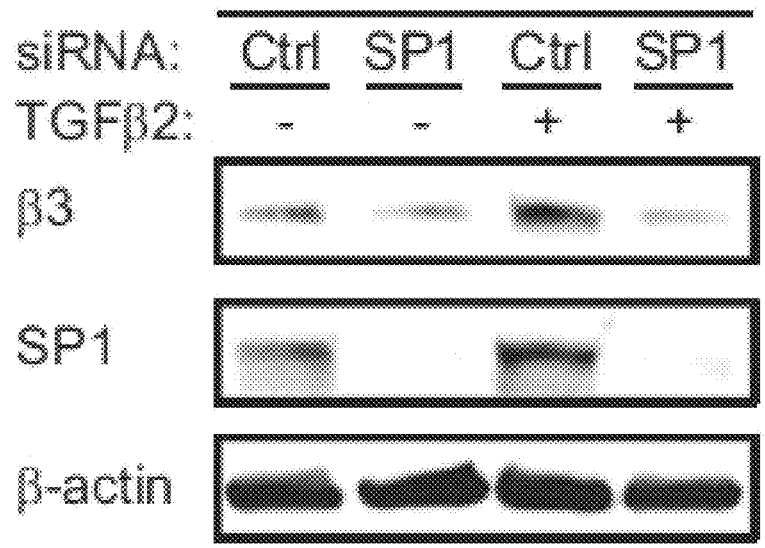

FIG. 20F graphically illustrates data of and FIG. 20G illustrates an image of a representative experiment showing the effect of SP1 knockdown on β3 mRNA (FIG. 20F) and protein (FIG. 20G) expression in MCF10A cells stimulated with TGF-β2 or vehicle control.

Figure 20H:
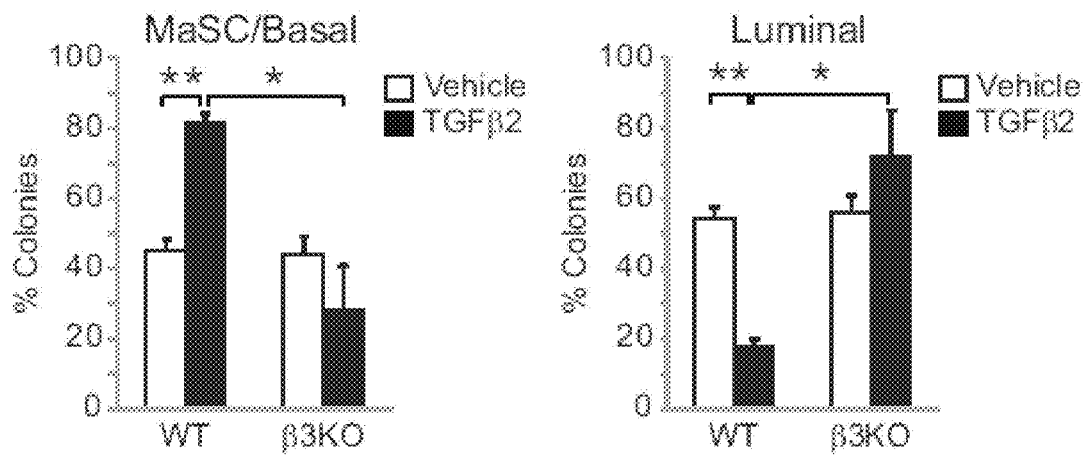
Figure 20I:
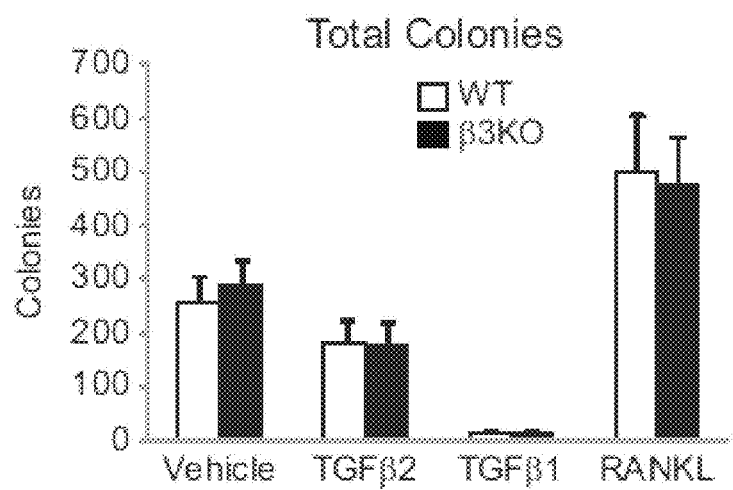

FIG. 20H-I graphically illustrate quantitation of the percent MaSC/basal and luminal colonies (FIG. 20H) and total colony number (FIG. 20I) from pooled virgin WT and b3KO mammary cells stimulated with the indicated growth factors. n=3 independent experiments. FIG. 20H: p values for vehicle versus TGF-b2 in WT cells are as follows: MaSC, p=0.0071; Luminal, p=0.0071. p values for WI versus b3KO cells stimulated with TGF-b2 are as follows: MaSC, p=0.0413; Lumina', p=0.0413. FIG. 20E, FIG. 20H, and FIG. 20I graphically illustrates data representing the mean±SEM, and statistical analysis was performed by Student's t tests. *p<0.05; **p<0.01.

Figure 21A:
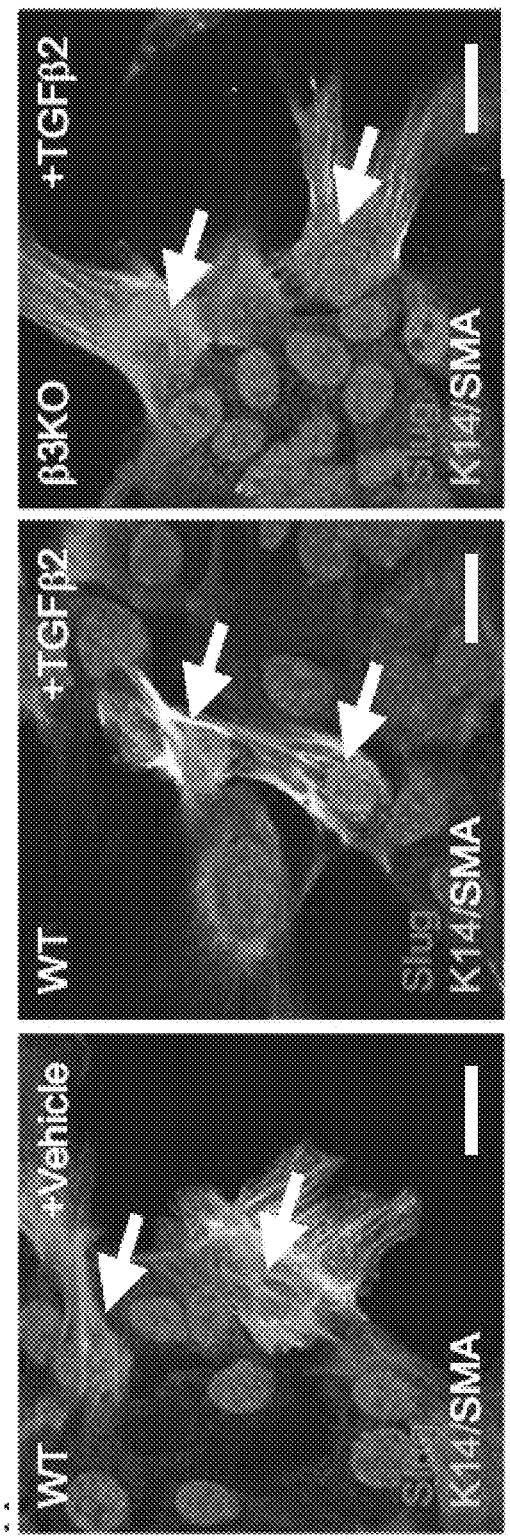
Figure 21B:
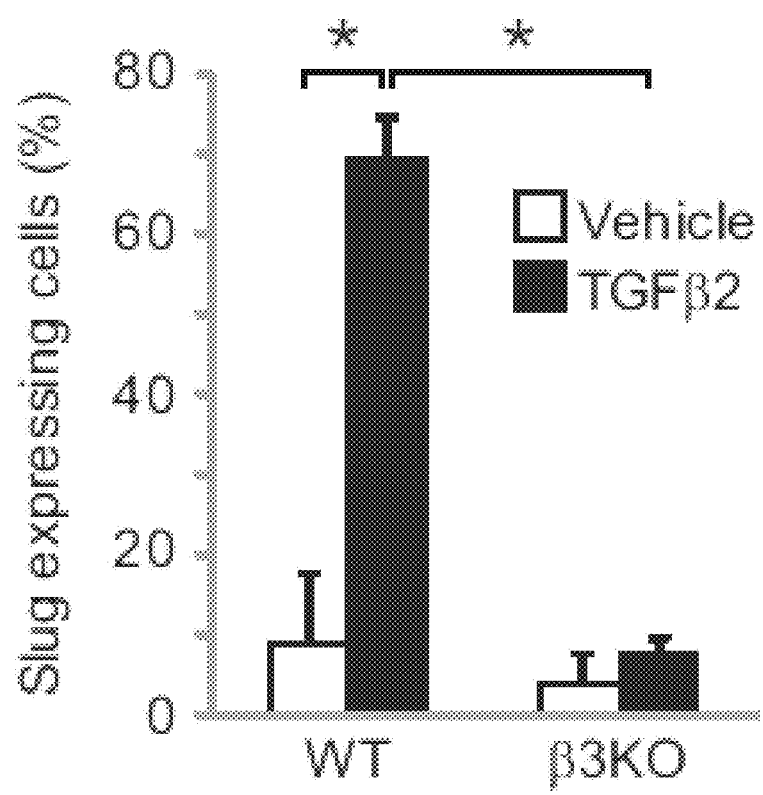

FIG. 21A illustrates images and FIG. 21B graphically illustrates data showing Slug expression in K14+SMA+ cells from virgin WT and b3KO mammary cells stimulated with vehicle or TGF-β2.

FIG. 21A illustrates representative images of Slug expression in K14+SMA+ cells (arrows). Scale bars, 20 mm.

FIG. 21B graphically illustrates quantitation of the percentage of Slug+K14+SMA+ cells. p=0.0439 (vehicle versus TGF-b2 inWT cells) and p=0.0342 (WT versus b3KO cells stimulated with TGF-b2).

Figure 21C:
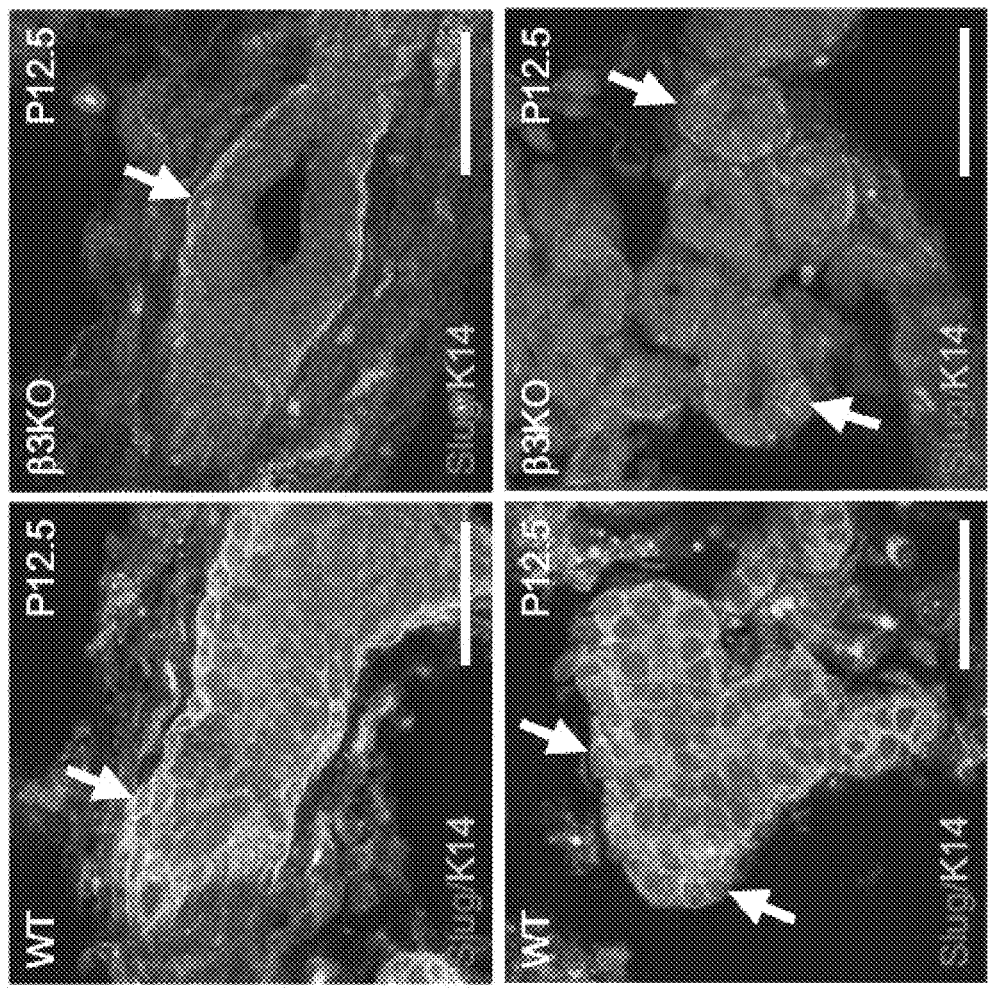
Figure 21D:
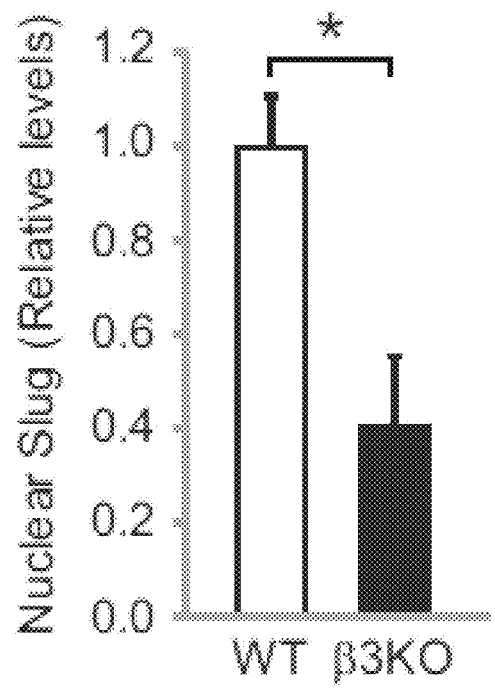

FIG. 21C illustrates images and FIG. 21D graphically illustrates data showing Slug expression in WT and b3KO P12.5 mammary glands.

FIG. 21C illustrates representative images of Slug in K14+ cells (arrows). Scale bars, 20 mm. (A and C) Nuclei are stained blue in all panels.

FIG. 21D graphically illustrates a Histogram showing the relative levels of nuclear Slug expression.

Figure 21E:
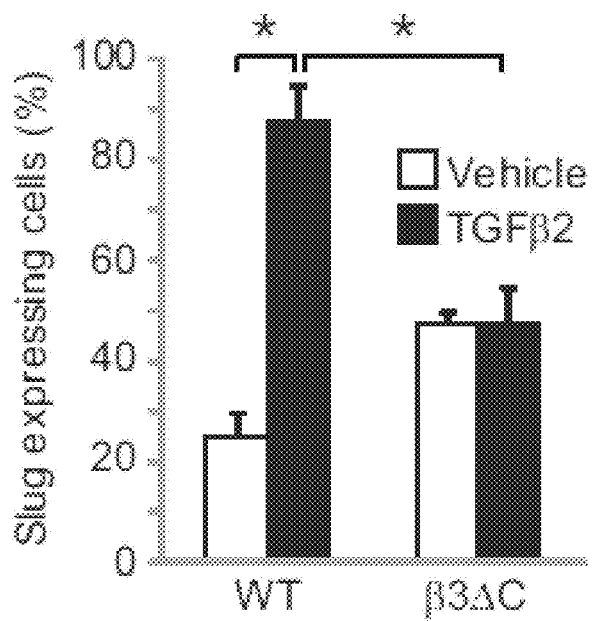

FIG. 21E graphically illustrates quantitation of the percentage of Slug-expressing K14+SMA+ cells from virgin WT and b3DC mammary cells stimulated with vehicle or TGF-b2.

FIGS. 21F-G illustrate Immunoblots of MCF10A cells stimulated with TGF-b2 or vehicle control and probed for the indicated proteins. FIG. 21F: Cells were transfected with control (Ctrl) or b3 siRNA and additionally treated with vehicle or proteasome inhibitor (MG132) for 5 hr prior to lysis. FIG. 21G: Cells were treated with 100 nM Src inhibitor (dasatinib) for the indicated length of time prior to lysis. FIG. 21F and FIG. 21G: Data shown are representative of three independent experiments.

Figure 22B:
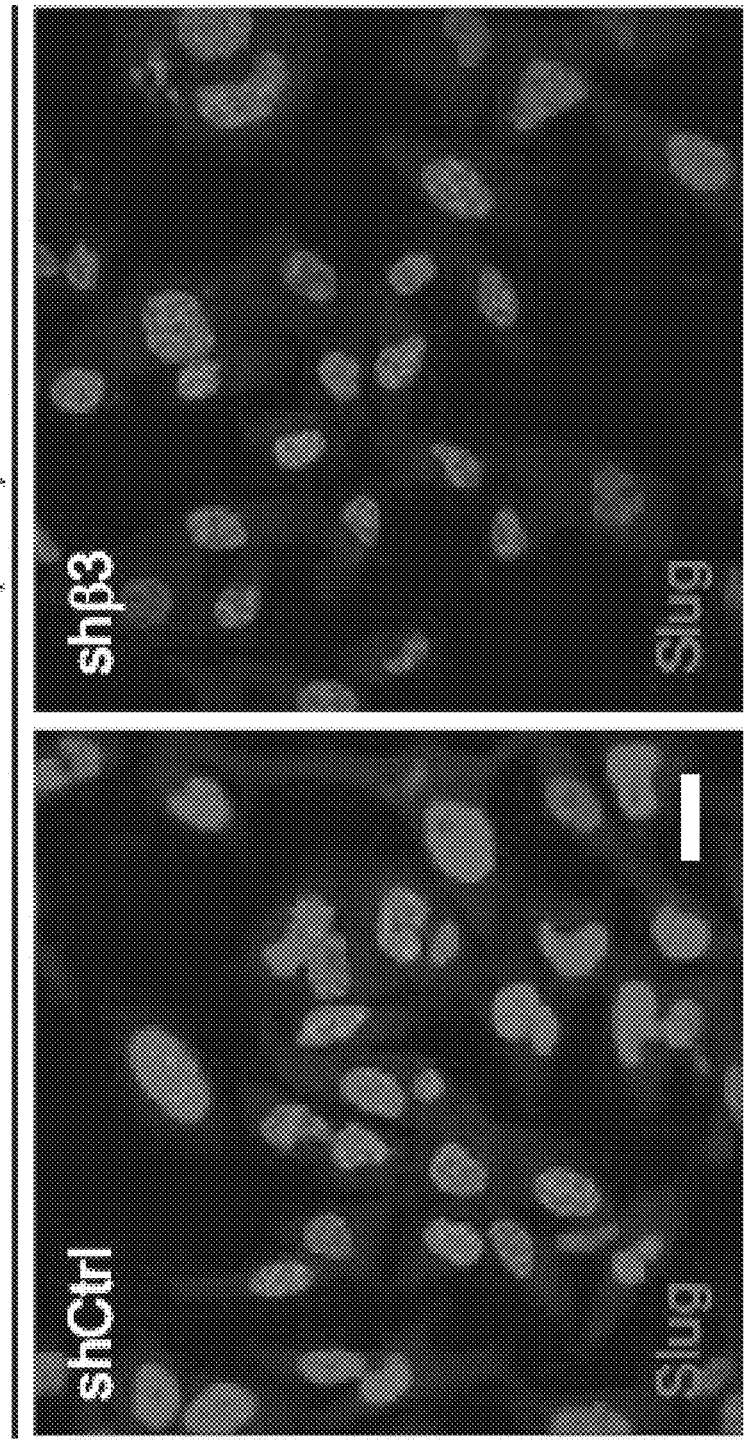
Figure 22C:
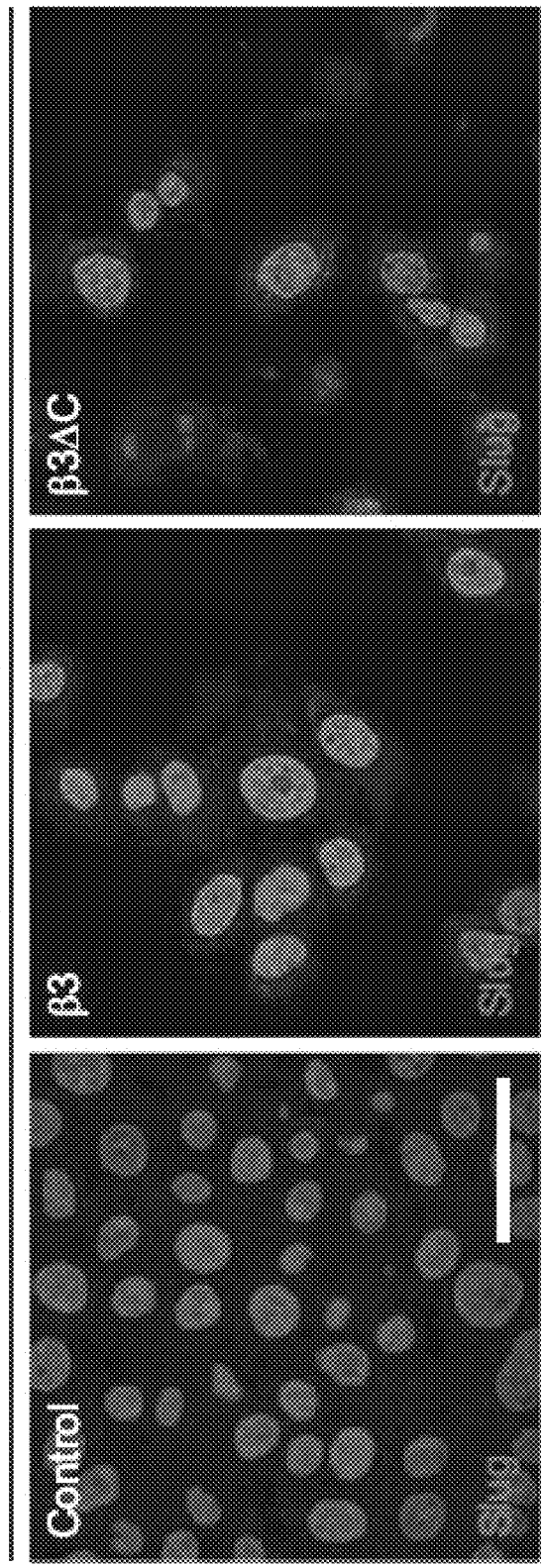

FIGS. 22A-C illustrate representative immunofluorescent images showing Slug expression in (FIG. 22A) MCF-7 cells stably transfected with b3 cDNA or vector alone (Control), (FIG. 22B) a HM variant of MDA-MB-231 cells stably expressing a nonsilencing (shCtrl) or b3 shRNA (shb3), and (FIG. 22C) MDA-MB-468 cells stably expressing vector control, full-length b3 or the b3DC mutant. For FIG. 22A, FIG. 22B, and FIG. 22C: nuclei are stained blue in all panels. Scale bars, 20 mm.

Figures 22D, 22E:
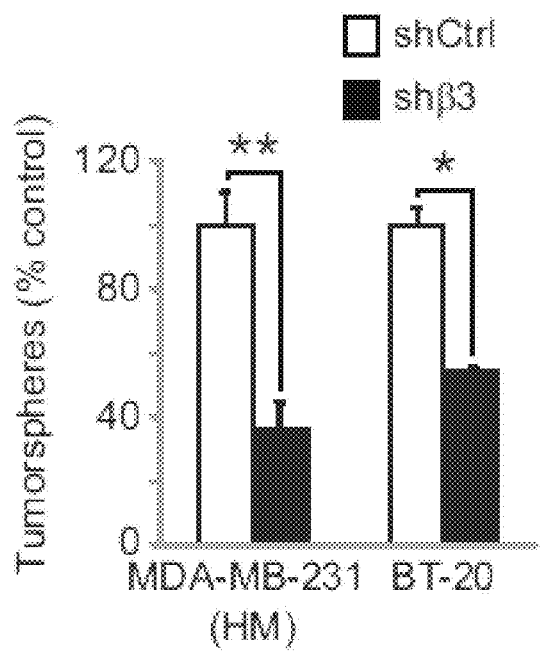

FIG. 22D graphically illustrates a Histogram depicting the results of b3 knockdown on soft agar colony number in MDA-MB-231 (HM) or BT-20 human tumor cell lines compared to control. MDA-MB-231 (HM), n=3, p=0.0079, BT-20, n=2, p=0.031.

Figure 22F:
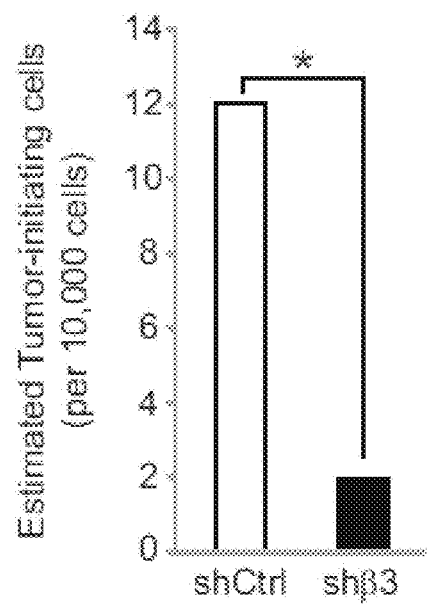
Figure 22G:
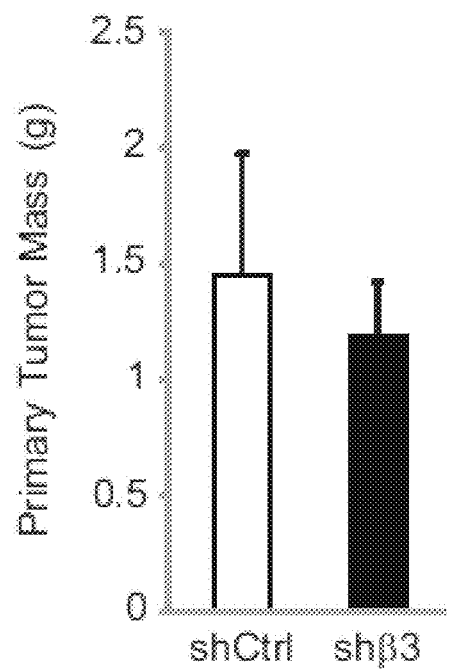

FIGS. 22E-G illustrate in vivo tumor initiation studies comparing control and b3 knockdown MDA-MB-231 (HM) cells injected orthotopically into adult female mice at limiting dilution:

FIG. 22E illustrates a Table describing the frequency of tumor formation per fat pad injected for each cell type.

FIG. 22F graphically illustrates a Histogram showing the estimated number of tumor-initiating cells from the data in FIG. 22E.

FIG. 22G illustrates a bar graph depicting the primary tumor mass for each cell type in tumors formed after injection of 10,000 cells and harvested at 6 weeks.

For FIG. 22D and FIG. 22G: data representing the mean±SEM, and statistical analysis was performed by Student's t test. *p<0.05; **p<0.01.

Figure 22H:
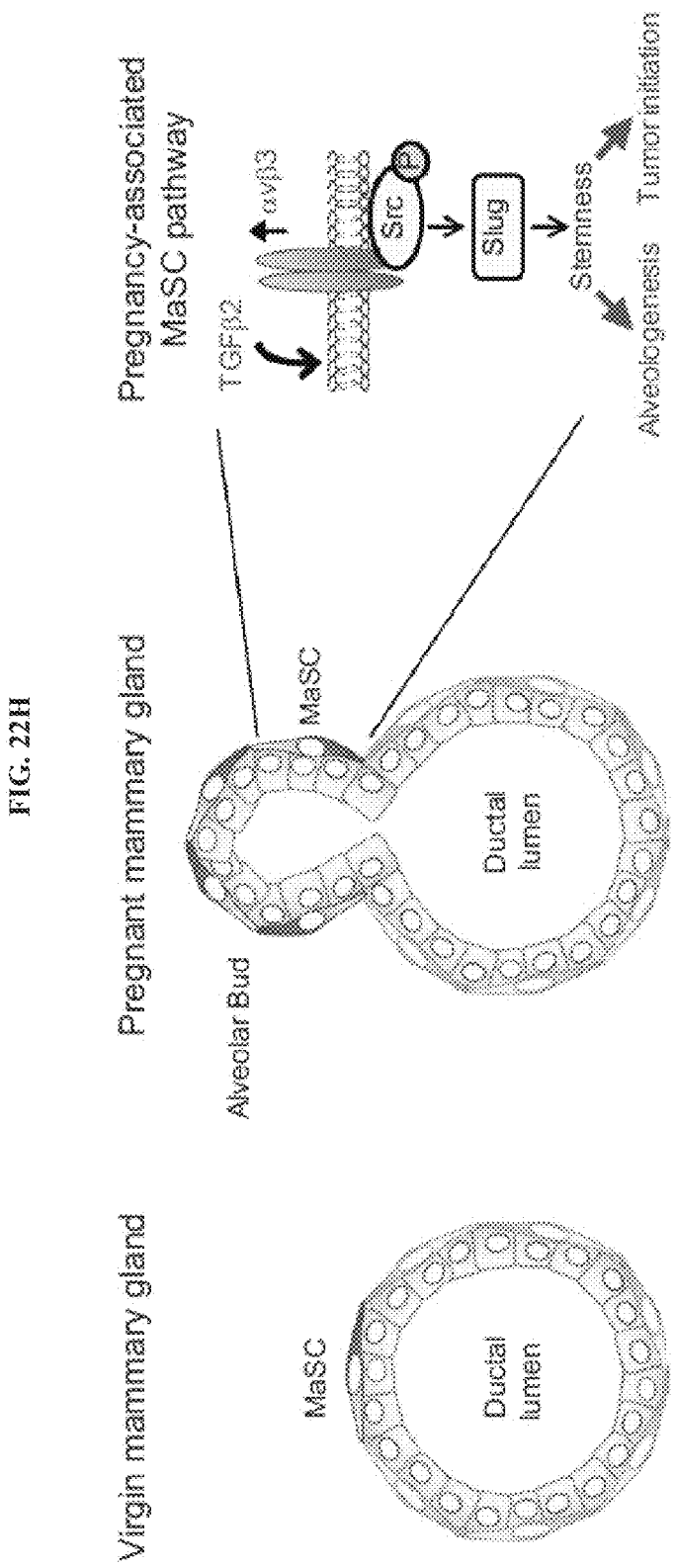

FIG. 22H illustrates a schematic describing the function of the αvβ3-Src-Slug signaling axis in MaSC expansion during pregnancy. Compared to the virgin mammary gland (left panel), pregnancy induces expansion of the MaSC population (green cells), resulting in the initiation of alveologenesis (middle panel). Factors released during pregnancy, such as TGF-b2, drive αvβ3 expression in these pregnancy-associated MaSCs, resulting in activation of SFKs and increased levels of Slug (right panel).

Like reference symbols in the various drawings indicate like elements.

Reference will now be made in detail to various exemplary embodiments as provided herein, examples of which are illustrated in the accompanying drawings. The following detailed description is provided to give the reader a better understanding of certain details of aspects and exemplary embodiments, and should not be interpreted as a limitation on the scope of the invention.

DETAILED DESCRIPTION

In alternative embodiments, provided are products of manufacture, such as assays, kits and the like, and nucleic acid constructs, including vectors, expression systems, reporter constructs, and the like, and recombinant or engineered cells and non-human transgenic organisms comprising same, and methods for using these compositions comprising e.g., use of beta3-integrin (ITGB3) promoters operatively linked to a reporter for drug screening, and in alternative embodiments, screening for agents that inhibit beta3-integrin (ITGB3) promoters and/or inhibit cancer cell survival and metastasis. In alternative embodiments, compositions and methods as provided herein are used to identifying novel pathways that lead to cancer cell acquired resistance to drugs, stemness (characteristics of a stem cell that distinguishes it from ordinary cells) and anchorage independent growth. In alternative embodiments, compositions and methods as provided herein are used to characterize distinct populations of cancer cells within a tumor microenvironment. Compounds identified by practicing the methods as provided herein can also modify or regulate, e.g., Hedgehog signaling, IL6 signaling (Jak/Stat), Wnt signaling (canonical and non-canonical), NFKB and the like.

In alternative embodiments, provided are nucleic acids, including e.g., DNA or RNA constructs, such as vectors and expression cassettes, and cells and non-human transgenic organisms comprising these nucleic acids and construct, and methods for using same, for example, screening for agents that inhibit cancer cell survival and metastatic inhibitors to treat cancer. In alternative embodiments, the nucleic acids as provided herein, including e.g., DNA or RNA constructs, vectors, expression cassettes and the like, comprise all or any functional subsequence of (e.g., a functional portion of) a beta3-integrin (ITGB3) promoter, e.g., a human ITGB3 promoter, operatively linked to a reporter or a marker, e.g., a luciferase, a green fluorescent protein (GFP), MILLI-MARK™ anti-Integrin αVβ3 Antibody, clone LM609-FITC (Millipore Corporation, Billerica, Mass.), AP3 Luciferase Reporter Vector (Affymetrix, Santa Clara, Calif.), or other suitable or equivalent reporter or marker. In alternative embodiments, these nucleic acids, including e.g., the DNA or RNA constructs, vectors, expression cassettes and the like, are stably expressed, and/or inducibly or constitutively expressed, in a beta3-negative cell. In alternative embodiments, the ITGB3 promoter is inducible and is activated to express detectable reporter or a marker, e.g., a luciferase, a GFP or other suitable or equivalent reporter or marker. In alternative embodiments, the ITGB3 promoter is constitutively expressed.

In alternative embodiments, before exposure to a test compound, an inducible ITGB3 promoter is exposed to an inducing agent to induce or upregulate expression of the operatively linked nucleic acid marker or reporter (or nucleic acid encoding a reporter or marker). In alternative embodiments, the inducing agent is a drug or chemical, e.g. erlotinib (e.g., TARCEVA™), where the promoter is induced following drug administration. In alternative embodiments, the inducing agent is a conditioned media (CM) comprising a soluble factor from a cell, e.g., a cell under a stress, e.g., a metabolic stress, e.g., because of low/no serum. In alternative embodiments, soluble "inducing" factors are produced by introducing a cellular stress (e.g., a metabolic, a drug treatment and/or a nutrient deprivation). In alternative embodiments, these factors are collected and concentrated from conditioned media at different time points, and optionally also characterized, before administration to the cell or the cell-free extract. In alternative embodiments, the following soluble "inducing" factors are used to induce ITGB3 promoter:

| | |
|---|---|
| WNT5A | wingless-type MMTV integration site family, member 5A |
| LAMA4 | laminin, alpha 4 |
| BDNF | brain-derived neurotrophic factor |
| TIMP3 | TIMP metallopeptidase inhibitor 3 |
| SLC46A3 | solute carrier family 46, member 3 |
| MSLN | mesothelin |
| MFAP2 | microfibrillar-associated protein 2 |
| METRN | meteorin, glial cell differentiation regulator |
| MATN2 | matrilin 2 |
| IGFBP4 | insulin-like growth factor binding protein 4 |
| FBLN1 | fibulin 1 |
| COL5A1 | collagen, type V, alpha 1 |
| PAPPA | PAPPA antisense RNA (non-protein coding); pregnancy-associated plasma protein A, pappalysin 1 |
| HTRA1 | HtrA serine peptidase 1 |
| ERAP1 | endoplasmic reticulum aminopeptidase 1 |

Agents of interest, for example, potential cancer cell survival inhibitors or metastatic inhibitors, are screened for a change in (e.g., a reduction in) reporter or marker (e.g., luciferase, GFP) expression (by e.g., detection of lower amounts of reporter or marker, or lower amount of activity of reporter or marker) when the candidate agents are applied to the cells with the active ITGB3 promoter, e.g., with an induced ITGB3 promoter, such as an induced ITGB3-Luc construct.

In alternative embodiments, applications of methods as provided herein include: screening for agents that inhibit cancer cell survival; identifying novel pathways that lead to acquired resistance or stemness or anchorage independent growth; and characterizing distinct populations of cancer cells within its tumor microenvironment.

In alternative embodiments, provided are compositions and methods for the detection of the upregulation of ITGB3, wherein the detection is by an increase in a reporter or a marker, such as an increase in a bioluminescence or a fluorescence, e.g., a luciferase or a green fluorescent protein (GFP). In alternative embodiments, the cells as provided herein or cells used in the methods as provided herein are cancer cells, or cancer cell lines, or stable cancer cell lines, that express the reporter or marker (e.g., luciferase or GFP) regulated by the ITGB3 promoter region; thus, the methods as provided herein can be used as a tool to identify inhibitors of drug resistance, cellular stress, cancer cell growth, and cancer metastasis. In alternative embodiments, cell lines as provided herein or used to practice embodiments as provided herein include: carcinoma and immortalized cell lines that are beta3 negative (e.g., FG, HCC827, BT474, H441, MCF10A), and drug resistant cell lines, e.g., HCC827R, FGR, H441R.

Described herein for the first time is the function of the ITGB3 promoter region during cellular stress and cancer metastasis, and for the first time describes use of the compositions as provided herein to identify and characterize cancer cells that induce ITGB3 expression.

In alternative embodiments as provided herein, a nucleic acid used to practice embodiments as provided herein comprises a reporter or a marker gene, including nucleic acid sequences that encode proteins that can be used for reporting activity, e.g., enzymes or epitopes. In one aspect, the reporter or marker gene is used to monitor beta3-integrin (ITGB3) promoter expression. In alternative embodiments, the reporter or marker gene is used to monitor beta3-integrin (ITGB3) promoter inhibition, suppression or silencing. In alternative embodiments, the reporter gene encodes or comprises, or contained in: a luciferase; a green fluorescent protein (GFP); a MILLI-MARK™ anti-Integrin αVβ3 Antibody; a clone LM609-FITC (Millipore Corporation, Billerica, Mass.); an AP3 Luciferase Reporter Vector (Affymetrix, Santa Clara, Calif.), and/or the like. Any compound, fluorophore, label, isotope, protein or gene that has a reporting or marking function can be used in the methods provided herein.

In alternative embodiments, nucleic acids used to practice embodiments as provided herein are inserted into the genome of a host cell by e.g. a vector, a virus or any nucleic acid shuttling or insertional mechanism. In alternative embodiments, the insertion is stable. For example, a nucleic acid sequence can be inserted into a genome or a vector by a variety of procedures. In one aspect, the sequence is ligated to the desired position in the vector following digestion of the insert and the vector with appropriate restriction endonucleases. Alternatively, blunt ends in both the insert and the vector may be ligated. In alternative embodiments, viral long terminal repeats (LTRs) are inserted in a flanking pattern to effect insertion of a desired sequence (e.g., a nucleic acid construct, or a chimeric or recombinant nucleic acid, comprising a beta3-integrin (ITGB3) promoter, or a functional subsequence thereof; and a reporter nucleic acid, or a nucleic acid encoding a reporter or a marker protein) into a genome. In alternative embodiments, sequences homologous to a genome target sequence (targeting where in the genome it is desired to insert the desired nucleic acid are inserted in a flanking pattern to effect insertion of the desired sequence into a genome. A variety of cloning techniques are known in the art, e.g., as described in Ausubel and Sambrook. Such procedures and others are deemed to be within the scope of those skilled in the art.

In alternative embodiments, the ITGB3 promoter sequence used in the construct as provided herein or to practice a method as provided herein comprises or consists of (SEQ ID NO:1):

TTTGCAGAGCTGGCTTTTCCCCTTGCAAATTGCTAGTGACGCTTCAGCTG

ATGTGTGTTACTATTAAGGTCCTAGTGTTTGGGAGGGTGGGGCAGGAGGT

GGAGGATTGTCAGAAAAAAATTACATGGAAAAAGATGGCATCTGAGATGT

TTTGAAAGATAAGTGGAATTTTCCAAGTGGAAAAAGGAAGGAAAATCAGT

CAGATAGGAAGGCATGGAGCATTGGGGAATGACAAGTATCTTCTTGGACT

AGGGTGGGAGATGGGCTGGAGAGATGGGTCAGGGCCAGTTGTCTGGCATC

TTGTGTGTCTCAGAAGAGGGTGGGCACGCTGCGTAGGGAAGCCCAGGGCC

ACTCTGAAAGCCCTAAAGGGGAACTGATGCCTCTGGCCTTGTTTTTATCA

CCATCAGGACTACCCATTGAGGCAGGCTGCACTACCAGCTACTTCCTGGT

GCCCTCTTGCTCATAGCCATAGTATTTTGCCTCTCTGAGCTTCCAGAGGT

TTTAAGTCTGGGGAAGACCCAGGGACTCAAAGAAAGATTGGGGTGGGAGA

TAAGGGGCCACAGTTTGGGGGAGTCAGGCAGGAGGCCTTTGAGGAAAATA

GATAAAGTCCCAAAGCCTGTGAGTGTGAATTTGGAGGCAATATGCTGTGT

TCTGAAACGTTTTCAGACACTGGCTAGGTGCAAGCAAGTGTTTGTAGGGC

GAGGCTCTTCATGGACCTATCACTGCTTACGCAAGCTTGGGATGTGGTCT

TGCCCTCAACAGGTAGGTAGTCTACCGGAAAACCAAACTAAGGCAAGAAA

AAAATTAGTGAATAATAAAGGACTGAACCGGTTCAGAGAAGGCATTCAGC

AGATGTTTGCCAGTCAAATGAATTAAAGTGTGAATGAATGAAACTCGAGG

TAGTGGGTGAATGTGTCCCAAGAATCCAGCGAAACAGGGTCTCCCAGGAG

GCGGGACTGGAAGGGTCCGGAGAGGGGCCACAGGCTCCTGGCCTTTCTAA

GCACACCAAGTGCCCAGTCGCGGACCCCCGGGACCAGGATGCGCTGACGA

CCCGGCTGGCAGGCGGGTCCTCGTGGGCGAGGCGAGGGAGGCGGCGAGAG

AGGAGCAATAGTTTCCCACCGCTCCCTCTCAGGCGCAGGGTCTAGAGAAG

CGCGAGGGGATCTAGAGAAGCCGGAGGGGAGGAAGCGCGAGTCCGCGGCC

CGCCCCGTTGCGTCCCACCCACCGCGTCCCCTCCCCTCCCCTCCCGCTGC

GGGAAAAGCGGCCGCGGGCGGCGGCGCCCACTGTGGGGCGGGCGGAGCGC

CGCGGGAGGCGGACGAGAT

In alternative embodiments, related ITGB3 promoter sequences that are biologically active, including fragments, modifications, derivatives, substitutions and the like are suitable for use with embodiments as provided herein.

Figure 5:
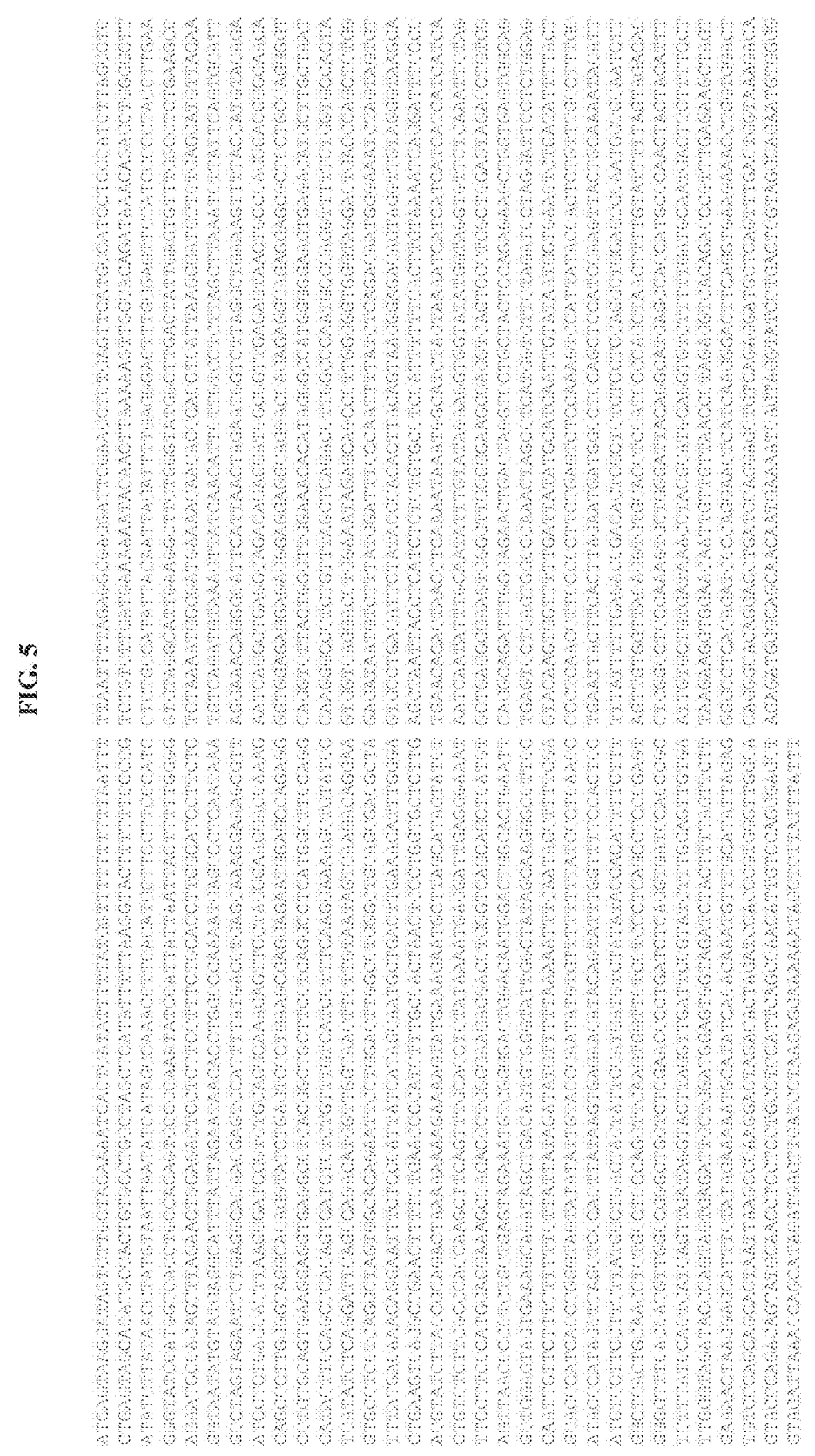

In alternative embodiments, nucleic acid constructs, or chimeric or recombinant nucleic acids as provided herein, or expression cassettes, vectors, plasmids, phagemids, artificial chromosomes and the like, further comprise a distal promoter region of ITGB3, or an enhancer region of ITGB3, e.g., as illustrated in FIG. 5 (the nucleic acid is SEQ ID NO:2), illustrating an enhancer and/or distal promoter region that is approximately 15 kb upstream of ITGB3. In alternative embodiments, a subsequence of SEQ ID NO:2 (FIG. 5) that can function as an ITGB3 distal promoter and/or enhancer also can be used. FIG. 5 illustrates an exemplary nucleic acid sequence of a distal regulatory region of ITGB3, a 15 kb to 10 kb upstream of ITGB3 start site, that can be used to practice embodiments as provided herein, or can be incorporated into a construct as provided herein.

The vector used to make or practice embodiments as provided herein can be chosen from any number of suitable vectors known to those skilled in the art, including cosmids, YACs (Yeast Artificial Chromosomes), megaYACS, BACs (Bacterial Artificial Chromosomes), PACs (P1 Artificial Chromosome), MACs (Mammalian Artificial Chromosomes), a whole chromosome, or a small whole genome. The vector also can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook. Particular bacterial vectors which can be used include the commercially available plasmids comprising genetic elements of the well-known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used to practice embodiments as provided herein as long as it is viable in the host cell. In one aspect, target sequences are integrated into genomes using a lentiviral feline immunodeficiency (FIV) vector for the transduction process.

The invention will be further described with reference to the following examples; however, it is to be understood that the invention is not limited to such examples.

EXAMPLES

Example 1: Making and Demonstrating Efficacy of Compositions and Methods

The data presented herein demonstrates making and using compositions and products of manufacture of embodiments as provided herein.

In alternative embodiments, provided are stable cell lines expressing reporters or markers, e.g., GFP or luciferase, regulated by the ITGB3 promoter and/or enhancer region. Findings show that ITGB3 expression is induced during acquired drug resistance and metastasis. In addition, findings show that ITGB3 expression is required for survival during cellular stress.

In alternative embodiments, provided are compositions and methods for screening for agents that inhibit ITGB3 expression and the phenotypes resulting from ITGB3 upregulation. For example, in screens involved in identifying agents that rescue drug sensitivity, the generated drug resistant cell lines expressing b3 reporter (HCC827R, FGR, BT474R, H441R) can be used. In alternative embodiments, in screens that involve identifying secreted factors that induce ITGB3 expression during cellular stress, conditioned media from serum deprived cancer cells is introduced to exemplary ITGB3 reporter cell lines that are not drug resistant.

Figure 1A:
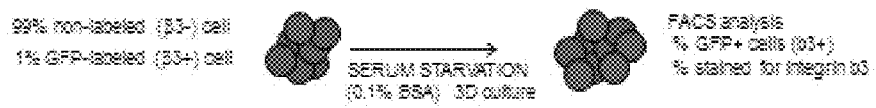
FIGS. 1A-C illustrate data showing that integrin β3 (ITGβ3) expression is enhanced during nutrient deprivation by both selection and induction.
Figure 1B:
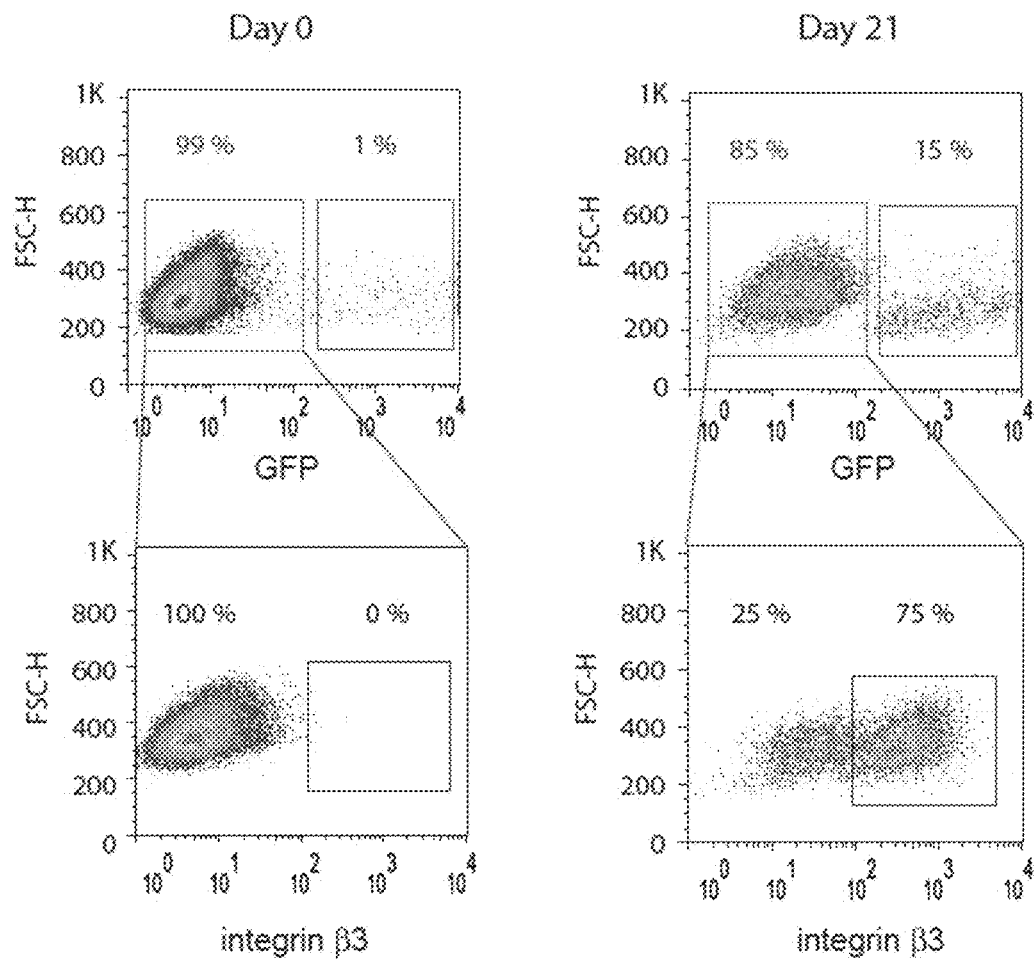
Figure 1C:
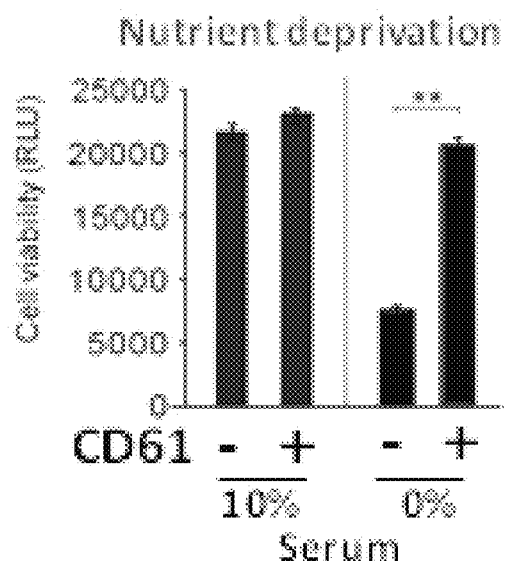
Figure 2A:
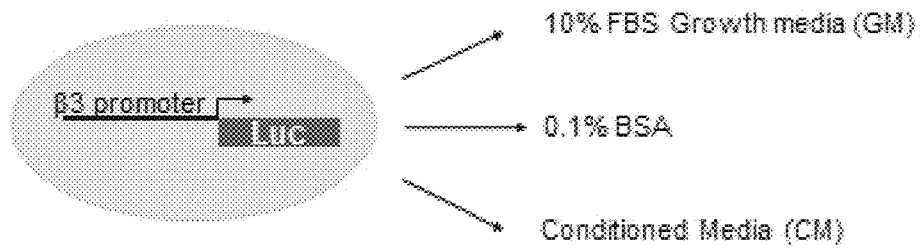
FIGS. 2A-C illustrate data showing that integrin β3 (ITGβ3) expression is induced during nutrient deprivation.
Figure 2B:
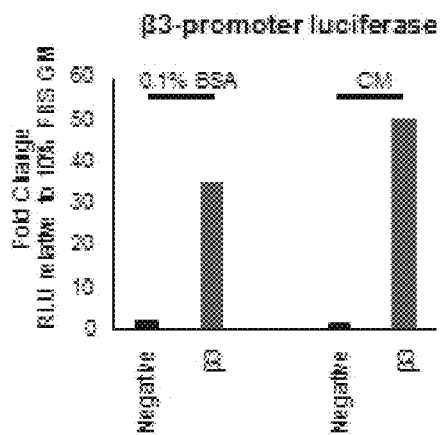
Figure 2C:
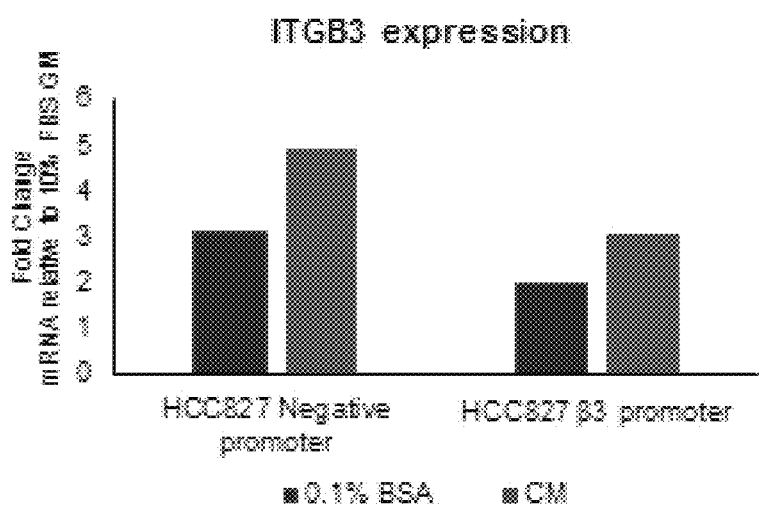
Figure 3A:
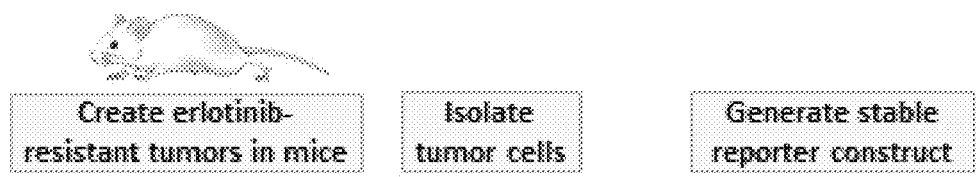
FIGS. 3A-B illustrate data showing that integrin β3 (ITGβ3) expression is upregulated during acquired Tyrosine Kinase Inhibitor (TKI) drug, or erlotinib, resistance.
Figure 3B:
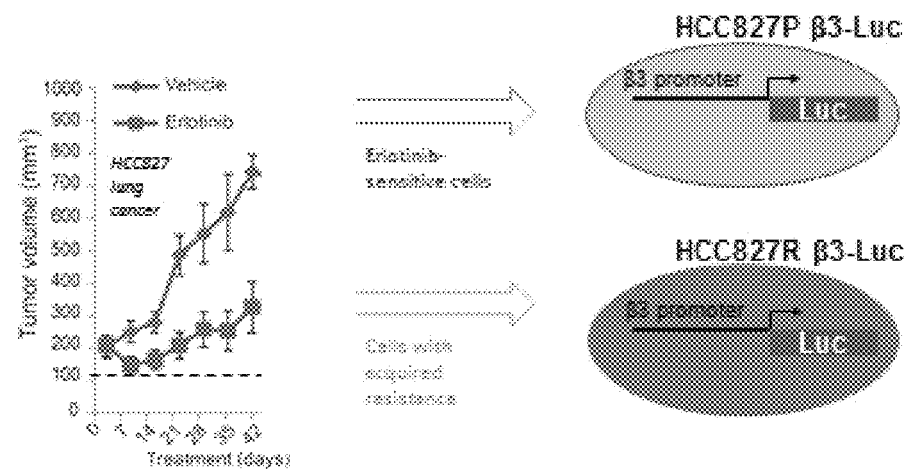
Figure 4A:
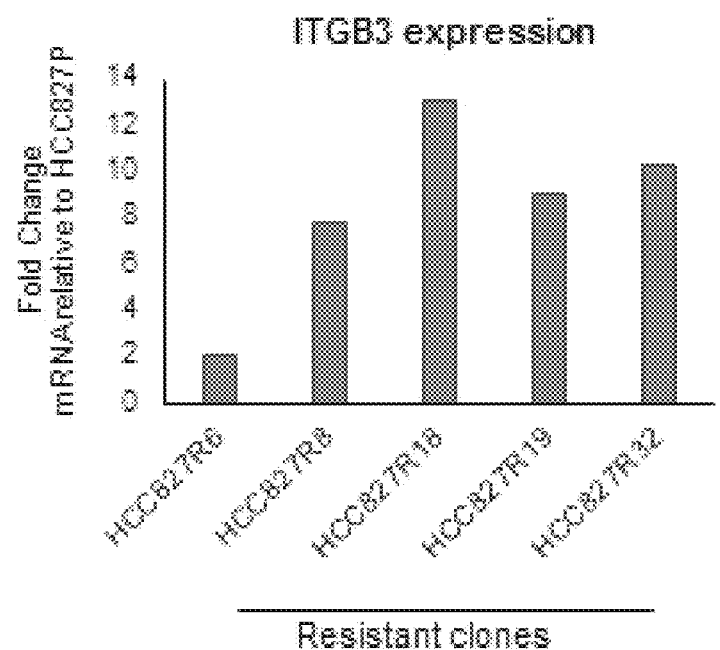
FIGS. 4A-B illustrate data showing that integrin β3 (ITGβ3) expression is upregulated during acquired Tyrosine Kinase Inhibitor (TKI) drug, or erlotinib, resistance.
Figure 4B:
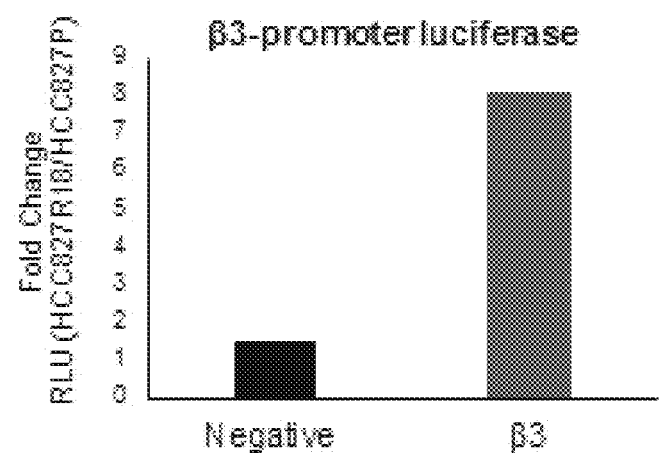
Figure 6:
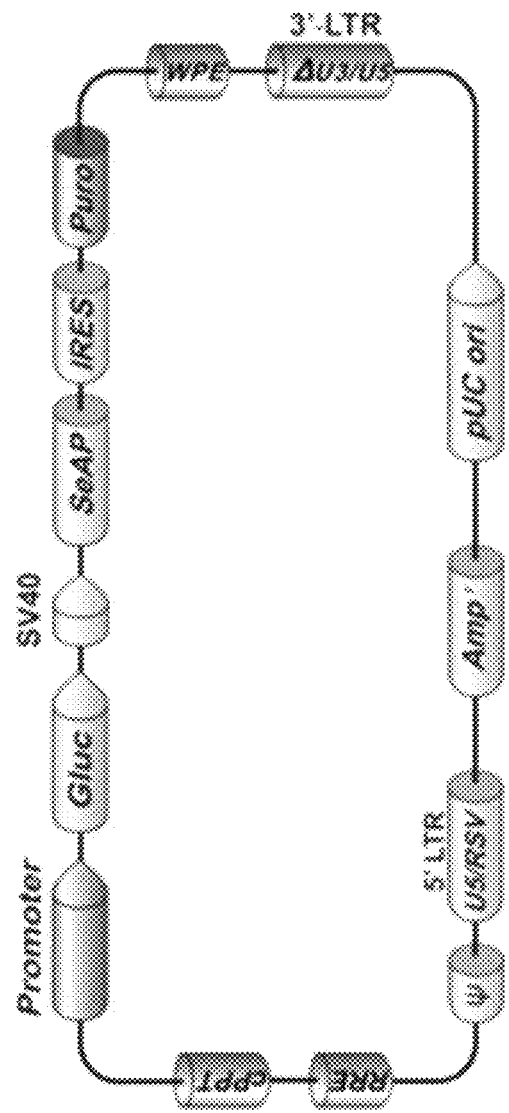
FIG. 6 and FIG. 7 illustrate ITGB3 reporter contructs used to generate exemplary stable cell lines, as further described in Example 1, below.
Figure 7:
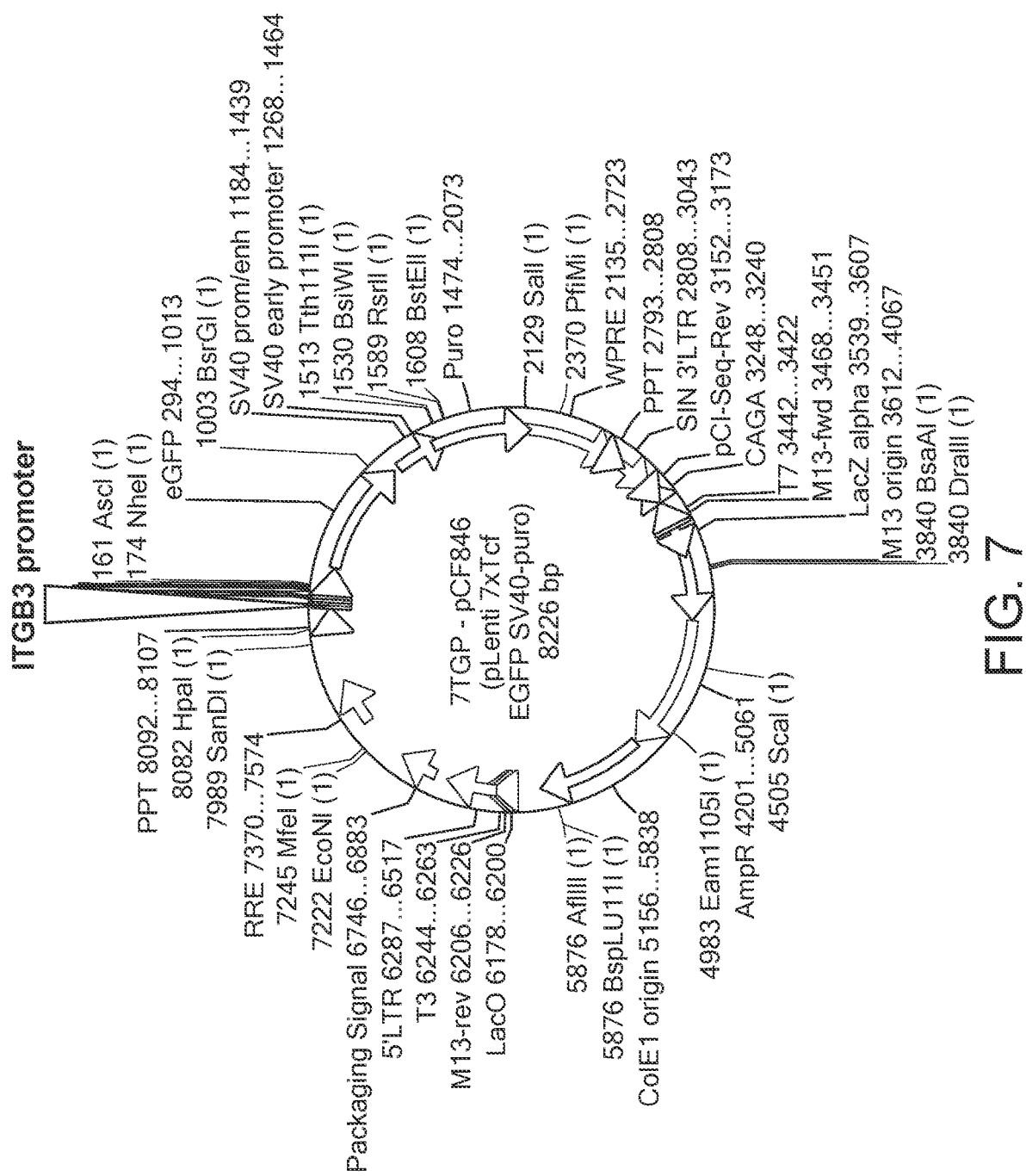
Figure 8:
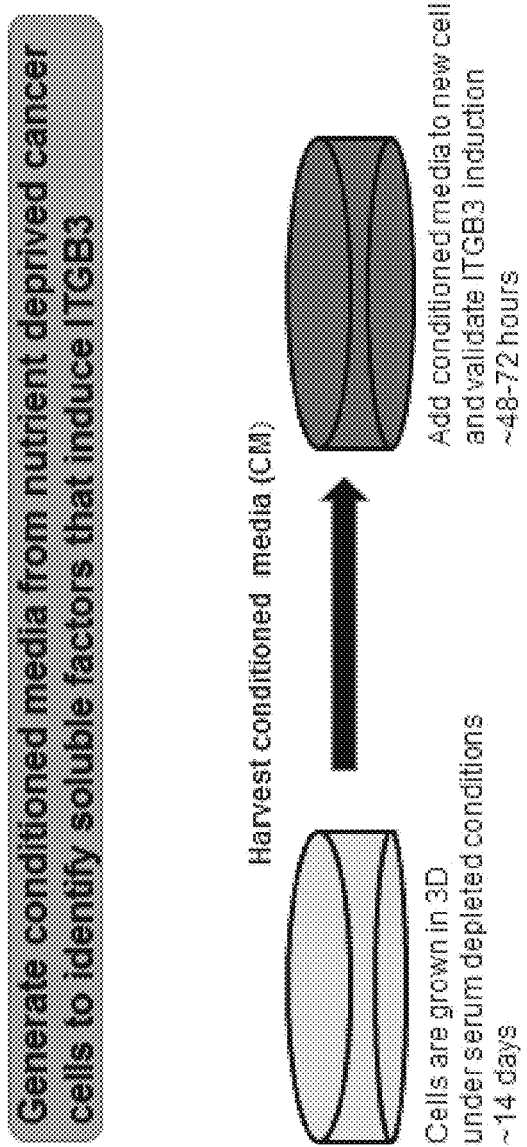
FIG. 8 illustrates schematic of showing an exemplary scheme for identifying soluble factors that induce ITGβ3 by first growing cells in 3D under serum depleted conditions for about 14 days, harvesting the conditioned media (CM) from this culture, then adding the CM to new cells, and then validating ITGβ3 induction at about 48 to 72 hours.
Figure 12A:
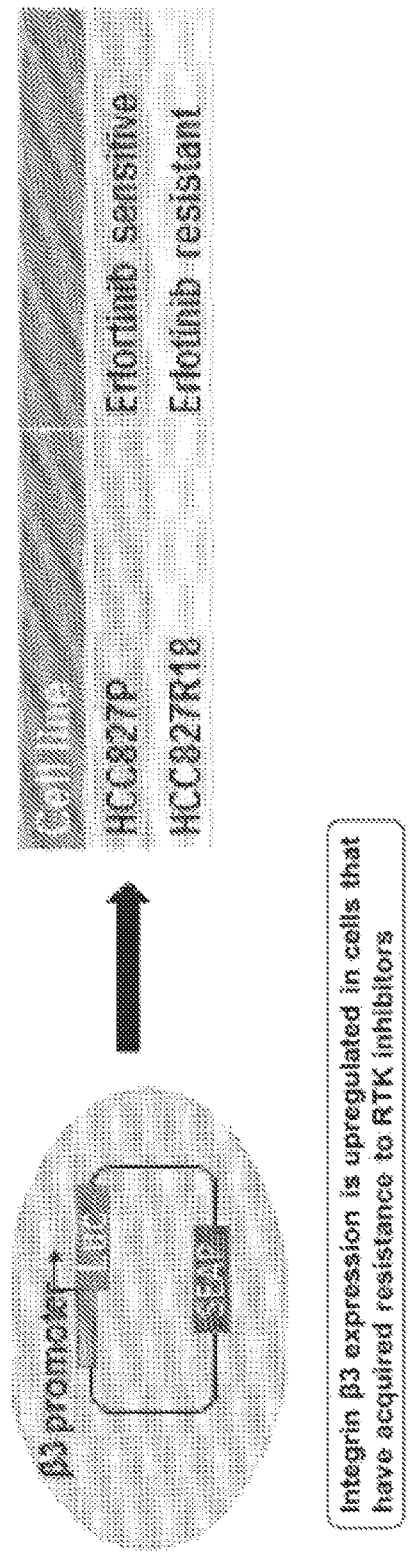
FIGS. 12A-C illustrate data showing that integrin β3 (ITGβ3) expression is upregulated in cells having acquired resistance to Receptor Tyrosine Kinase (RTK) Inhibitors (RTKIs)
Figure 12B:
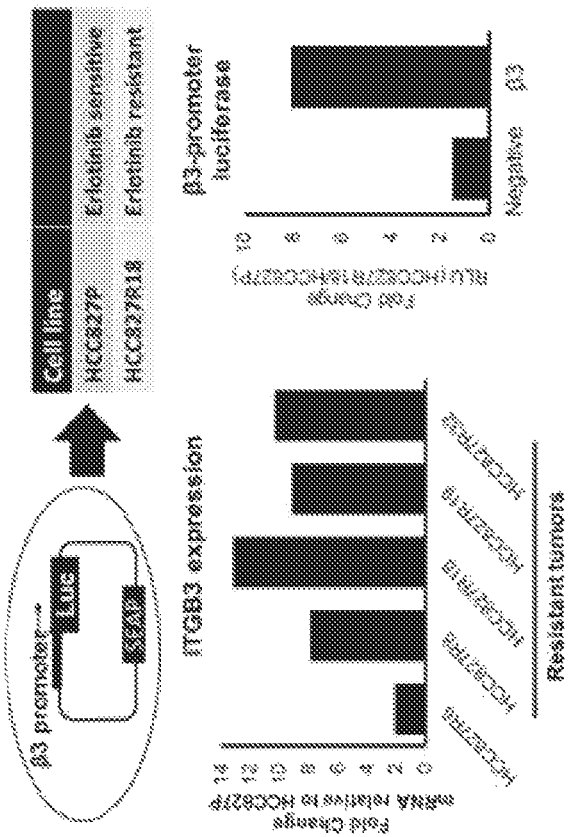
Figures 12C, 13:
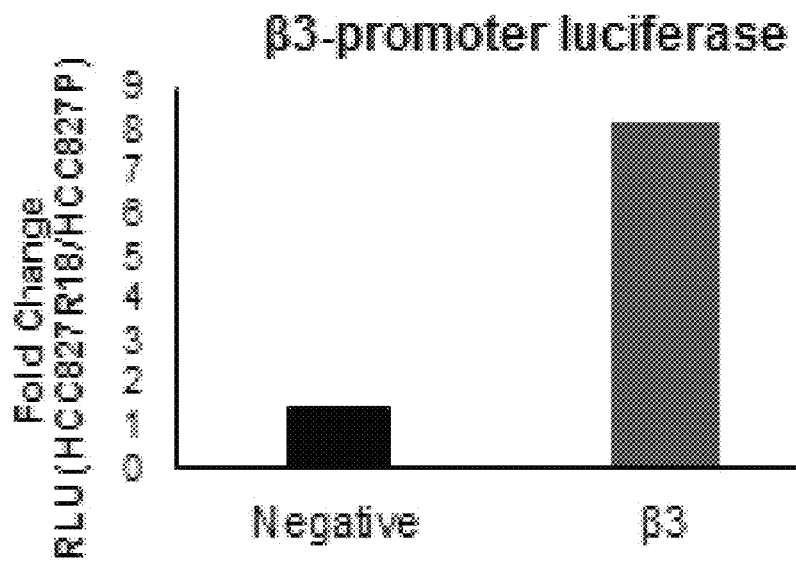
FIG. 13 and FIG. 14 list exemplary cancer cell lines that stably express the ITGB3 reporter luciferase or GFP, where the cells are transduced with lentiviral particle and selected using puromycin.

An exemplary protocol for making constructs and cells as provided herein, or constructs and cells used to practice methods as provided herein:
  Step 1: Generate lentivirus particles containing the ITGB3 reporter construct (as illustrated in FIG. 6) by co-transfecting 293T cells with lentiviral ITGB3 reporter plasmid, packaging plasmid and VSVG.
  Step 2: Generate cancer cell lines that stably express the ITGB3 reporter luciferase or GFP by transducing cells with lentiviral particle and performing selection using puromycin. For list of exemplary cell lines see FIG. 13 and FIG. 14.
  Step 3: Identify soluble factors and agents that inhibit cancer metastasis:
  A. Regulators of ITGB3 Expression During Metabolic Stress:
    Grow cell line from Step 2 in 3D under stress conditions (e.g., serum deprivation, conditioned media from a serum-starved cell, RTK inhibitors, hypoxia) for 48-72 hours so that luciferase is expressed. Conditioned media is prepared by metabolically stressing the cell line by serum starvation for 14 days.
    Apply an active compound or gene targeting shRNA to the cells in Step 2 to identify agents that alter ITGB3 promoter activity.

Figure 9A:
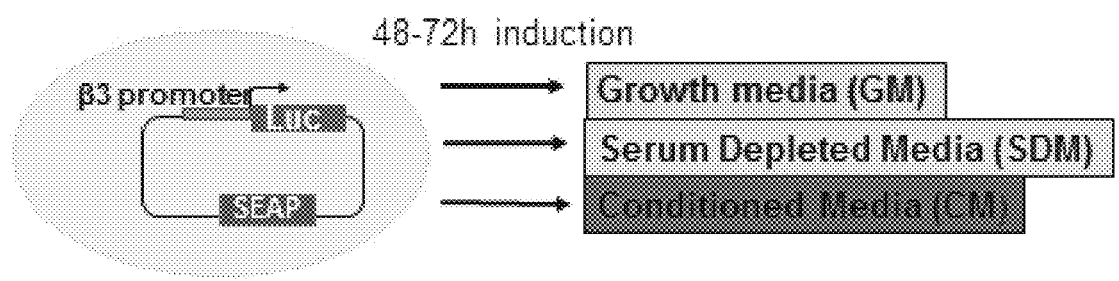
FIGS. 9A-C illustrate data showing that integrin β3 (ITGβ3) expression is induced in serum starved conditions.
Figure 9B:
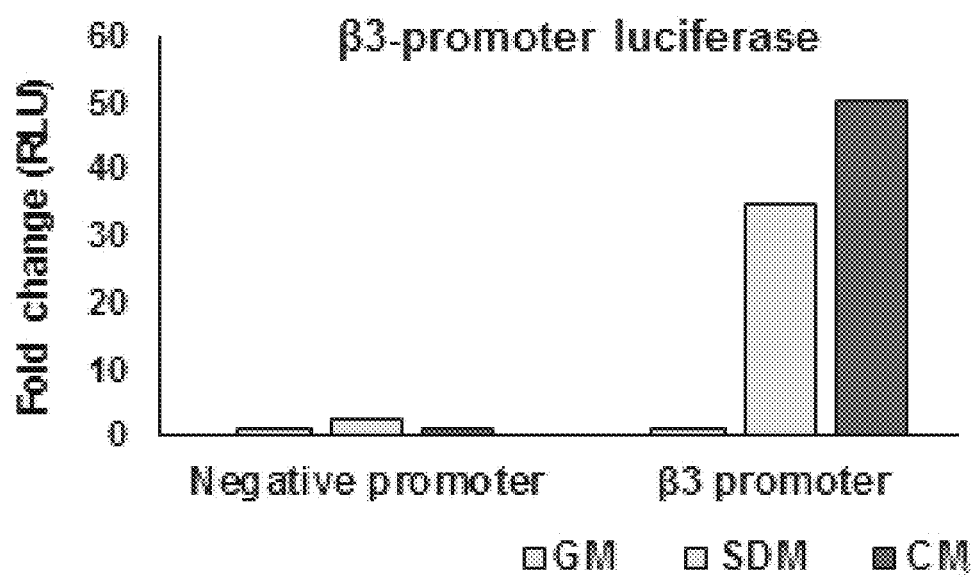
Figure 9C:
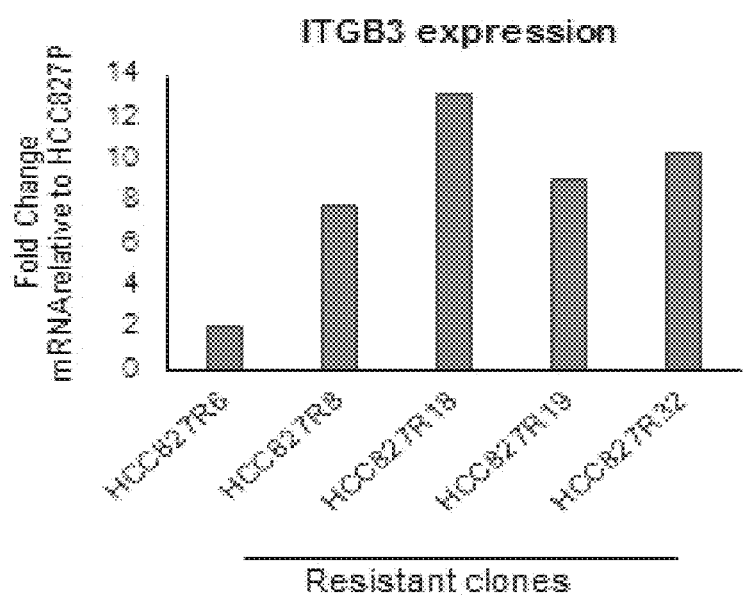
Figure 10:
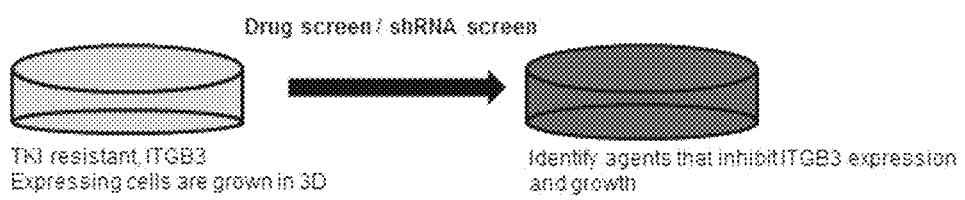
FIG. 10 illustrates schematic of showing an exemplary scheme for identifying agent that in anchorage independent growth by first growing tyrosine kinase inhibitor (TKI) resistant/integrin β3 (ITGβ3) expressing cells in 3D, running a drug screen and a small hairpin RNA or short hairpin RNA (shRNA; an artificial RNA molecule with a tight hairpin turn that can be used to silence target gene expression via RNA interference (RNAi)) screen, and then identifying agents that inhibit ITGβ3 expression and cell growth (i.e., agents that can reverse TKI resistance).
Figures 14, 15A:
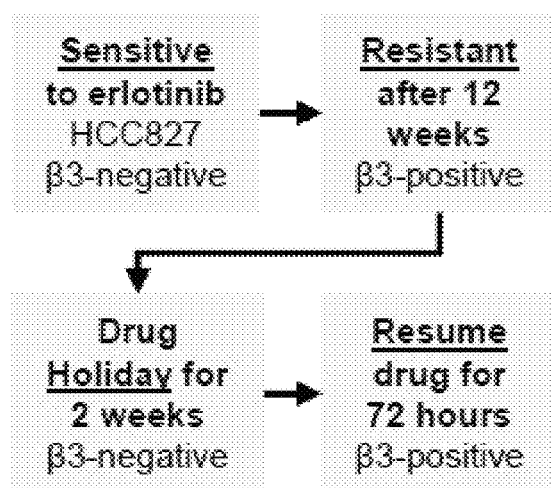
FIGS. 15A-D illustrate studies showing that β3-promoter driven luciferase expression can be used to detect gene activity in stress induced/drug resistant epithelial cancer cells.
Figure 15B:
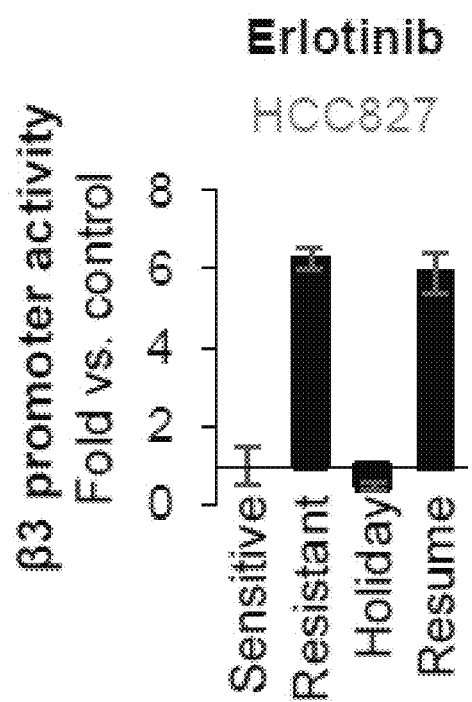
Figure 15C:
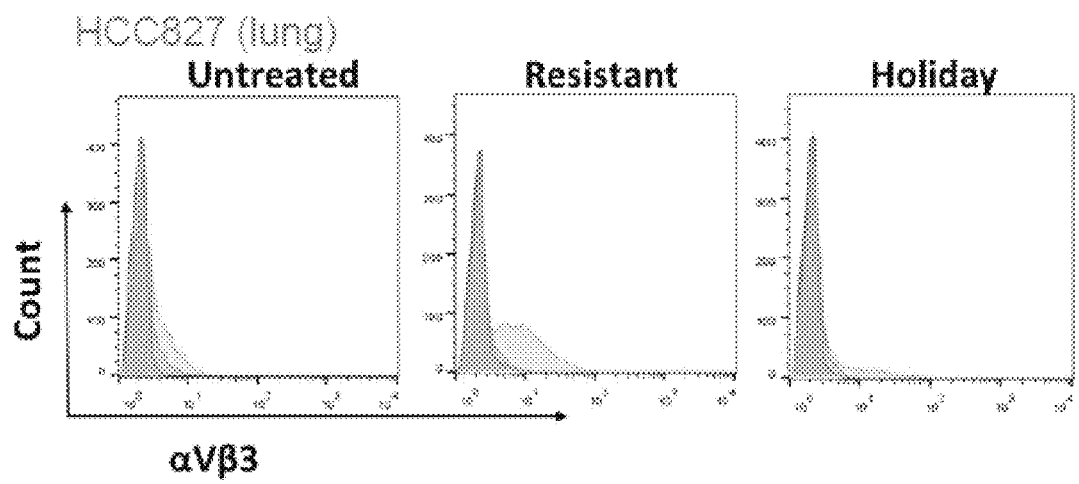
Figure 15D:
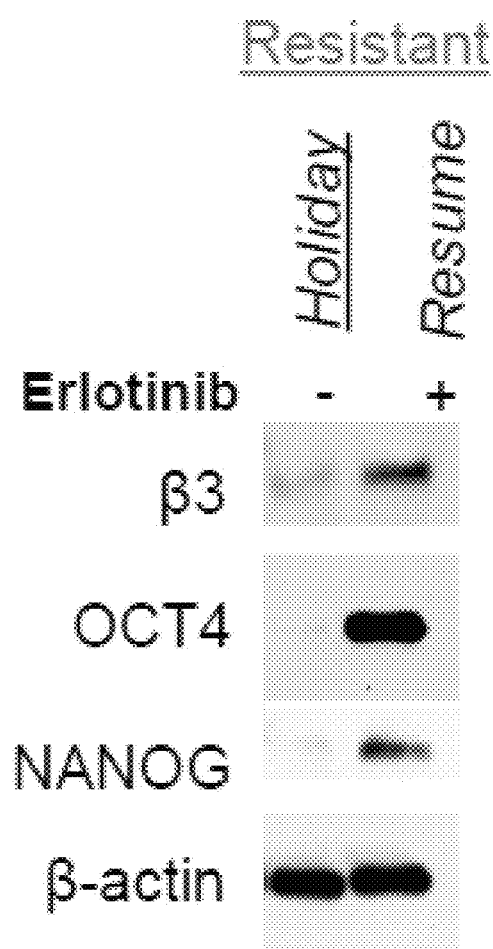

B. Inhibitors of Cancer Metastasis, Stemness and Anchorage Independent Growth:
    Drug resistant cancer cell lines expressing ITGB3 reporter are grown in 3D. Reduction in ITGB3 promoter activity correlates with an inhibitor of stemness, anchorage-independent growth, or metastasis.
    In FIG. 9, ITGB3 expression is by endogenous expression, and it was observed that the fold induction is slightly less with the ITGB3 promoter compared to the negative promoter control. Not being bound by any particular theory, this may be due to competition from the ITGB3-Luc promoter.
    FIG. 15 illustrates data from studies where stable cell lines from parental (drug sensitive) and drug resistant cells containing the ITGB3 luciferase promoter construct to monitor gene regulation and activity; where drug resistant cells given a holiday from erlotinib became re-sensitized to erlotinib and showed a decrease in promoter luciferase activity as measured by RLUs as illustrated in FIG. 15A, and a decrease in the expression of cell surface αVβ3 protein expression as illustrated in FIG. 15B, and a decrease in αVβ3 protein expression as measured by Northern blots as illustrated in FIG. 15C, where the decrease brought down levels of expression to those seen in the original erlotinib sensitive cells, see FIG. 15D. By resuming erlotinib treatment after "erlotinib holiday" data showed induced promoter activity and re-expression of β3 and stem cell genes OCT4 and Nanog as illustrated in FIG. 15C.

Example 2: Integrin Alpha-v/Beta-3 (αvβ3) Drives Slug Activation and Stemness in the Pregnant and Neoplastic Mammary Gland The data presented herein demonstrates making and using compositions and products of manufacture of this invention and used to practice methods of this invention, and describes a role for αvβ3 in regulating Slug activation in MaSCs leading to MaSC expansion and mammary gland remodeling during pregnancy. The data presented herein also demonstrates that αvβ3 also promotes Slug activation, anchorage-independent growth, and tumor initiation in human breast cancer cells, hallmarks of tumor stemness.

Although integrin alpha-v/beta-3 (αvβ3, or avb3) is linked to cancer progression, its role in epithelial development is unclear. Here, we show that αvβ3 plays a critical role in adult mammary stem cells (MaSCs) during pregnancy. Whereas αvβ3 is a luminal progenitor marker in the virgin gland, we noted increased αvβ3 expression in MaSCs at midpregnancy. Accordingly, mice lacking αvβ3 or expressing a signaling-deficient receptor showed defective mammary gland morphogenesis during pregnancy. This was associated with decreased MaSC expansion, clonogenicity, and expression of Slug, a master regulator of MaSCs. Surprisingly, αvβ3-deficient mice displayed normal development of the virgin gland with no effect on luminal progenitors. Transforming growth factor β2 (TGF-β2) induced αvβ3 expression, enhancing Slug nuclear accumulation and MaSC clonogenicity. In human breast cancer cells, avb3 was necessary and sufficient for Slug activation, tumorsphere formation, and tumor initiation. Thus, pregnancy-associated MaSCs require a TGF-β2/αvβ3/Slug pathway, which may contribute to breast cancer progression and stemness.

The epithelial hierarchy in the adult mammary gland represents a well-characterized system with rigorously defined markers (Asselin-Labat et al., 2007; Shackleton et al., 2006; Stingl et al., 2006), allowing us to characterize a possible role for avb3 in this process. Here, we describe a role for αvβ3 in regulating Slug activation in MaSCs leading to MaSC expansion and mammary gland remodeling during pregnancy. Interestingly, αvβ3 also promotes Slug activation, anchorage-independent growth, and tumor initiation in human breast cancer cells, hallmarks of tumor stemness.
Results
β3 is Required for Mammary Gland Development During Pregnancy Previous studies showed β3 surface expression in luminal progenitors and some MaSCs from dissociated virgin mammary glands (Asselin-Labat et al., 2007). Consistent with these findings, we observed β3 expression in basal cells and a subset of luminal cells within the ducts of adult virgin mice (FIG. 16A) that was confirmed by co-staining with basal and luminal markers. These results show that the β3 expression pattern in the intact adult mammary gland is consistent with a potential role for β3 in luminal progenitors and MaSCs. The adult murine mammary gland is a highly dynamic organ, constantly changing in response to hormones released during the estrus cycle and pregnancy. Analysis of β3 in whole mammary gland lysates showed no differences during the estrus cycle; however, relative to virgin glands, we observed increased β3 expression during early and midpregnancy that declined by late pregnancy (FIG. 16B). Notably, the peak levels of β3 at pregnancy day 12.5 (P12.5) coincide with the maximum number of MaSCs reported during pregnancy (Asselin-Labat et al., 2010).

β3 expression in glands from both virgin and pregnant mice suggests a potential function for this receptor in mammary gland morphogenesis at either stage. To address this possibility, we examined the morphology of mammary gland whole mounts from virgin and P12.5 wild-type (WT) and β3 knockout (b3KO) mice, which lack β3 expression in the mammary gland. Although no differences were observed in mammary glands from virgin β3KO mice (FIG. 16C, left panels), marked differences were seen in β3KO mammary glands at P12.5, which demonstrated fewer fine branches and alveolar buds relative to WT glands (FIG. 16C, right panels). Importantly, this defect was maintained throughout late-stage pregnancy and lactation and correlated with decreased viability of litters born to β3KO dams. However, we noted no difference in the ability of β3KO alveoli to produce milk at any stage examined. Quantification of duct/alveoli density in hematoxylin and eosin (H&E)-stained sections showed a nearly 40% decrease in the density of P12.5 β3KO glands relative to WT controls (FIGS. 16D and 16E), consistent with the qualitative assessment of these glands. Thus, β3 appears to be required for mammary development during pregnancy but not for ductal morphogenesis in the virgin adult gland.

Figure 16A:
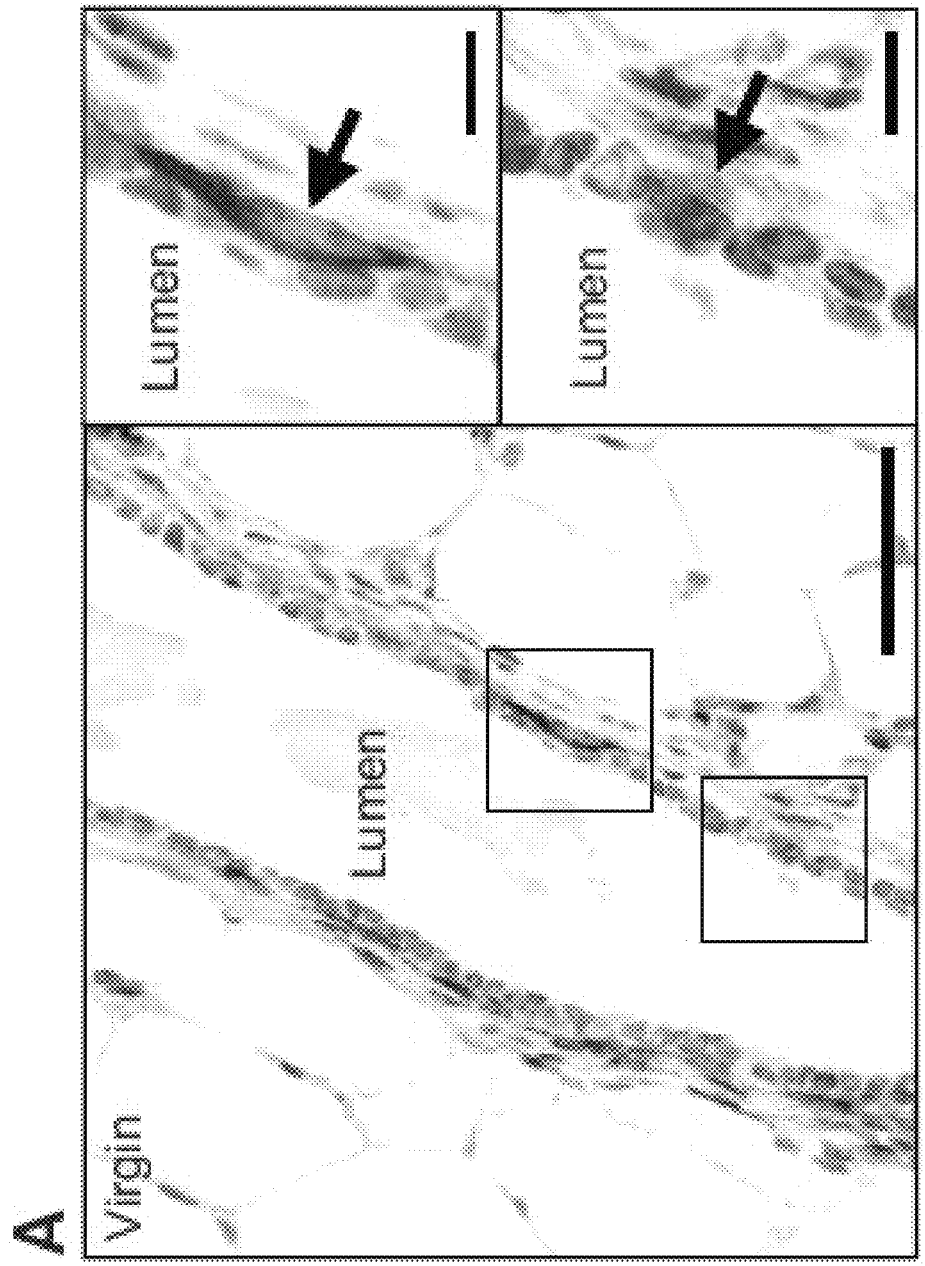
Figure 16B:
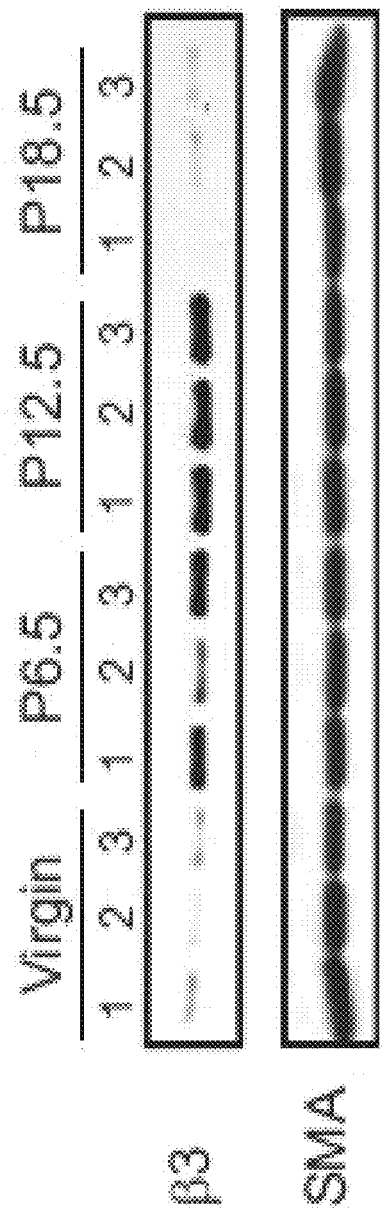
Figure 16C:
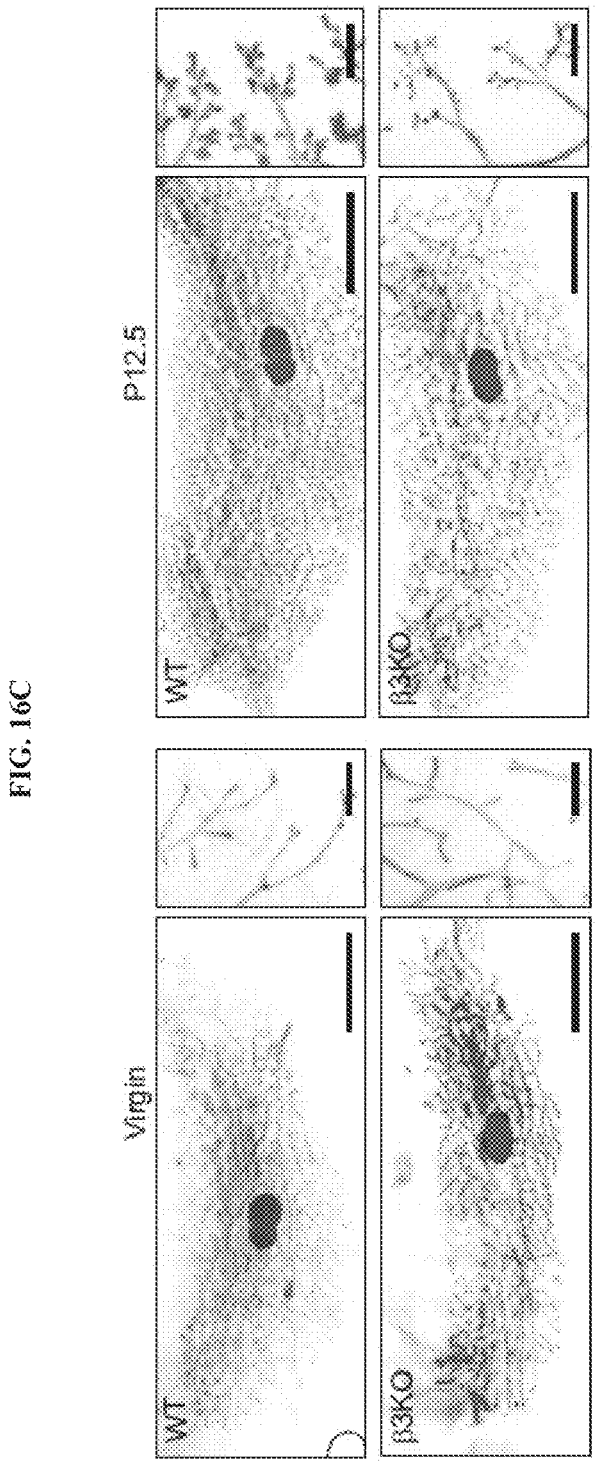

FIG. 16: β3 is Specifically Required for Mammary Gland Development During Pregnancy:

FIG. 16A: Representative images of β3 immunohistochemistry in an adult virgin murine mammary gland. Shown is an example of a duct (left panel) with areas in boxes shown at high power (right panels). Images on right show β3-expressing cells (arrows) in the basal epithelial cell layer (top, right) and a subset of luminal epithelial cells (bottom, right). Scale bars, 50 mm (left panel) and 10 mm (right panels).

FIG. 16B: Western blot of whole-mammary gland lysates for β3 and a-SMA (loading control). n=3 mice for each stage.

FIG. 16C: Mammary gland whole mounts from virgin and P12.5 WT and β3KO mice. Virgin, WT (n=8) and b3KO (n=7); P12.5, WT (n=19) and β3KO (n=10). Scale bars, 5 mm (low magnification) and 500 mm (high magnification).

FIG. 16D: Representative H&E-stained sections from WT and β3KO P12.5 mammary glands. Scale bars, 500 mm.

Figure 16E:
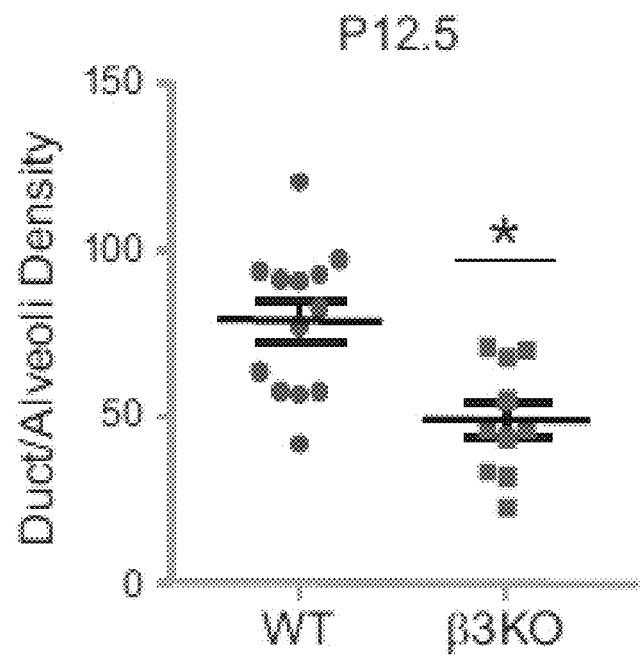

FIG. 16E: Quantitation of duct/alveoli density in P12.5 WT versus β3KO H&E-stained mammary gland sections (WT, n=13; b3KO, n=10; p=0.015). Data shown represent the mean±SEM and were analyzed by Student's t test. *p<0.05.

Figure 16F:
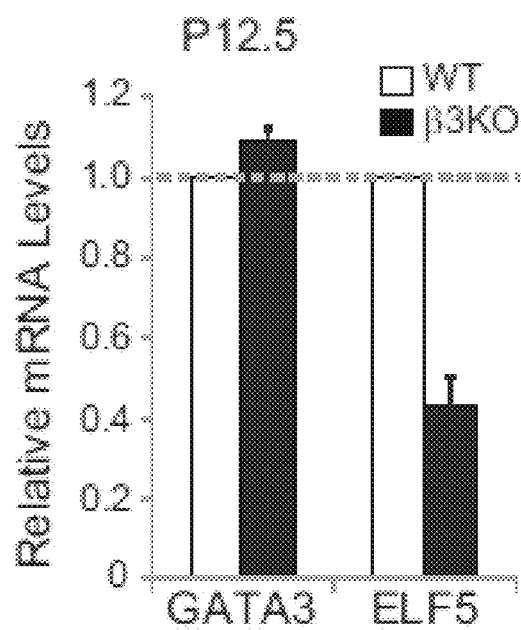

FIG. 16F: qPCR results displaying the relative amount of GATA-3 and ELF5 mRNA in WT and β3KO P12.5 mammary glands (WT, n=11; β3KO, n=9). Each sample was run in triplicate, and glyceraldehyde 3-phosphate dehydrogenase was used as a loading control. Data are displayed as the mean±SD. Fold change ($2^{-DDCT}$) in β3KO glands is relative to WT.

To discern a potential mechanism that accounts for this phenotype, we assessed the relative amounts of epithelial cell proliferation, apoptosis, and differentiation in WT and β3KO P12.5 mammary glands. Quantitative RT-PCR from whole mammary glands showed reduced mRNA levels of the alveolar marker ELF5 (57% decrease), but not the luminal differentiation marker GATA3, in P12.5 β3KO mammary glands relative to WT controls (FIG. 16F). In contrast, we were unable to detect any effect on proliferation or apoptosis, which was essentially absent from the P12.5 gland.

Importantly, we noted similar levels of nuclear ELF5 protein in β3KO alveoli compared to those from WT mice, indicating that the decreased ELF5 mRNA levels observed in P12.5 β3KO mammary glands are consistent with fewer alveoli and not due to dysregulated ELF5 expression. Taken together, these data show that β3 deletion is associated with defective initiation of alveologenesis during pregnancy, suggesting that b3KO mice may display a defect in MaSCs/progenitor cells.

Pregnancy is Associated with Increased β3 Expression in MaSCs

Mammary gland remodeling and differentiation during pregnancy require the coordinated response of multiple cell types, including MaSCs and progenitors (Asselin-Labat et al., 2010; Jeselsohn et al., 2010; van Amerongen et al., 2012; Van Keymeulen et al., 2011). To determine which MaSC/progenitor cell types might require b3 during pregnancy, we first compared β3 expression in WT virgin and P12.5 mammary glands by flow cytometry. Analysis of live (propidium iodide negative) lineage-negative (Lin$^-$; CD31$^-$, CD45$^-$, Ter119$^-$) mammary cells for surface expression of CD24 and CD29 (b1 integrin) identifies enriched populations of mature luminal and progenitor cells (CD24$^+$CD29$^{lo}$ as well as basal and MaSCs (CD24$^+$CD29$^{hi}$) in both virgin (Shackleton et al., 2006) and P12.5 mammary glands (Asselin-Labat et al., 2010).

Figure 17B:
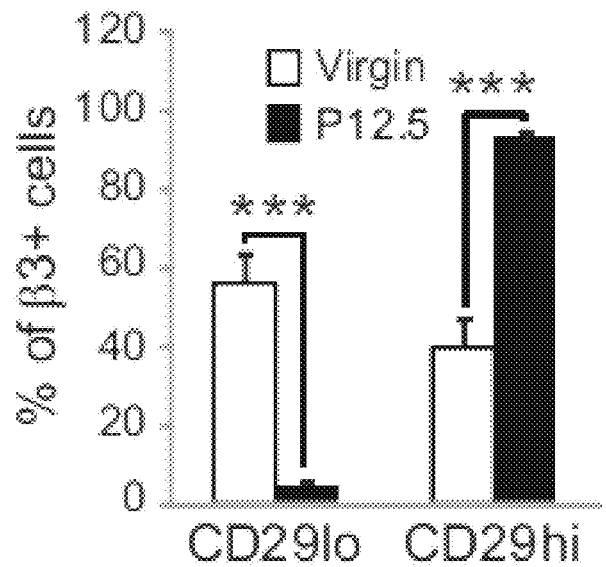
FIG. 17B illustrates Histograms showing the percentage of Lin_CD24+b3+ cells that are CD29lo or CD29hi.
Figure 17C:
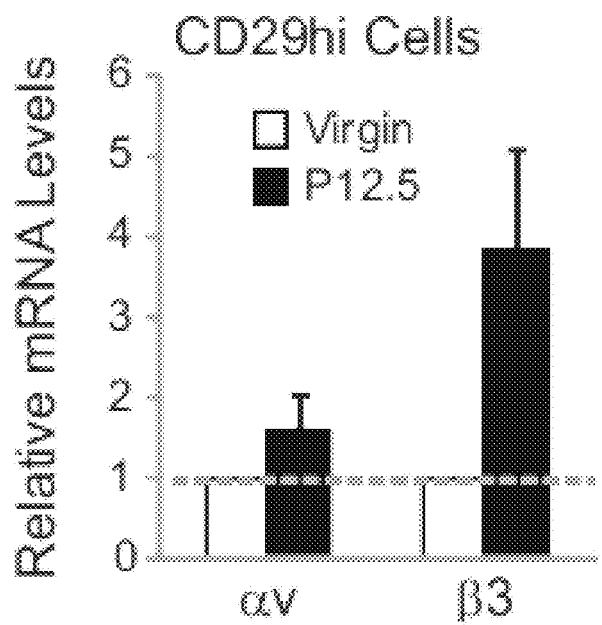
FIG. 17C illustrates qPCR data showing the relative levels of αv and β3 mRNA in virgin and P12.5 CD29hi cells. Virgin, n=2 (pooled from two mice each); P12.5, n=3.
Figure 17D:
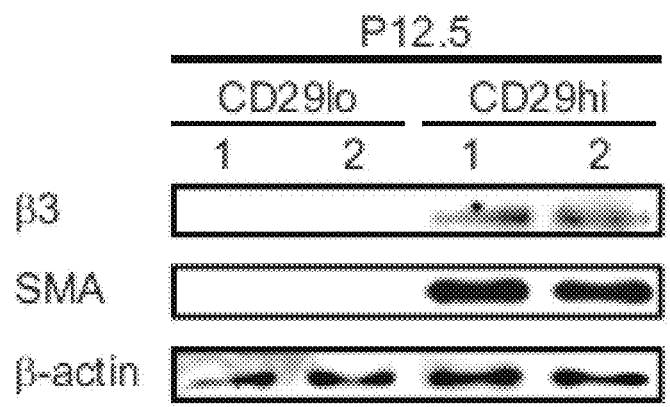
FIG. 17D illustrates an image of an Immunoblot of FACS Lin_CD24+CD29lo and CD29hi mammary cells from two different P12.5 WT mice for β3, SMA (basal marker), and β-actin (loading control).

We then evaluated surface β3 levels in these live Lin$^-$ CD24$^+$CD29$^{hi/lo}$ cells to determine the MaSCs/progenitor cells that express b3 during pregnancy. We found that most b3$^+$ cells in the virgin gland resided in the CD29$^{lo}$ population, and the percentage of b3$^+$CD29$^{lo}$ cells decreased during pregnancy, as previously described by Asselin-Labat et al. (2007) (FIGS. 17A and 17B), though some (33$^+$ luminal cells remained. However, to our surprise, we observed increased b3 surface levels on the P12.5 CD29$^{hi}$ MaSC-enriched population compared to the virgin gland (FIGS. 17A, 17B). Interestingly, this effect is concurrent with the expansion of the CD29$^{hi}$ MaSC pool at this stage (FIG. 17A) (Asselin-Labat et al., 2010). This increased β3 level was transient because it decreased to that of virgin glands after full involution (8 weeks). The increased β3 surface levels in P12.5 CD29$^{hi}$ cells corresponded to a nearly 4-fold induction of β3 mRNA compared to virgin CD29$^{hi}$ cells, with little effect on αv levels (FIG. 17C), suggesting that this effect is due to enhanced β3 expression in these cells. Accordingly, P12.5 b3$^+$CD29$^{hi}$ cells expressed basal markers (FIG. 17D), consistent with β3 co-staining with basal markers in P12.5 mammary sections. These data show that β3 expression is dynamically regulated in CD29$^{hi}$ MaSCs/basal cells at midpregnancy compared to the virgin gland.

Figure 17E:
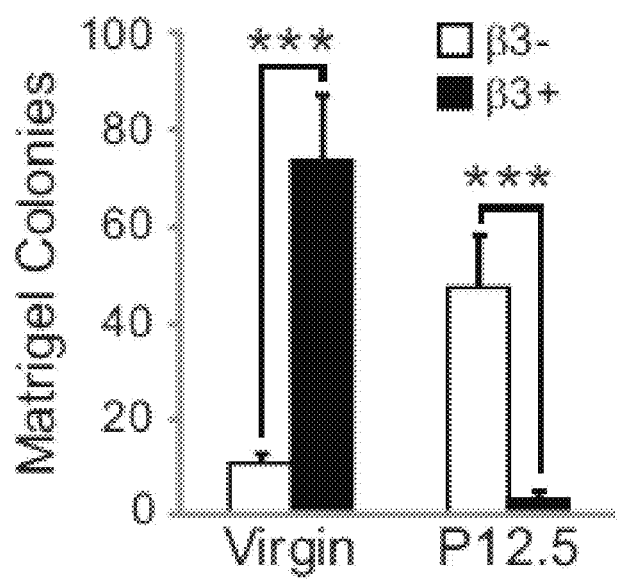
FIG. 17E illustrates Matrigel colonies from live Lin_CD24+b3+ and β3 cells sorted from virgin or P12.5 WT mice. Virgin, n=4 (p=0.00003); P12.5, n=4 (p=0.0014).

Consistent with b3 expression in CD29$^{hi}$ MaSCs/basal cells during pregnancy, we observed that (33$^+$ epithelial cells (Lin$^-$CD24$^+$b3$^+$) from P12.5 mice were unable to form colonies in Matrigel compared to β3$^-$ cells (FIG. 17E). However, these same cells from virgin mice were enriched for Matrigel colony-forming cells, in agreement with their characterization as luminal progenitors (Asselin-Labat et al., 2007) (FIG. 17E). Thus, in addition to differences in CD29 status, β3 expression during pregnancy is associated with a functionally distinct cell population compared to luminal progenitors identified in the virgin mammary gland.

Figure 17G:
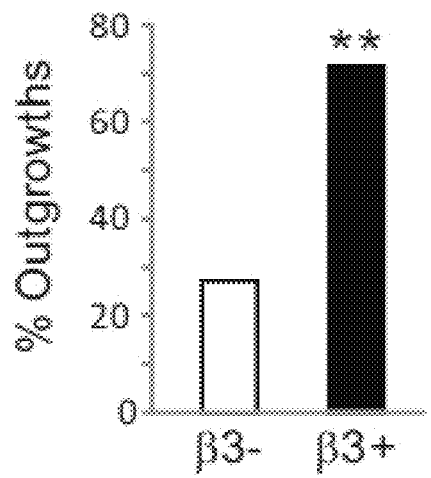
Figure 17H:
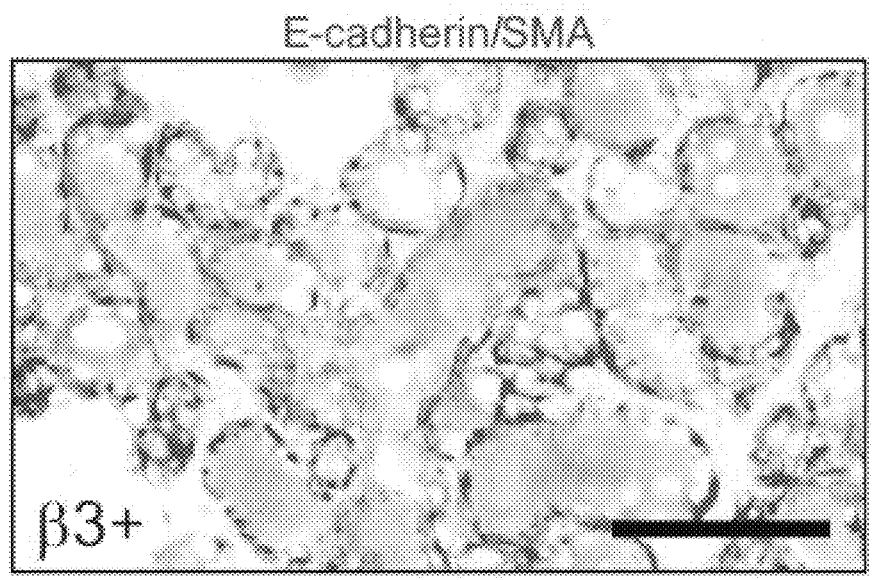

Accordingly, we examined whether (33$^+$ epithelial cells from P12.5 mice were enriched for MaSCs capable of repopulating a fully functional mammary gland similar to CD29hi cells (Asselin-Labat et al., 2010; Shackleton et al., 2006). We tested this possibility by injecting 10,000 Lin$^-$ CD24$^+$ β3$^+$ and β3$^-$ mammary cells from the same donor mice into cleared fat pads of weanling recipients and examining repopulating potential. To simultaneously assess differences in functionality, all outgrowths were harvested at lactating day 2. Although few outgrowths were observed in mice injected with β3$^-$ cells (27%), (33$^+$ cells were enriched for repopulating potential (71%) (FIGS. 17F and 17G), similar to CD29hi cells (Asselin-Labat et al., 2010; Shackleton et al., 2006). Successful outgrowths all appeared swollen with milk (FIGS. 17F and 17H), and the presence of both luminal and basal cell types was validated by immunohisto-chemistry (FIG. 17H). These data show that during pregnancy, epithelial expression of β3 is associated with a previously underscribed population of pregnancy-associated MaSCs.

FIG. 17: β3 Expression Is Increased in MaSCs during Pregnancy (A and B) FACS analysis of MaSC/progenitor markers in virgin and P12.5 WT mammary glands.

FIG. 17 (A) Representative FACS density plots showing the live, Lin_CD24+ cells expressed according to their CD29 (b1 integrin) and β3 status.

FIG. 17 (B) Histograms showing the percentage of Lin_CD24+b3+ cells that are CD29lo or CD29hi. P values for virgin versus P12.5 are the following: CD29lo, p=0.00014; CD29hi, p=0.00008. Data shown are mean±SEM and were analyzed by Student's t tests. ***p<0.001. (A and B) Virgin, n=8, P12.5, n=13.

FIG. 17 (C) qPCR data showing the relative levels of αv and β3 mRNA in virgin and P12.5 CD29hi cells. Virgin, n=2 (pooled from two mice each); P12.5, n=3. Each sample was run in triplicate, and 18S rRNA was used as a loading control. Data are displayed as the mean±SEM fold change (2-DDCT) in P12.5 relative to virgin glands.

FIG. 17 (D) Immunoblot of FACS Lin_CD24+CD29lo and CD29hi mammary cells from two different P12.5 WT mice for β3, SMA (basal marker), and β-actin (loading control).

FIG. 17 (E) Matrigel colonies from live Lin_CD24+b3+ and β3 cells sorted from virgin or P12.5 WT mice. Virgin, n=4 (p=0.00003); P12.5, n=4 (p=0.0014). Data represent the mean±SEM and were analyzed by paired Student's t tests. ***p<0.001.

FIG. 17 (F-H) Mammary gland outgrowth experiments:

FIG. 17 (F) Representative images of carmine-stained mammary gland outgrowth whole mounts from P12.5 Lin_CD24+β3+ and β3 donor cells. Recipients were harvested at lactating day 2. Scale bars, 2 mm.

FIG. 17 (G) Bar graph showing the frequency of successful mammary gland outgrowths from 10,000 Lin_CD24+ β3+ and β3 donor cells from P12.5 mice. Statistical analysis was performed by Fisher's exact test. p=0.006. **p<0.01.

FIG. 17 (H) Representative image of immunohistochemical staining for E-cadherin (brown) and aSMA (red) in sections from Lin_CD24+β3+ cell outgrowths. Scale bar, 100 mm. (F-H) β3, n=22, b3+, n=21 mammary glands from three independent experiments.

β3 is Required for Expansion of Pregnancy-Associated MaSCs

During pregnancy, the proportion of CD29hi MaSCs/basal cells increases dramatically compared to CD29$^{lo}$ luminal cells (FIG. 17A), resulting in an overall increase in MaSC number compared to the virgin gland (Asselin-Labat et al., 2010). Based on the increased β3 surface expression we observed in P12.5 CD29$^{hi}$ cells, we considered whether β3 is required for expansion of MaSCs at this stage. We observed that loss of β3 from P12.5 CD29hi cells decreased the percentage of CD29$^{hi}$ cells relative to CD29$^{lo}$ cells (FIG. 18A). Sorted cell counts showed a similar decrease in the number of CD29hi MaSCs in P12.5 β3KO mice with little or no effect on CD29$^{lo}$ luminal cells (FIG. 18B). Interestingly, loss of β3 did not affect the number of either cell type in virgin glands, consistent with the absence of a role for β33 in luminal progenitors or MaSCs at this stage (FIG. 18B). These findings support a specific role for β3 in regulating expansion of the MaSC-enriched subset during pregnancy.

This defect in CD29$^{hi}$ cell expansion suggests that β3 deletion may result in fewer repopulating cells at midpregnancy. To address this, we performed limiting dilution mammary gland-transplantation assays with CD29$^{hi}$ cells from WT and β3KO P12.5 mammary glands. Results from these experiments showed decreased repopulating frequency in β3KO CD29$^{hi}$ cells that corresponded to a 3.6-fold decrease in the absolute number of MaSCs relative to WT mice (FIG. 18C). In order to simultaneously test the functionality of these transplants, all outgrowths were harvested on lactating day 2. Interestingly, we noted similar levels of ductal elongation and lobular development in β3KO outgrowths compared to WT (FIG. 18D), consistent with the lack of a role for β3 in ductal morphogenesis in the adult gland (FIG. 16C) or alveolar maturation during late pregnancy and lactation. Accordingly, β3 deletion failed to affect the number of lobule-limited progenitors present within the CD29hi cell pool. The more limited outgrowths generated by lobule progenitors are defined by the absence of terminal end bud-like ductal extensions preventing invasion of the fat pad (Bruno and Smith, 2011; Jeselsohn et al., 2010; Smith and Medina, 2008). Taken together, these observations highlight a critical role for β3 expression in specifically regulating MaSC expansion during midpregnancy.

FIG. 18: β3 is Required for MaSC Expansion During Pregnancy:

FIG. 18A illustrates an image of data from a FACS analysis of WT and b3KO virgin and P12.5 mammary glands, FIG. 18A shows representative FACS density plots of WT and b3KO P12.5 mammary cells showing the live, Lin_cells expressed according to their CD24 and CD29 status;

FIG. 18B graphically illustrates the quantitation of the data of FIG. 18A, or the total number of FACS live Lin_CD24+CD29hi and CD29lo cells from virgin and P12.5 mammary glands. p values for WT versus β3KO at P12.5 are as follows: MaSC, p=0.027; Luminal, p=0.09. (A and B) Virgin, WT (n=4) and β3KO (n=4); P12.5, WT (n=7) and β3KO (n=8).

FIG. 18C graphically illustrates a histogram showing the relative levels of total repopulating cells in the CD29hi pool from WT and β3KO P12.5 donor mice (n=4 independent experiments).

For FIG. 18B and FIG. 18C, data represent the mean±SEM, and statistical analysis was performed by Student's t tests. *p<0.05. (B) n.s., not significant (p>0.05).

FIG. 18D illustrates representative images of carmine-stained WT and b3KO outgrowths harvested at lactating day 2. Scale bars, 1 mm.

β3 Signaling is Required for MaSC Clonogenicity During Pregnancy

Decreased MaSC expansion in pregnant β3KO mice suggests a possible defect in MaSC clonogenicity. To evaluate this role for β3, we examined mammary cells from virgin or P12.5 WT or β3KO mice for colony formation on irradiated mouse embryonic fibroblasts (MEFs). In order to preserve the luminal-basal cross-talk present in the intact mammary gland, we used total mammary cells for these experiments. In this assay, MaSCs and progenitor cells form colonies that can be distinguished based on morphology (Stingl, 2009) (FIG. 19A, top panels) and expression of luminal (E-cadherin) or basal (smooth muscle actin [SMA]) markers (Jeselsohn et al., 2010) (FIG. 19A, bottom panels). Luminal progenitors form densely packed colonies that express only E-cadherin, basal progenitors form loose colonies that express only SMA, and MaSCs form mixed colonies that express both E-cadherin and SMA (Jeselsohn et al., 2010; Stingl, 2009). Examining colony morphology by this method, we observed that the proportion of MaSC-like mixed colonies increases at P12.5 (FIG. 19A, left panels, and FIG. 19C) compared to virgin glands (FIG. 19B), consistent with the increased frequency of MaSCs observed at P12.5 (Asselin-Labat et al., 2010). Unexpectedly, examination of colonies from WT and b3KO mice showed that b3 deletion had no effect on MaSCs or luminal colonies in virgin mice, despite β3 acting as a marker of luminal progenitor cells at this stage (Asselin-Labat et al., 2007) (FIG. 19B).

However, loss of β3 significantly decreased the frequency of MaSCs and basal colonies at P12.5 compared to WT mice (FIG. 19C), with a reciprocal increase in luminal colonies (FIG. 19A, right panels, and FIG. 19C). Importantly, β3 deletion did not appear to affect total colony number (19D). The decreased percentage of MaSC colonies in β3KO mice could alternatively be explained by an increase in luminal progenitors. To directly address this possibility, we performed Matrigel colony-formation assays with WT and β3KO CD29$^{lo}$-sorted cells from virgin or P12.5 mice and observed no effect of b3 deletion on luminal progenitor cells at either stage (FIG. 19E). These data highlight a specific role for β3 in regulating MaSC clonogenicity during pregnancy, whereas having no effect on luminal progenitors in either the virgin or pregnant mammary gland.

In addition to their role as cell-adhesion receptors, integrins activate important signaling pathways influencing a diverse array of cell behaviors, including proliferation, survival, and migration. To examine a role for β3 signaling in MaSC/progenitor, behavior, we analyzed knock-in mice expressing a signaling-deficient β3 mutant lacking only the last three amino acids of the β3 cytoplasmic domain (b3DC) (Ablooglu et al., 2009). This mutant prevents the interaction with c-Src and other signaling proteins (Arias-Salgado et al., 2003), resulting in deficient b3 signaling, but does not influence ligand binding (Ablooglu et al., 2009; Arias-Salgado et al., 2003; Desgrosellier et al., 2009). Importantly, previous studies showed that cells from b3DC knockin mice express similar levels of β3 protein compared to those from WT mice, and the β3DC mutant forms functional integrin αvβ3 heterodimers capable of mediating adhesion to β3 substrates (Ablooglu et al., 2009), which we validated in P12.5 mammary glands.

Similar to the β3KO (FIGS. 19B and 19C), no differences were found in colonies from virgin β3DC mice (FIG. 19F), yet we observed fewer MaSC colonies from β3DC mice at P12.5, with proportionally more luminal colonies (FIG. 19G). As observed in β3KO mice, total colony number was unchanged upon β3DC expression, and Matrigel assays showed no difference in luminal progenitor cell number. In fact, examination of P12.5 b3DC mammary gland whole mounts and H&E-stained sections (FIG. 19H) showed fewer fine branches and alveoli relative to WT mice, similar to the phenotype observed in β3KO mice. These results reveal a role not only for β3 expression but, more specifically, the β3 cytoplasmic signaling domain in contributing to P12.5 MaSC clonogenic activation and mammary gland development during pregnancy.

FIG. 19 illustrates that β3-Signaling Is Required for Pregnancy-Associated MaSC Colony Formation:

FIG. 19A illustrates Representative images of WT and β3KO P12.5 colony morphology on irradiated fibroblasts by crystal violet staining (top panels) or immunofluorescent staining for E-cadherin and SMA (bottom panels). Nuclei are stained blue in all panels. Arrows mark SMA-positive cells. Scale bars, 100 mm.

FIG. 19B, FIG. 19C and FIG. 19D graphically illustrate quantitation of the percent MaSC, basal, and luminal colonies (FIG. 19B and FIG. 19C) and total colony number (FIG. 19D) from virgin and P12.5WT and β3KO mice. Virgin, WT (n=6) and β3KO (n=6); P12.5, WT (n=5) and β3KO (n=4). FIG. 19C: p values for WT versus β3KO at P12.5 are as follows: MaSC, p=0.0004; Basal, p=0.005; Luminal, p=0.0004. FIG. 19D: n.s., not significant (p>0.05).

FIG. 19E graphically illustrates a histogram depicting colony formation in Matrigel from FACS CD29lo WT and β3KO cells from virgin and P12.5 mice. Virgin, WT (n=4) and β3KO (n=4); P12.5, WT (n=4) and β3KO (n=4).

FIG. 19F and FIG. 19G graphically illustrate data showing that MaSC, basal, and luminal colonies formed from virgin (F) or P12.5 (G) WT and β3DC mammary cells grown on irradiated MEFs. Virgin, WT (n=2) and β3DC (n=2); P12.5, WT (n=5) and β3DC (n=4).

FIG. 19H graphically illustrates quantitation of duct/alveoli density in P12.5 WT versus β3DC H&E-stained mammary gland sections. WT, n=12, b3DC, n=20.

For FIG. 19B to FIG. 19H, data represent the mean±SEM, and statistical analysis was performed by Student's t tests. *p<0.05; p<0.01; *p<0.001.

TGF-b2 Stimulates b3 Expression, Enhancing MaSC Clonogenicity

Although hormones like progesterone have been shown to increase β3 expression in MaSCs/basal cells of ovariectomized mice (Joshi et al., 2010), this is unlikely to be a direct effect because MaSCs lack steroid hormone receptors (Asselin-Labat et al., 2006). Therefore, to investigate the factors that may account for β3 expression in MaSCs during pregnancy, we evaluated several paracrine factors associated with pregnancy, such as transforming growth factor β (TGF-β) family members and receptor activator of nuclear factor kB ligand (RANKL). Importantly, both RANKL and TGF-β ligands are increased during pregnancy (Asselin-Labat et al., 2010; Fata et al., 2000; Monks, 2007; Robinson et al., 1991), and both pathways affect development of the pregnant mammary gland (Fata et al., 2000; Gorska et al., 2003). Furthermore, RANKL and TGF-b ligands are known to regulate β3 expression in other systems (Galliher and Schiemann, 2006; Lacey et al., 1998).

To examine the ability of these factors to increase β3 expression, we stimulated cells from virgin WT mice and measured β3 expression in MaSCs/basal cells, defined by expression of K14 and SMA. Unexpectedly, we found that TGF-β2, but not TGF-β1 or RANKL, stimulated β3 expression in MaSCs/basal cells relative to vehicle-treated cells (FIG. 20A). Quantitative PCR (qPCR) analysis confirmed TGF-b2's ability to drive β3 mRNA expression specifically in $CD29^{hi}$ MaSCs/basal cells because little effect was observed in $CD29^{lo}$ luminal cells from the same mice (FIGS. 20B and 20C).

Similar effects were observed in human mammary epithelial cells (HMECs), including MCF10As where TGF-β2 was a potent driver of β expression (FIG. 20D). Indeed, we found that TGF-β2 was capable of directly activating the β3 promoter in these cells as determined using a luciferase reporter plasmid containing the proximal 1,300 bp of the β3 promoter upstream of the initial start site (FIG. 20E). Although TGF-β family members commonly induce activation of the SMAD family of transcription factors, analysis of the β3 promoter failed to identify any SMAD consensus binding elements as assessed by querying the ENCODE whole-genome data in the UCSC genome browser (Raney et al., 2011).

However, SMADs commonly exert their transcriptional effects through interacting with SP1 (Feng et al., 2000; Jungert et al., 2006; Poncelet and Schnaper, 2001), which has previously been shown to directly bind the β3 promoter (Evellin et al., 2013). Accordingly, knockdown of SP1 potently blocked TGF-b2-induced b3 mRNA and protein expression (FIGS. 20F and 20G).

The ability of TGF-b2 to drive β3 expression suggested that this ligand may affect MaSC clonogenicity in a β3-dependent manner. Compared to vehicle, only TGF-β2 increased the frequency of bipotent, MaSC-like colonies grown on irradiated MEFs (FIG. 20H), with a reciprocal decrease in luminal colonies (FIG. 20H), an effect similar to that observed in cells from pregnant mice (FIGS. 19B and 19C). This effect was reduced in mammary cells from β3KO mice (FIG. 20H), similar to our results from pregnant b3KO mice (FIG. 19C). TGF-β2 did not affect total colony number unlike TGF-b1, which had a severe growth inhibitory effect, and RANKL, which acted as a potent driver of colony formation (FIG. 20I). Notably, β3 did not contribute to colony number in response to any of these factors, consistent with results from P12.5 β3KO mice (FIG. 19D). Taken together, these data show that TGF-β2, a critical growth factor released during pregnancy, stimulates β3 expression in MaSCs/basal cells and enhances MaSC clonogenicity in a β3-dependent manner.

FIG. 20. TGF-β2 Stimulates β3 Expression, Enhancing MaSC Clonogenicity:

FIG. 20A illustrates representative immunofluorescent images of β3 expression in K14+SMA+ cells (arrows) from pooled virgin WT mammary cells stimulated with the indicated growth factors. Nuclei are stained blue in all panels. Scale bars, 20 mm. Data shown are representative of three independent experiments.

FIG. 20B and FIG. 20C graphically illustrate qPCR analysis comparing the relative levels of β3 mRNA in vehicle versus TGF-β2-stimulated CD29hi (FIG. 20B) and CD29lo (FIG. 20C) cells from WT virgin mice. n=2 independent experiments (pooled samples).

FIG. 20D illustrates an image of an Immunoblot for β3 and b-actin (loading control) in MCF10As and HMECs stimulated with TGF-b2 or vehicle control. Data shown are representative of three independent experiments.

FIG. 20E graphically illustrates a Histogram displaying the relative luciferase activity in MCF10A cells transfected with an empty vector (Ctrl) or a luciferase reporter plasmid containing the proximal region of the β3 promoter (β3 prom-Luc) and stimulated with vehicle or TGF-β2. n=3 independent experiments. p=0.043.

FIG. 20F graphically illustrates data of and FIG. 20G illustrates an image of a representative experiment showing the effect of SP1 knockdown on β3 mRNA (FIG. 20F) and protein (FIG. 20G) expression in MCF10A cells stimulated with TGF-β2 or vehicle control. MCF10A cells transfected with control (siCtrl) or SP1 small interfering RNA (siRNA) (siSP1) were analyzed for b3 mRNA expression by qPCR (FIG. 20F) or β3 protein by immunoblot (FIG. 20G) in the same experiment. n=3 independent experiments.

For FIG. 20B, FIG. 20C, and FIG. 20F: each sample was run in triplicate, and 18S rRNA (FIG. 20B and FIG. 20C) or b-actin (FIG. 20F) was used as loading controls. Data are displayed as the mean±SEM fold change (2-DDCT).

b3 Mediates Slug Activation in Response to TGF-b2 and Pregnancy

The bipotent MaSC-like colonies observed in response to TGF-β2 possess morphological characteristics reminiscent of an epithelial-mesenchymal transformation (EMT) (FIG. 20H). This is consistent with a relationship between EMT genes and MaSC/progenitor cell behavior (Guo et al., 2012), particularly during pregnancy (Chakrabarti et al., 2012). Additionally, TGF-β family members are well characterized for their ability to stimulate EMT in development (Moustakas and Heldin, 2007) and cancer (Katsuno et al., 2013). Consistent with this, TGF-β2 stimulation of MCF10A cells drives changes in the expression of EMT markers such as Slug, E-cadherin, and Vimentin.

Although TGF-β2 induced similar effects on EMT marker protein expression in WT, but not b3KO 2D colonies from virgin mice, no such changes in mRNA expression were noted in sorted CD29hi or CD29lo cells. Thus, TGF-b2-stimulated changes in colony morphology (FIG. 20H) are consistent with increased formation of MaSC-like bipotent colonies, and not an EMT transition of either luminal or basal cell types.

Despite the apparent absence of an effect on EMT, Slug protein levels were consistently reduced in TGF-β2-stimulated β3KO 2D colonies compared to WT, specifically in the K14+SMA+ MaSCs/basal cells. Slug was recently characterized as a determinant of the MaSC fate in the virgin mammary gland (Guo et al., 2012) and is expressed during early to midpregnancy but is negatively regulated by Elf5 during late stage pregnancy/lactation, allowing for alveolar maturation (Chakrabarti et al., 2012). Therefore, we considered whether β3 was required for TGF-β2-mediated Slug expression in MaSCs/basal cells. In virgin WT mammary cells, TGF-β2 induced nuclear Slug expression specifically in K14+SMA+ cells compared to cells treated with a vehicle control (FIGS. 21A and 21B). In contrast, TGF-β2 failed to increase Slug in β3KO cells (FIGS. 21A and 21B), highlighting an essential role for b3 in TGF-β2-stimulated Stimulated Slug protein expression in MaSC-enriched basal cells, despite the absence of an effect on Slug mRNA (Figure S6D).

Given that TGF-β2 expression is induced during pregnancy (Robinson et al., 1991), we hypothesized that β3 may similarly regulate Slug expression in the pregnant mammary gland. Compared to WT glands, we observed dramatically reduced levels of nuclear Slug in the K14+ basal cells of P12.5 β3KO mice (FIGS. 21C and 21D). Despite this decrease in Slug protein levels, Slug mRNA was unaffected in β3KO P12.5 CD29hi cells, similar to the effects observed in TGF-β2-stimulated cells. Thus, β3 appears to play an integral role in regulating Slug protein expression in MaSC-enriched basal cells in response to TGF-b2 or pregnancy with no effect observed on Slug mRNA.

To determine the potential mechanism by which αvβ3 regulates Slug, we considered whether αvβ3 signaling may be required by assessing whether the b3DC mutant affects Slug expression. Whereas TGF-β2 induced Slug in K14+SMA+ mammary cells from virgin WT mice, no increase was observed in cells from β3DC knockin mice (FIG. 21E). The β3DC mutant has previously been characterized as defective in recruiting and activating Src family kinases (SFKs) (Ablooglu et al., 2009; Arias-Salgado et al., 2003; Desgrosellier et al., 2009). Consistent with this, we noted decreased levels of SFK activation (pY416 SFK) in TGF-b2-stimulated K14+SMA+ MaSCs/basal cells from b3DC virgin mice compared to WT cells, suggesting that αvβ3-mediated SFK activation may be required for Slug expression. Indeed, transient b3 knockdown in MCF10A cells significantly reduced TGF-b2-induced pY416 SFK and Slug expression (FIG. 21F), with no effect observed on Slug mRNA.

Interestingly, treatment with an αvβ3 function-blocking antibody (LM609) failed to affect SFK activation or Slug expression, suggesting that this role for αvβ3 may be ligand independent. The absence of an effect on Slug mRNA suggested that αvβ3 may regulate Slug protein through an alternative mechanism. Indeed, Slug protein levels are highly regulated through degradation by the proteasome (Kim et al. 2012; Wu et al., 2012). We found that short-term incubation with a proteasome inhibitor (MG132) was sufficient to restore Slug protein levels to normal in b3 knockdown cells with little effect on Slug levels in control cells (FIG. 21F). Accordingly, short-term incubation with the SFK inhibitor dasatinib reduced only the TGF-b2-induced Slug protein expression (FIG. 21G). Thus, it appears that TGF-β2-stimulated expression of a αvβ3 mediates SFK activation resulting in enhanced Slug protein stability.

FIG. 21: β3 is Required for Slug Activation in Response to TGF-β2 or Pregnancy:

FIG. 21A illustrates images and FIG. 21B graphically illustrates data showing Slug expression in K14+SMA+ cells from virgin WT and b3KO mammary cells stimulated with vehicle or TGF-β2.

FIG. 21A illustrates representative images of Slug expression in K14+SMA+ cells (arrows). Scale bars, 20 mm.

FIG. 21B graphically illustrates quantitation of the percentage of Slug+K14+SMA+ cells. p=0.0439 (vehicle versus TGF-b2 inWT cells) and p=0.0342 (WT versus b3KO cells stimulated with TGF-b2). For FIG. 21A and FIG. 21B: WT, n=3, b3KO, n=3.

FIG. 21C illustrates images and FIG. 21D graphically illustrates data showing Slug expression in WT and b3KO P12.5 mammary glands.

FIG. 21C illustrates representative images of Slug in K14+ cells (arrows). Scale bars, 20 mm. (A and C) Nuclei are stained blue in all panels.

FIG. 21D graphically illustrates a Histogram showing the relative levels of nuclear Slug expression. Data for each mouse represent the average nuclear Slug expression from five fields normalized to total nuclear stain. p=0.0113. For FIG. 21C and FIG. 21D: WT, n=8, b3KO, n=6.

FIG. 21E graphically illustrates quantitation of the percentage of Slug-expressing K14+SMA+ cells from virgin WT and b3DC mammary cells stimulated with vehicle or TGF-b2. WT, n=2, b3DC, n=2. p=0.029 (vehicle versus TGF-b2 in WT cells) and p=0.032 (WT versus b3DC cells stimulated with TGF-b2).

For FIG. 21B, FIG. 21D, and FIG. 21E: data represent the mean±SEM, and statistical analysis was performed by Student's t tests. *p<0.05.

αvβ3 is Associated with Slug Activation and Stemness in Human Breast Cancer Cells Previous studies showed that Slug promotes properties associated with both MaSCs and aggressive stem-like breast cancer cells (Guo et al., 2012; Proia et al., 2011). Our observation that αvβ3 regulates Slug in pregnancy-associated MaSCs prompted us to investigate whether a similar relationship exists in human breast cancer cells. Indeed, using gain- and loss-of-function approaches (FIGS. 22A, 22B and 22C), we found that ectopic expression of b3 was sufficient to drive Slug nuclear accumulation in both MCF-7 and MDA-MB-468 human breast cancer cells, which lack endogenous b3 (FIGS. 22A, 22C), whereas b3 small hairpin RNA (shRNA) knockdown in a highly metastatic (HM) variant of the MDA-MB-231 cells (Munoz et al., 2006) reduced nuclear Slug levels compared to control cells expressing a nonsilencing shRNA (FIG. 22B).

Notably, even unligated αvβ3 was capable of driving Slug expression, as assessed with a b3 mutant deficient in ligand binding (b3 D119A) (Desgrosellier et al., 2009). This is consistent with the inability of αvβ3 antagonists to inhibit Slug expression in nontransformed cells and suggests a ligand-independent role for αvβ3.

Additionally, the b3DC mutant was defective in Slug expression compared to full-length b3 (FIG. 22C), in agreement with our observations from mice (FIG. 21E). Thus, b3 is both necessary and sufficient for Slug activity in human breast cancer cells in addition to regulating Slug expression in pregnancy-associated MaSCs in the mouse.

These findings demonstrate that αvβ3 promotes stem-like properties in tumor cells, which we assessed by tumorsphere formation in vitro and limiting dilution tumor-initiation experiments in vivo. Consistent with the role of unligated αvβ3 in promoting Slug expression, stable b3 knockdown in triple-negative BT-20 and MDA-MB-231 (HM) cells resulted in fewer anchorage-independent tumorspheres relative to controls (FIG. 22D).

Additionally, b3 knockdown in MDAMB-231 (HM) cells reduced the number of tumor-initiating cells compared to control when injected orthotopically into adult female mice at limiting dilution (FIGS. 22E and 22F). Importantly, b3 knockdown had no effect on primary tumor mass in these experiments (FIG. 22G), indicating that αvβ3 has a specific effect on tumor-initiating cells and does not affect basic proliferative and survival responses necessary for primary tumor growth, similar to the effects observed in the mammary gland due to b3 deletion. Together, our findings highlight a conserved role for αvβ3 leading to Slug activity associated with MaSC expansion during pregnancy and stem-like properties in breast cancers.

FIG. 22: αvβ3 is Associated with Slug Activation and Stemness in Human Breast Cancer Cells:

FIG. 22A, FIG. 22B, and FIG. 22C illustrate representative immunofluorescent images showing Slug expression in (FIG. 22A) MCF-7 cells stably transfected with b3 cDNA or vector alone (Control), (FIG. 22B) a HM variant of MDA-MB-231 cells stably expressing a nonsilencing (shCtrl) or b3 shRNA (shb3), and (FIG. 22C) MDA-MB-468 cells stably expressing vector control, full-length b3 or the b3DC mutant. For FIG. 22A, FIG. 22B, and FIG. 22C: nuclei are stained blue in all panels. Scale bars, 20 mm.

FIG. 22D graphically illustrates a Histogram depicting the results of b3 knockdown on soft agar colony number in MDA-MB-231 (HM) or BT-20 human tumor cell lines compared to control. MDA-MB-231 (HM), n=3, p=0.0079, BT-20, n=2, p=0.031.

FIG. 22E, FIG. 22F and FIG. 22G illustrate in vivo tumor initiation studies comparing control and b3 knockdown MDA-MB-231 (HM) cells injected orthotopically into adult female mice at limiting dilution:

FIG. 22E illustrates a Table describing the frequency of tumor formation per fat pad injected for each cell type.

FIG. 22F graphically illustrates a Histogram showing the estimated number of tumor-initiating cells from the data in FIG. 22E.

FIG. 22G illustrates a bar graph depicting the primary tumor mass for each cell type in tumors formed after injection of 10,000 cells and harvested at 6 weeks.

For FIG. 22D and FIG. 22G: data representing the mean±SEM, and statistical analysis was performed by Student's t test. *p<0.05; **p<0.01.

FIG. 22H illustrates a schematic describing the function of the αvβ3-Src-Slug signaling axis in MaSC expansion during pregnancy. Compared to the virgin mammary gland (left panel), pregnancy induces expansion of the MaSC population (green cells), resulting in the initiation of alveologenesis (middle panel). Factors released during pregnancy, such as TGF-b2, drive αvβ3 expression in these pregnancy-associated MaSCs, resulting in activation of SFKs and increased levels of Slug (right panel). This pathway may lead not only to MaSC expansion and alveologenesis during pregnancy but may additionally contribute to stem-like properties in breast cancer cells, resulting in tumor initiation.

DISCUSSION

Integrin αvβ3 is found in some of the most aggressive tumor cells in a diverse array of carcinomas including breast cancer, where it is associated with enhanced tumorigenicity and metastasis (Desgrosellier et al., 2009; Felding-Habermann et al., 2001; Liapis et al., 1996; Sloan et al., 2006; Takayama et al., 2005), yet it is unclear if this is related to a role in epithelial stem/progenitor cells. We now show that αvβ3 plays a specific role in driving MaSC expansion during pregnancy. Genetic deletion of the integrin b3 subunit, or expression of a signaling-deficient form of this receptor, resulted in defective mammary gland development during pregnancy with no effect on ductal morphogenesis in the virgin gland. This phenotype was associated with increased expression of b3 in the MaSC-enriched pool at midpregnancy, an effect reproduced by stimulation with TGF-b2 (FIG. 22H). Examination of MaSC and progenitor cell activity showed that b3 was specifically required for MaSC clonogenicity, expansion and Slug expression during pregnancy with no effect on luminal progenitor cells.

Distinct MaSC/progenitor populations contribute to the development, maintenance, and remodeling of the adult mammary gland (Asselin-Labat et al., 2010; Spike et al., 2012; Van Keymeulen et al., 2011; Wagner et al., 2002). Adult MaSC behavior is highly sensitive to steroid hormones released during the estrus cycle and pregnancy (Asselin-Labat et al., 2007, 2010; Joshi et al., 2010), and these pregnancy-induced MaSCs possess distinct properties compared to MaSCs in the virgin gland, such as more limited self-renewal (Asselin-Labat et al., 2010). Additionally, some MaSCs/progenitors are retained post-pregnancy in the parous gland where they represent a functionally distinct population of parity-induced cells (Matulka et al., 2007). We observed that b3 levels associated with MaSCs during pregnancy were transient, diminishing to levels found in virgin mice after involution. Thus, b3-expressing MaSCs are unlikely to represent parity-induced cells. Instead, our findings characterize integrin αvβ3 as a critical determinant of the MaSC state during midpregnancy, and a requirement for αvβ3 serves to distinguish these cells from MaSCs required for maintenance in the virgin gland.

To our surprise, b3 was not required for luminal progenitor cell function despite characterization of b3 as a surface marker of luminal progenitor cells in the virgin mammary gland (Asselin-Labat et al., 2007). Although our findings show that b3 enriches for luminal progenitors in the virgin gland, consistent with others (Asselin-Labat et al., 2007), genetic deletion of b3 had no effect on luminal progenitor cell clonogenicity or ductal morphogenesis. This is consistent with other reports where genetic deletion of b3 had no effect on ductal morphogenesis in virgin adult murine mammary glands (Taverna et al., 2005). Thus, a potential role for αvβ3 in tumor cell clonogenicity may be linked to its expression on MaSCs during pregnancy rather than on luminal progenitors.

The steroid hormone progesterone is critical for mammary gland remodeling during pregnancy and regulates b3 expression in MaSCs (Joshi et al., 2010). However, MaSCs lack the progesterone receptor (Asselin-Labat et al., 2006), suggesting that progesterone regulates MaSCs indirectly through stimulating release of paracrine factors such as TGF-b and RANKL during pregnancy (Asselin-Labat et al., 2010; Fata et al., 2000; Monks, 2007; Robinson et al., 1991). We show that the TGF-b family member TGF-b2, and not TGF-b1 or RANKL, drives b3 expression in MaSCs/basal cells enhancing MaSC clonogenicity. Similar to our observations regarding b3 expression and function during pregnancy, progesterone and TGF-b family members are critically expressed early in pregnancy and are reduced in late pregnancy, allowing lobular maturation (Gorska et al., 2003; Jhappan et al., 1993; Monks, 2007; Robinson et al., 1991). Thus, integrin αvβ3 may function as a key molecular switch downstream of progesterone-TGF-b signaling that promotes the activation of the MaSC pool during early pregnancy and is reduced in late pregnancy allowing for alveolar secretory maturation most aggressive breast cancers due to frequent metastasis (Schedin, 2006). Interestingly, recent studies have shown that pregnancy is a major regulator of MaSC number and function, suggesting a relationship between MaSCs and pregnancy-associated breast cancers (Asselin-Labat et al., 2010). Accordingly, some proteins that regulate MaSCs during pregnancy also have important functions in aggressive breast tumors (Gonzalez-Suarez et al., 2010; Schramek et al., 2010).

Our findings reveal a specific role for integrin αvβ3 in regulating Slug expression and MaSC expansion during pregnancy. In breast cancer cells, αvβ3 also appears to be necessary and sufficient for Slug activity, anchorage-independent growth, and tumor initiation, properties of stem-like cancer cells (FIG. 22H). These findings highlight a potential relationship between αvβ3's function in pregnancy-associated MaSCs and aggressive stem-like breast cancers.

Experimental Procedures

Histological Analysis, Immunohistochemistry, and Immunofluorescence

For immunohistochemical staining of formalin-fixed paraffin-embedded tissues, antigen retrieval was performed in citrate buffer at pH 6.0 and 95° C. for 20 min. Sections were blocked in normal goat serum diluted in PBS, incubated overnight at 4° C. in primary antibody, followed by biotin-conjugated anti-rabbit immunoglobulin G and an avidin-biotin peroxidase detection system with 3,30-diaminobenzidine substrate (Vector Laboratories), then counterstained with hematoxylin. Whole-mount mouse mammary glands were fixed in Carnoy's solution and stained with carmine. For quantitation of duct/alveoli density, three to four images were randomly sampled from H&E-stained paraffin sections from each mouse with a 43 objective and analyzed with MetaMorph software. For immunofluorescence, frozen sections or fixed cells were blocked with normal goat serum in PBS and incubated in primary antibody overnight at 4° C. followed by secondary at room temperature for 1 hr.

Lysates and Immunoblotting

Whole-mammary gland lysates were prepared by pulverizing glands flash frozen in liquid nitrogen with a mortar and pestle and then lysing the tissue with radio-immunoprecipitation assay lysis buffer (RIPA) lysis buffer. The lysate was further processed with a handheld tissue homogenizer and cleared. Whole-cell lysates were prepared from cell lines with RIPA lysis buffer combined with scraping. Standard western blotting procedures were performed.

Flow Cytometry and Mammary Outgrowth Assays

Single-cell suspensions were prepared and stained with antibodies as described in detail in Supplemental Experimental Procedures. Cell sorting was performed using a FACSDiva or FACSAria (BD Biosciences). For outgrowth experiments, sorted cells were injected into the cleared abdominal fat pads of 3-week-old syngeneic recipients. Estimated repopulating cell frequencies were calculated using the ELDA web-based tool (Hu and Smyth, 2009). All experiments involving mice were conducted under protocols approved by the UCSD animal subjects committee and are in accordance with the guidelines set forth in the NIH Guide for the Care and Use of Laboratory Animals.

Mammary Colony Assays

For colony formation on irradiated MEFs, 100,000 MEFs were seeded into 6-well dishes for 48 hr prior to adding 40,000 cells from digested mammary glands and grown in complete Dulbecco's modified Eagle's medium (DMEM). Colonies formed over 5-6 days before fixing and staining with either 0.1% crystal violet/20% methanol/PBS or 2% paraformaldehyde/PBS for immunofluorescent staining and counting colonies. For Matrigel colonies, 5,000 fluorescence-activated cell sorting (FACS) mammary gland cells were suspended in 50 ml growth factor-reduced Matrigel (BD PharMingen) and grown 14 days in serum-free mammary epithelial cell medium-basal medium (Cambrex) supplemented with B27 supplement, 20 ng/ml epidermal growth factor, 20 ng/ml basal fibroblast growth factor, 4 mg/ml heparin, 100 U/ml penicillin, and 100 mg/ml streptomycin. Total colonies per well were counted from each of the four replicates per experiment.

Growth Factor and Inhibitor Experiments

Cells from digested mammary glands were seeded at 40,000 cells per well onto MEFs (for colony-formation assays) or 8-well chamber slides (Lab-Tek) coated with 2% Matrigel/DMEM. At the time of seeding, cells were suspended in complete DMEM supplemented with vehicle (0.1% BSA/PBS), RANKL (50 ng/ml), TGF-b1 (5 ng/ml), or TGF-b2 (5 ng/ml) (PeproTech). Cells were fixed with 2% paraformaldehyde/PBS after 48 hr (chamber slides) or 5 days (colonies) for immunofluorescent staining.

For experiments with MCF10A and HMECs, TGF-b2 stimulations were performed with 5 ng/ml TGF-b2 (PeproTech) or 0.1% BSA/PBS (vehicle) for 48 hr prior to lysis. In some experiments, 30 mg/ml of the anti-αvβ3 function-blocking antibody LM609 (Millipore) was added to cells at the same time as TGF-b2 or vehicle addition. For the proteasome inhibitor experiments, 10 mM MG132 (Sigma-Aldrich) or DMSO (vehicle) was added to transfected MCF10A cells 5 hr prior to lysis. Treatment of MCF10A cells with the SFK inhibitor dasatinib (ChemieTek) or DMSO (vehicle) was performed with 100 nM dasatinib for the indicated times prior to harvesting lysates.

Orthotopic Breast Cancer

Tumors were generated by injection of MDA-MB-231 (HM) cells expressing nonsilencing or b3 shRNA at limiting dilution (in 50 ml sterile PBS) into the inguinal fat pads of adult (12 weeks) female nonobese diabetic/severe combined immunodeficiency/interleukin-2 receptor g chain knockout mice. Mice were monitored weekly for tumor formation by gentle palpation. Primary tumor mass was determined by assessing the wet weight of the resected tumors. All tumors formed within 5 weeks, and all tumor-bearing mice were harvested at 6 weeks. Tumor-free mice were harvested at 13 weeks, and the absence of any detectable tumor was confirmed by whole-mount staining.

Statistical Analyses

Data presentation and statistical tests are indicated in the figure legends. For all analyses, $p<0.05$ was considered statistically significant.

REFERENCES

Ablooglu, A. J., Kang, J., Petrich, B. G., Ginsberg, M. H., and Shattil, S. J. (2009). Antithrombotic effects of targeting alphaIIbbeta3 signaling in platelets. Blood 113, 3585-3592.

Al-Hajj, M., Wicha, M. S., Benito-Hernandez, A., Morrison, S. J., and Clarke, M. F. (2003). Prospective identification of tumorigenic breast cancer cells. Proc. Natl. Acad. Sci. USA 100, 3983-3988.

Arias-Salgado, E. G., Lizano, S., Sarkar, S., Brugge, J. S., Ginsberg, M. H., and Shattil, S. J. (2003). Src kinase activation by direct interaction with the integrin beta cytoplasmic domain. Proc. Natl. Acad. Sci. USA 100, 13298-13302.

Asselin-Labat, M. L., Shackleton, M., Stingl, J., Vaillant, F., Forrest, N. C., Eaves, C. J., Visvader, J. E., and Lindeman, G. J. (2006). Steroid hormone receptor status of mouse mammary stem cells. J. Natl. Cancer Inst. 98, 1011-1014.

Asselin-Labat, M. L., Sutherland, K. D., Barker, H., Thomas, R., Shackleton, M., Forrest, N. C., Hartley, L., Robb, L., Grosveld, F. G., van der Wees, J., et al. (2007). Gata-3 is an essential regulator of mammary-gland morphogenesis and luminal-cell differentiation. Nat. Cell Biol. 9, 201-209.

Asselin-Labat, M. L., Vaillant, F., Sheridan, J. M., Pal, B., Wu, D., Simpson, E. R., Yasuda, H., Smyth, G. K., Martin, T. J., Lindeman, G. J., and Visvader, J. E. (2010). Control of mammary stem cell function by steroid hormone signalling. Nature 465, 798-802.

Bai, L., and Rohrschneider, L. R. (2010). s-SHIP promoter expression marks activated stem cells in developing mouse mammary tissue. Genes Dev. 24, 1882-1892.

Bruno, R. D., and Smith, G. H. (2011). Functional characterization of stem cell activity in the mouse mammary gland. Stem Cell Rev. 7, 238-247.

Chakrabarti, R., Hwang, J., Andres Blanco, M., Wei, Y., Luka_ci_sin, M., Romano, R. A., Smalley, K., Liu, S., Yang, Q., Ibrahim, T., et al. (2012). Elf5 inhibits the epithelial-mesenchymal transition in mammary gland development and breast cancer metastasis by transcriptionally repressing Snai12. Nat. Cell Biol. 14, 1212-1222.

Desgrosellier, J. S., and Cheresh, D. A. (2010). Integrins in cancer: biological implications and therapeutic opportunities. Nat. Rev. Cancer 10, 9-22.

Desgrosellier, J. S., Barnes, L. A., Shields, D. J., Huang, M., Lau, S. K., Pre' vost, N., Tarin, D., Shattil, S. J., and Cheresh, D. A. (2009). An integrin alpha(v)beta(3) c-Src oncogenic unit promotes anchorage-independence and tumor progression. Nat. Med. 15, 1163-1169.

Evellin, S., Galvagni, F., Zippo, A., Neri, F., Orlandini, M., Incarnato, D., Dettori, D., Neubauer, S., Kessler, H., Wagner, E. F., and Oliviero, S. (2013). FOSL1 controls the assembly of endothelial cells into capillary tubes by direct repression of αv and β3 integrin transcription. Mol. Cell. Biol. 33, 1198-1209.

Fata, J. E., Kong, Y. Y., Li, J., Sasaki, T., Irie-Sasaki, J., Moorehead, R. A., Elliott, R., Scully, S., Voura, E. B., Lacey, D. L., et al. (2000). The osteoclast differentiation factor osteoprotegerin-ligand is essential for mammary gland development. Cell 103, 41-50. Felding-Habermann, B., O'Toole, T. E., Smith, J. W., Fransvea, E., Ruggeri, Z. M., Ginsberg, M. H., Hughes, P. E., Pampori, N., Shattil, S. J., Saven, A., and Mueller, B. M. (2001). Integrin activation controls metastasis in human breast cancer. Proc. Natl. Acad. Sci. USA 98, 1853-1858.

Feng, X. H., Lin, X., and Derynck, R. (2000). Smad2, Smad3 and Smad4 cooperate with Sp1 to induce p15 (Ink4B) transcription in response to TGF-beta. EMBO J. 19, 5178-5193.

Galliher, A. J., and Schiemann, W. P. (2006). Beta3 integrin and Src facilitate transforming growth factor-beta mediated induction of epithelial-mesenchymal transition in mammary epithelial cells. Breast Cancer Res. 8, R42.

Gonzalez-Suarez, E., Jacob, A. P., Jones, J., Miller, R., Roudier-Meyer, M. P., Erwert, R., Pinkas, J., Branstetter, D., and Dougall, W. C. (2010). RANK ligand mediates progestin-induced mammary epithelial proliferation and carcinogenesis. Nature 468, 103-107.

Gorska, A. E., Jensen, R. A., Shyr, Y., Aakre, M. E., Bhowmick, N. A., and Moses, H. L. (2003). Transgenic mice expressing a dominant-negative mutant type II transforming growth factor-beta receptor exhibit impaired mammary development and enhanced mammary tumor formation. Am. J. Pathol. 163, 1539-1549.

Guo, W., Keckesova, Z., Donaher, J. L., Shibue, T., Tischler, V., Reinhardt, F., Itzkovitz, S., Noske, A., Zu" rrer-Ha" rdi, U., Bell, G., et al. (2012). Slug and Sox9 cooperatively determine the mammary stem cell state. Cell 148, 1015-1028.

Hu, Y., and Smyth, G. K. (2009). ELDA: extreme limiting dilution analysis for comparing depleted and enriched populations in stem cell and other assays. J. Immunol. Methods 347, 70-78.

Jeselsohn, R., Brown, N. E., Arendt, L., Klebba, I., Hu, M. G., Kuperwasser, C., and Hinds, P. W. (2010). Cyclin D1 kinase activity is required for the selfrenewal of mammary stem and progenitor cells that are targets of MMTVErbB2 tumorigenesis. Cancer Cell 17, 65-76.

Jhappan, C., Geiser, A. G., Kordon, E. C., Bagheri, D., Hennighausen, L., Roberts, A. B., Smith, G. H., and Merlino, G. (1993). Targeting expression of a transforming growth factor beta 1 transgene to the pregnant mammary gland inhibits alveolar development and lactation. EMBO J. 12, 1835-1845.

Joshi, P. A., Jackson, H. W., Beristain, A. G., Di Grappa, M. A., Mote, P. A., Clarke, C. L., Stingl, J., Waterhouse, P. D., and Khokha, R. (2010). Progesterone induces adult mammary stem cell expansion. Nature 465, 803-807.

Jungert, K., Buck, A., Buchholz, M., Wagner, M., Adler, G., Gress, T. M., and Ellenrieder, V. (2006). Smad-Sp1 complexes mediate TGFbeta-induced early transcription of oncogenic Smad7 in pancreatic cancer cells. Carcinogenesis 27, 2392-2401.

Katsuno, Y., Lamouille, S., and Derynck, R. (2013). TGF-b signaling and epithelial-mesenchymal transition in cancer progression. Curr. Opin. Oncol. 25, 76-84.

Kim, J. Y., Kim, Y. M., Yang, C. H., Cho, S. K., Lee, J. W., and Cho, M. (2012). Functional regulation of Slug/Snail2 is dependent on GSK-3b-mediated phosphorylation. FEBS J. 279, 2929-2939.

Lacey, D. L., Timms, E., Tan, H. L., Kelley, M. J., Dunstan, C. R., Burgess, T., Elliott, R., Colombero, A., Elliott, G., Scully, S., et al. (1998). Osteoprotegerin ligand is a cytokine that regulates osteoclast differentiation and activation. Cell 93, 165-176.

Liapis, H., Flath, A., and Kitazawa, S. (1996). Integrin alpha V beta 3 expression by bone-residing breast cancer metastases. Diagn. Mol. Pathol. 5, 127-135.

Lim, E., Vaillant, F., Wu, D., Forrest, N. C., Pal, B., Hart, A. H., Asselin-Labat, M. L., Gyorki, D. E., Ward, T., Partanen, A., et al.; kConFab (2009). Aberrant luminal progenitors as the candidate target population for basal tumor development in BRCA1 mutation carriers. Nat. Med. 15, 907-913.

Lim, E., Wu, D., Pal, B., Bouras, T., Asselin-Labat, M. L., Vaillant, F., Yagita, H., Lindeman, G. J., Smyth, G. K., and Visvader, J. E. (2010). Transcriptome analyses of mouse and human mammary cell subpopulations reveal multiple conserved genes and pathways. Breast Cancer Res. 12, R21.

Matulka, L. A., Triplett, A. A., and Wagner, K. U. (2007). Parity-induced mammary epithelial cells are multipotent and express cell surface markers associated with stem cells. Dev. Biol. 303, 29-44.

Monks, J. (2007). TGFbeta as a potential mediator of progesterone action in the mammary gland of pregnancy. J. Mammary Gland Biol. Neoplasia 12, 249-257.

Moustakas, A., and Heldin, C. H. (2007). Signaling networks guiding epithelial-mesenchymal transitions during embryogenesis and cancer progression. Cancer Sci. 98, 1512-1520.

Munoz, R., Man, S., Shaked, Y., Lee, C. R., Wong, J., Francia, G., and Kerbel, R. S. (2006). Highly efficacious nontoxic preclinical treatment for advanced metastatic breast cancer using combination oral UFT-cyclophosphamide metronomic chemotherapy. Cancer Res. 66, 3386-3391.

Pece, S., Tosoni, D., Confalonieri, S., Mazzarol, G., Vecchi, M., Ronzoni, S., Bernard, L., Viale, G., Pelicci, P. G., and Di Fiore, P. P. (2010). Biological and molecular heterogeneity of breast cancers correlates with their cancer stem cell content. Cell 140, 62-73.

Poncelet, A. C., and Schnaper, H. W. (2001). Sp1 and Smad proteins cooperate to mediate transforming growth factor-beta 1-induced alpha 2(I) collagen expression in human glomerular mesangial cells. J. Biol. Chem. 276, 6983-6992.

Proia, T. A., Keller, P. J., Gupta, P. B., Klebba, I., Jones, A. D., Sedic, M., Gilmore, H., Tung, N., Naber, S. P., Schnitt, S., et al. (2011). Genetic predisposition directs breast cancer phenotype by dictating progenitor cell fate. Cell Stem Cell 8, 149-163.

Raney, B. J., Cline, M. S., Rosenbloom, K. R., Dreszer, T. R., Learned, K., Barber, G. P., Meyer, L. R., Sloan, C. A., Malladi, V. S., Roskin, K. M., et al. (2011). ENCODE whole-genome data in the UCSC genome browser (2011 update). Nucleic Acids Res. 39, D871-D875.

Robinson, S. D., Silberstein, G. B., Roberts, A. B., Flanders, K. C., and Daniel, C. W. (1991). Regulated expression and growth inhibitory effects of transforming growth factor-beta isoforms in mouse mammary gland development. Development 113, 867-878.

Schedin, P. (2006). Pregnancy-associated breast cancer and metastasis. Nat. Rev. Cancer 6, 281-291.

Schramek, D., Leibbrandt, A., Sigl, V., Kenner, L., Pospisilik, J. A., Lee, H. J., Hanada, R., Joshi, P. A., Aliprantis, A., Glimcher, L., et al. (2010). Osteoclast differentiation factor RANKL controls development of progestin-driven mammary cancer. Nature 468, 98-102.

Seguin, L., Kato, S., Franovic, A., Camargo, M. F., Lesperance, J., Elliott, K. C., Yebra, M., Mielgo, A., Lowy, A. M., Husain, H., et al. (2014). An integrin beta(3)-KRAS-RalB complex drives tumour stemness and resistance to EGFR inhibition. Nat. Cell Biol. 16, 457-468.

Shackleton, M., Vaillant, F., Simpson, K. J., Stingl, J., Smyth, G. K., Asselin-Labat, M. L., Wu, L., Lindeman, G. J., and Visvader, J. E. (2006). Generation of a functional mammary gland from a single stem cell. Nature 439, 84-88.

Sloan, E. K., Pouliot, N., Stanley, K. L., Chia, J., Moseley, J. M., Hards, D. K., and Anderson, R. L. (2006). Tumor-specific expression of αvβ3 integrin promotes spontaneous metastasis of breast cancer to bone. Breast Cancer Res. 8, R20.

Smith, G. H., and Medina, D. (2008). Re-evaluation of mammary stem cell biology based on in vivo transplantation. Breast Cancer Res. 10, 203.

Spike, B. T., Engle, D. D., Lin, J. C., Cheung, S. K., La, J., and Wahl, G. M. (2012). A mammary stem cell population identified and characterized in late embryogenesis reveals similarities to human breast cancer. Cell Stem Cell 10, 183-197.

Stingl, J. (2009). Detection and analysis of mammary gland stem cells. J. Pathol. 217, 229-241.

Stingl, J., Eirew, P., Ricketson, I., Shackleton, M., Vaillant, F., Choi, D., Li, H. I., and Eaves, C. J. (2006). Purification and unique properties of mammary epithelial stem cells. Nature 439, 993-997.

Taddei, I., Deugnier, M. A., Faraldo, M. M., Petit, V., Bouvard, D., Medina, D., Fassler, R., Thiery, J. P., and Glukhova, M. A. (2008). Beta1 integrin deletion from the basal compartment of the mammary epithelium affects stem cells. Nat. Cell Biol. 10, 716-722.

Takayama, S., Ishii, S., Ikeda, T., Masamura, S., Doi, M., and Kitajima, M. (2005). The relationship between bone metastasis from human breast cancer and integrin alpha (v)beta3 expression. Anticancer Res. 25 (1A), 79-83.

Taverna, D., Crowley, D., Connolly, M., Bronson, R. T., and Hynes, R. O. (2005). A direct test of potential roles for beta3 and beta5 integrins in growth and metastasis of murine mammary carcinomas. Cancer Res. 65, 10324-10329.

Vaillant, F., Asselin-Labat, M. L., Shackleton, M., Forrest, N. C., Lindeman, G. J., and Visvader, J. E. (2008). The mammary progenitor marker CD61/beta3 integrin identifies cancer stem cells in mouse models of mammary tumorigenesis. Cancer Res. 68, 7711-7717.

van Amerongen, R., Bowman, A. N., and Nusse, R. (2012). Developmental stage and time dictate the fate of Wnt/b-catenin-responsive stem cells in the mammary gland. Cell Stem Cell 11, 387-400.

Van Keymeulen, A., Rocha, A. S., Ousset, M., Beck, B., Bouvencourt, G., Rock, J., Sharma, N., Dekoninck, S., and Blanpain, C. (2011). Distinct stem cells contribute to mammary gland development and maintenance. Nature 479, 189-193.

Visvader, J. E. (2009). Keeping abreast of the mammary epithelial hierarchy and breast tumorigenesis. Genes Dev. 23, 2563-2577.

Wagner, K. U., Boulanger, C. A., Henry, M. D., Sgagias, M., Hennighausen, L., and Smith, G. H. (2002). An adjunct mammary epithelial cell population in parous females: its role in functional adaptation and tissue renewal. Development 129, 1377-1386.

Wu, et al (2012) Canonical Wnt signaling regulates Slug activity and links epithelial-mesenchymal transition with epigenetic Breast Cancer 1, Early Onset (BRCA1) repression. Proc. Natl. Acad. Sci. USA 109, 16654-16659.

A number of exemplary embodiments have been described. Nevertheless, it will be understood that various modifications may be made without departing from the spirit and scope of the invention. Accordingly, other embodiments are within the scope of the following claims.

What is claimed is:

1. A method for identifying or screening for an agent or a compound:
   that inhibits or decreases the amount of metastasis or circulating tumor cells;
   that reverses cancer cell acquired resistance to a drug; and/or
   that inhibits, negatively affects or decreases anchorage independent growth of a cancer cell,
   comprising:
   (a) providing a test compound;
   (b) providing a recombinant or an engineered cell, or a cell free expression system, comprising a nucleic acid construct or a chimeric or recombinant nucleic acid comprising
   a beta3-integrin (ITGB3) promoter operably linked to a nucleic acid encoding a reporter or a marker protein or marker compound,
   wherein inhibiting activity of the beta3-integrin (ITGB3) promoter results in decreased expression and measurable levels of the nucleic acid encoding the reporter or marker protein or marker compound;
   (c) measuring or determining the level of the nucleic acid encoding the reporter or marker protein or marker compound before adding the test compound, and
   (d) administering to or contacting the test compound with the recombinant or engineered cell, or to the cell free expression system, and measuring or determining the level of the nucleic acid encoding the reporter or marker protein or marker compound,
   wherein measuring or determining an increase in the level of the nucleic acid encoding the reporter or marker protein or marker compound, as compared to the level measured in step (c), indicates that the test compound is an beta3-integrin (ITGB3) promoter inducer,
   and wherein measuring or determining a decrease in the level of the nucleic acid encoding the reporter or marker protein or marker compound, as compared to the level measured in step (c), indicates that the test compound is a beta3-integrin (ITGB3) promoter inhibitor,
   and by measuring or determining a decrease in the level of the nucleic acid encoding the reporter or marker protein or marker compound, as compared to the level measured in step (c), indicates that the test compound can: inhibit or decrease the amount of metastasis or circulating tumor cells; reverse cancer cell acquired resistance to a drug; and/or inhibit, negatively affect or decrease anchorage independent growth of a cancer cell.

2. The method of claim 1, further comprising administering a negative control compound known to not affect beta3-integrin (ITGB3) promoter activity.

3. The method of claim 1, wherein the nucleic acid construct, or a chimeric or recombinant nucleic acid comprises or is contained in an expression cassette, a vector, a plasmid, a phagemid or an artificial chromosome.

4. The method of claim 1, wherein the test compound comprises or is a biologic, a drug, a small molecule or a small molecule drug, a bio-molecule, a protein, a lipid, a polysaccharide, or a nucleic acid.

5. The method of claim 1, wherein the reporter or marker protein or compound comprises a bioluminescent or a fluorescent protein or compound, or a luciferase or a green fluorescent protein (GFP).

6. The method of claim 1, wherein the nucleic acid construct or a chimeric or recombinant nucleic acid further comprises an ITGB3 enhancer.

7. The method of claim 1, wherein the ITGB3 promoter is an ITGB3 distal promoter.

8. The method of claim 7, wherein the ITGB3 distal promoter comprises a sequence as set forth in SEQ ID NO:2.

9. The method of claim 1, wherein the beta3-integrin (ITGB3) promoter is constitutively active and the reporter nucleic acid, or the reporter or marker protein is constitutively expressed.

10. The method of claim 1, wherein the beta3-integrin (ITGB3) promoter is inducibly expressed before addition of the test compound, resulting in inducible expression of the reporter nucleic acid, or the reporter or marker protein.

11. The method of claim 10, wherein the beta3-integrin (ITGB3) promoter is inducibly expressed by addition of a chemical or a drug or a conditioned media.

12. The method of claim 11, wherein the conditioned media is obtained from serum deprived cells or cancer cells.

13. The method of claim 1, wherein the beta3-integrin (ITGB3) promoter is inducibly expressed by addition of erlotinib.

* * * * *

SEQUENCE LISTING

```
<160> NUMBER OF SEQ ID NOS: 2

<210> SEQ ID NO 1
<211> LENGTH: 1319
<212> TYPE: DNA
<213> ORGANISM: artificial sequence
<220> FEATURE:
<223> OTHER INFORMATION: synthetic oligonucleotide
```

```
<400> SEQUENCE: 1
tttgcagagc tggcttttcc ccttgcaaat tgctagtgac gcttcagctg atgtgtgtta    60
ctattaaggt cctagtgttt gggagggtgg ggcaggaggt ggaggattgt cagaaaaaaa   120
ttacatggaa aaagatggca tctgagatgt tttgaaagat aagtggaatt ttccaagtgg   180
aaaaaggaag gaaaatcagt cagataggaa ggcatggagc attggggaat gacaagtatc   240
ttcttggact agggtgggag atgggctgga gagatgggtc agggccagtt gtctggcatc   300 tgtgtgtct cagaagaggg tgggcacgct gcgtagggaa gcccagggcc actctgaaag   360
ccctaaaggg gaactgatgc ctctggcctt gtttttatca ccatcaggac tacccattga   420
ggcaggctgc actaccagct acttcctggt gccctcttgc tcatagccat agtattttgc   480
ctctctgagc ttccagaggt tttaagtctg gggaagaccc agggactcaa agaaagattg   540
gggtgggaga taaggggcca cagtttgggg gagtcaggca ggaggccttt gaggaaaata   600
gataaagtcc caaagcctgt gagtgtgaat ttggaggcaa tatgctgtgt tctgaaacgt   660
tttcagacac tggctaggtg caagcaagtg tttgtagggc gaggctcttc atggacctat   720
cactgcttac gcaagcttgg gatgtggtct tgccctcaac aggtaggtag tctaccggaa   780
aaccaaacta aggcaagaaa aaattagtg aataataaag gactgaaccg gttcagagaa   840
ggcattcagc agatgtttgc cagtcaaatg aattaaagtg tgaatgaatg aaactcgagg   900
tagtgggtga atgtgtccca agaatccagc gaaacagggt ctcccaggag gcgggactgg   960
aagggtccgg agaggggcca caggctcctg gcctttctaa gcacaccaag tgcccagtcg  1020 cggaccccg ggaccaggat gcgctgacga cccggctggc aggcgggtcc tcgtgggcga  1080
ggcgagggag gcggcgagag aggagcaata gtttcccacc gctccctctc aggcgcaggg  1140
tctagagaag cgcgaggga tctagagaag ccggagggga ggaagcgcga gtccgcggcc  1200
cgccccgttg cgtcccaccc accgcgtccc ctccctccc ctcccgctgc gggaaaagcg  1260
gccgcgggcg gcggcgccca ctgtggggcg ggcggagcgc cgcgggaggc ggacgagat   1319

<210> SEQ ID NO 2
<211> LENGTH: 3780
<212> TYPE: DNA
<213> ORGANISM: artificial sequence
<220> FEATURE:
<223> OTHER INFORMATION: synthetic oligonucleotide

<400> SEQUENCE: 2
atcagtaagg atagtcttgc tacaaaatca ctcatatttt tatggttttt tttttaattt    60
ttaattttag aggcgaggat tcgaacctct gagttcatgc catcctccca tcttagcctc   120
ctgagtagca catgccactg tgcctggcta gctcatattt ttaaggtact tttttccccg   180
tctgtcttga tgaaaaaata caacttaaaa agttggcaca gataaacaga gctggggctt   240
atatcttata acctatgtaa ttaatatcat agccaaacct tcacatgctt ccttcccatc   300
ctctgccata ttacaattag attttgaggg actttgggag ttctatcccc ctaccttgaa   360
gggtatccat ggtcacctgc cacagtgccc caaatatcca ttattaatta cttttggggg   420
gtgtaggcat tgaaggcttc tgggtatggc ttgactattg agtgtttggc ctctgaagcc   480
agaatgccag agtttagaac tggagactcc tcttcctttc tgcaccttgg catccttctc   540
tctaaaatgg ggatgaaaac aacacccacc tcattaaggg atgttgtgag gatgttacaa   600
ggtaatatgt atgaggcatt tattagaata acacctggcc caaaatgagc cctcaataaa   660
tgtcagatgt aaagttatca acattcttgt cctcttagct taaatcttat tcagtgcatt   720
```

```
gcctagtaga attctgaggc acaacgagtc cattttatga cctgagcaaa ggaaagcgtt        780
aggaaacagg gcattcatta actagaatgg tcttaggctg aaagttttac catgtacaga        840
atcctctgag catttaaggg atcggtgtgc aggcaaagag ttcctaggga aggaccaaag        900
aatcagggtg aggcagacag aggatggcgg ttgagagtaa ctgcccaggg acggggaaca        960
cagcccttgg ggtaggcaca ggtatctgag tccctgaagc gaggagaatg gagccagagg       1020
ggtggagagg agagggagga ggcaggacca gagaggcaga ggagcgctcc tgccaggggt       1080
cctgtgcagt gaaggaggtg aggcctcacg gctgcttcct caggcctcat ggcttccagg       1140
caggtcttac tgggttggaa acacataggg ccatggggga agtgagacat gcttgctaat       1200
catacttcca gctcacagtc atctctctgt ttgtcatcct ttcaaggaaa agctgtatcc       1260
caagggccct ctgtttagct cagaccttgg cccaatgccc aggttttttct ggtgccacta       1320 tcatatctca ggattcagcc agacatggtt ggtaacttct tgtaatagtc aagacaggaa       1380
gtggtcagga cctggaaata gagcagccct tggggggtggg taggactgac ccagctctgg       1440
gtgcctcctc aggctagtgg cacagaattc ctggacttgg cctgggctgc agcgacgcta       1500
gagataatgt ctttatggat ttcccaattt tatctcagac aatgggaaat ctagtagtgt       1560
tttatgacaa acaggaattt ctcccattat catagcaatg ctgacttgaa acatttggga       1620
gtgcctgaca ttctataccc acacttacag taagggagac agtaggttgt agggtaagca       1680
ctgaagtcag gctgaacttt tctgaacccc atctttgcca ctaactccct ggtgctcttg       1740
agctaattac ctcatctctc tgtgcctcca ttttttcact tgtaaaatca ggatttcccc       1800
acgtatctta ccgcagacta aaaaaagaa aagtatgaaa gaatgcttag catagtatct       1860
tgaacacact aacctcaaaa taaatggcat ctagtaaaat catcatcatc atcatcatca       1920
ctgtctcttc gcccaccaag cttcagtttg cacctctata aaatgaggat tgagggaaat       1980
aatcaatatt tgcaatattt gtatagaagg tggtatatgg taggtgttct caaattctag       2040
ttccttccca tggaggaaag ccagacgctg ggaagagga cctgggtcag cagctcatgt       2100
gctgagggga agtggggttg ggggaaggga ggtcagtccc tggctggagt agacctgtgg       2160
agttaacccc ctctgctgag tagaaatgtc ggggactgga caatggactg gcactgaatt       2220
caggcagatt tgggagaact gactaggtcc tgctactcca gagaagctgg tgagtggcag       2280
gctggagtag tgaaagcaga tagctgacag tgtgggtatt ggctatagca agggccttcc       2340
tgagtcctca gtggcccaaa ctagcctcat ggtgttctag atcctaggat tcctctggag       2400
caattgttct ttttttttct tattatagat atgtttttaa aaatttcaat gcttttgga       2460 gtacaagtgg ttttttgatta tatggatgaa ttgtataatg gtgaagtctg atattttact       2520
gcacccatca cctgggtagt atatattgta cccaatatgt gttttttta tccctcaacc       2580 ccctcaacct tccccttct gagtctccaa agtccattat accactctgt ttgcctttgc       2640
atacccatag cttagctccc acttataagt gagaacatac agtatttggt tttccactcc       2700
tgaattactt cacttagaat gatggcctcc agctccatcc aagttactgc aaaatacatt       2760
atgtccttcc tttttatggc tgagtagtat tccatgatgt ctatatacca cattttcttt       2820 tttattttttg agaccgacac tcgctctgtc gtccaggctg gagtgcaatg gtgcaatctt       2880
ggctcactgc aacctctgcc tcccaggttc aagtggttct cctccctcag cctcccgagt       2940
agttgtggtt acaggtgtgc acctccatcc ccagctaact tttgtatttt tagtagacac       3000
ggggtttcac catgttggcc gggctggtct cgaacccctg atctcaggtg atccacccgc       3060
ctcggcctcc caaagtgctg ggattacagg catgagccac catgcccaac tactacattt       3120
```

-continued

```
tctttatcca ctcatcagtt gataggtact taggttgatt ccgtatcttt gcagttgtga    3180
attgtgctgt gataaaccta cgcatgcagg tgtcttttg atgcaatgac ttctttcct      3240 ttgggtagat acccagtagt gagattgctg gatggagtgg tagatctact tttagttctt    3300
taagaaggtg gaacaattgt tgttaaccct agaggtcaca gacccgtttg agaagctagt   3360
gaaaactaag gagcatttct atagaaaaat gcatatcaca caaatgtttg catattagag    3420
gggcctcaca gatccccagg aactcatcaa gggacttcag gtgaagaaac ctggtggact    3480
tgtcccagca gcactaatta agcccaagga ctagacacta gatccacccg tgggttggca   3540
cagggcacag gacctgatcc aggagctgtc agaggatgct cagtttgact ggtaaagaca    3600
gtacccagac agtatgcaac ctcctcctgc ctccattcag ccaacattgt ccagggagct    3660
agagatgggc agcaacaatg aaaatcagta ggtatcctga ctcgtaggca gaatgtgggg    3720
gtagattaaa ccagcataga tgagttgatc ctaagaggaa aaaatagctc ttatttattt    3780
```